«12» United States Patent
Liu

(10) Patent No.: US 6,685,914 B1
(45) Date of Patent: Feb. 3, 2004

(54) MACROCYCLIC CHELANTS FOR METALLOPHARMACEUTICALS

(75) Inventor: Shuang Liu, Chelmsford, MA (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 113 days.

(21) Appl. No.: 09/660,377

(22) Filed: Sep. 12, 2000

Related U.S. Application Data

(60) Provisional application No. 60/153,512, filed on Sep. 13, 1999.

(51) Int. Cl.[7] .................................................. A61B 49/00
(52) U.S. Cl. ........................ 424/9.3; 424/1.11; 424/9.1; 424/1.65; 540/465; 534/10; 534/14
(58) Field of Search ............................... 424/1.11, 1.65, 424/9.1, 9.3, 9.4, 9.5, 9.6, 9.7, 9.8; 534/7, 10–16; 540/450, 465

(56) References Cited

U.S. PATENT DOCUMENTS 5,730,787 A    3/1998   Kasai

FOREIGN PATENT DOCUMENTS

| WO | WO 88/07048 | 9/1988 |
|---|---|---|
| WO | WO 94/03464 | 2/1994 |
| WO | WO 94/26275 | 11/1994 |
| WO | WO 95/28968 | 11/1995 |

Primary Examiner—Dameron L. Jones
(74) Attorney, Agent, or Firm—Paul D. Golian; Woodcock Washburn LLP

(57) ABSTRACT

This invention relates to macrocyclic chelants comprised of one or two heteroatom-containing bridges, compositions containing them and their use in medicine, particularly in diagnostic imaging and radiotherapy. This invention relates especially to the use of metal chelates of the macrocyclic chelants as metallopharmaceuticals in Magnetic Resonance Imaging (MRI) and radiopharmaceuticals. This invention also relates to macrocyclic chelants as bifunctional chelating agents (BFC's) for the labeling of biologically active targeting molecules such as proteins, peptides, peptidomimetics, and non-peptide receptor ligands, with metal ions and radioisotopes.

34 Claims, No Drawings

US 6,685,914 B1

MACROCYCLIC CHELANTS FOR METALLOPHARMACEUTICALS

This application claims the benefit of U.S. Provisional Application No. 60/153,512 filed Sep. 13, 1999.

FIELD OF THE INVENTION

This invention relates to new macrocyclic chelants and metal chelates thereof, methods of preparing the chelants and metal complexes, and pharmaceutical compositions comprising the macrocyclic chelants and metal complexes. This invention relates particularly to the use of the new metal chelates as contrast agents in X-ray imaging, magnetic resonance imaging (MRI) and radiopharmaceuticals. This invention also relates to new bifunctional chelants (BFC's) for attaching diagnostic and therapeutic isotopes to biologically active targeting molecules such as proteins, peptides, peptidomimetics, and non-peptide receptor ligands. In addition, the macrocyclic chelants are useful for heavy metal detoxification.

BACKGROUND OF THE INVENTION

Medical imaging modalities, such as MRI, X-ray, gamma scintigraphy, and CT scanning, have become extremely important tools in the diagnosis and treatment of various diseases and illness. Imaging of internal body parts relies on the contrast between the targeted organ and the surrounding tissues. The targeted organs or tissues are visible by the use of a particular metallopharmaceutical contast agent. In X-ray diagnostics, increased contrast of internal organs, such as kidney, the urinary tract, the digestive tract, the vascular system of the heart, tumor, and so forth is obtained by administering a contrast agent which is substantially radioopaque. In conventional proton MRI diagnostics, increased contrast of internal organs and tissues may be obtained by administrating compositions containing paramagnetic metal species, which increase the relaxivity of surrounding protons. In ultrasound diagnostics, improved contrast is obtained by administering compositions having acoustic impedances different than that of blood and other tissues. In gamma scintigraphy, improved contrast of internal organ is obtained by the specific localization of a radiopharmaceutical.

Attachment of metal ions to biomolecules such as antibodies, antibody fragments, peptides, peptidomimetics, and non-peptide receptor ligands leads to useful target-specific diagnostic and therapeutic metallo-pharmaceuticals. These include fluorescent, radioactive and paramagnetic metal ions attached to proteins that can be used as probes in vivo in biological systems and in vitro in analytical systems as radioimmunoassays. For example, attachment of radionuclides to monoclonal antibodies that recognize tumor associated antigens provides radioimmunoconjugates useful for cancer diagnosis and therapy. The monoclonal antibodies are used as carriers of desired radioisotope to the tumor in vivo.

Radiopharmaceuticals can be classified into two primary classes: those whose biodistribution is determined exclusively by their chemical and physical properties; and those whose ultimate distribution is determined by receptor binding or other biological interactions. The latter class is often called target-specific radiopharmaceuticals. In general, a target specific radiopharmaceutical can be divided into four parts: a targeting molecule, a linker, a bifunctional chelator (BFC), and a radionuclide. The targeting molecule serves as a vehicle which carries the radionuclide to the receptor site at the diseased tissue. The targeting molecules can be macromolecules such as antibodies; they can also be small biomolecules (BM) such as peptides, peptidomimetics, and non-peptide receptor ligands. The choice of biomolecule depends upon the targeted disease or disease state. The radionuclide is the radiation source. The selection of radionuclide depends on the intended medical use (diagnostic or therapeutic) of the radiopharmaceutical. Between the targeting molecule and the radionuclide is the BFC, which binds strongly to the metal ion and is covalently attached to the targeting molecule either directly or through a linker. Selection of a BFC is largely determined by the nature and oxidation state of the metallic radionuclide. The linker can be a simple hydrocarbon chain or a long polyethylene glycol (PEG), which is often used for modification of pharmacokinetics. Sometimes, a metabolizeable linker is used to increase the blood clearance and to reduce the background activity, thereby improving the target-to-background ratio.

The use of metallic radionuclides offers many opportunities for designing new radiopharmaceuticals by modifying the coordination environment around the metal with a variety of chelators. The coordination chemistry of the metallic radionuclide will determine the geometry of the metal chelate and the solution stability of the radiopharmaceutical. Different metallic radionuclides have different coodination chemistries, and require BFC's with different donor atoms and ligand frameworks. For "metal essential" radiopharmaceuticals, the biodistribution is exclusively determined by the physical properties of the metal chelate. For target-specific radiopharmaceuticals, the "metal tag" is not totally innocent because the target uptake and biodistribution will be affected by the metal chelate, the linker, and the targeting biomolecule. This is especially true for radiopharmaceuticals based on small molecules such as peptides, due to the fact that in many cases the metal chelate contributes greatly to the overall size and molecular weight. Therefore, the design and selection of the BFC is very important for the development of a new radiopharmaceutical.

The same principle used for target-specific metalloradiopharmaceuticals also applies to target-specific MRI contrast agents and ultrasound agents. Unlike the target-specific metalloradiopharmaceutical, where excess unlabeled biomolecule can compete with the radiolabeled-BFC-biomolecule conjugate and block the docking of the radiolabeled receptor ligand, MRI and ultrasound contrast agents contain no excess BFC-biomolecule conjugate. Saturation of the receptor sites will maximize the contrast between the diseased tissues and normal tissue provided that the use of a relatively large amount of metal-BFC-biomolecule complex does not cause unwanted side effects.

Several BFC systems such as ethylenediaminetetraacetic acid (EDTA) and diethylenetriaminepetaacetic acid (DTPA), as well as their derivatives, have been reported to form thermodynamically stable metal chelates when attached to proteins. However, in vivo instability of the radioimmunoconjugate or the chelate under physiological conditions results in the breakdown of these complexes. Hence, there is a continuing need for new BFC's with a macrocyclic ligand framework for the radiolabeling of biomolecules such as antibodies, antibody fragments, peptides, peptidomimetics, and non-peptide receptor ligands.

For a therapeutic radiopharmaceutical or an MRI contrast agent, it is especially important to keep the metal chelate intact under the physiological conditions, particularly in the presence of native chelators, such as transferrin, which have very high affinity for trivalent lanthanide metal ions. This requires the chelant to form a metal chelate with thermodynamic stability and kinetic inertness. Macrocyclic chelants with three-dimensional cavities are of particular interest because they form metal complexes with high stability. They often exhibit selectivity for certain metal ions based on metal size and coordination chemistry, and capability to adopt an preorganized conformation in the uncomplexed form, which facilitates metal complexation.

Polyaza macrocycles have been widely used as chelants for a variety of transition metals. The macrocyclic polyaminocarboxylates such as 1,4,7,10-tetraazacyclo-dodecane-1, 4,7,10-tetracetic acid (DOTA) and 1,4,8,11-tetraazacyclo-tetradecane-1,4,8,11-tetracetic acid (TETA) are known to form highly stable metal complexes due to their highly preorganized macrocyclic ligand framework. Their Gd complexes have been widely used as MRI contrast agents. Examples include gadolinium complexes Gd-DOTA (Dotarem™, Guerbet/France), Gd-HP-DO3A (ProHance™, Bracco/Italy), and Gd-DO3A-butrol (Gadovist™, Schering/Germany). These macrocyclic chelants have also been used as BFC's for the radiolabeling of proteins and peptides with various diagnostic and therapeutic radionuclides (such as $^{111}$In and $^{90}$Y). In all those cases, the linkages between N-donors of the macrocycle are either ethylene- or propylene-bridges.

SUMMARY OF THE INVENTION

The present invention provides macrocyclic chelants that can rapidly form highly stable metal chelates, which are useful as diagnostic or therapeutic metalloradiopharmaceuticals, or magnetic resonance imaging contrast agents. The macrocyclic chelants can also serve as bifunctional chelators (BFC's) for attaching metal ions to bio-directing groups including proteins, peptides, peptidomimetics, and non-peptides that bind in vivo to a receptor or enzyme that is expressed or up-regulated at a site or in a disease state. The target specific metallopharmaceuticals of the present invention are useful in the diagnosis of disease by magnetic resonance imaging or scintigraphy or in the treatment of disease by systemic radiotherapy.

The novel macrocyclic chelants described in this invention are comprised of one or more heteroatom-containing linkages between the N-donors of the macrocycle. This is significant because the heteroatoms can also bind to the metal center. These macrocyclic chelants are expected to form stable complexes with divalent or trivalent metal ions such as $Cu^{2+}$, $Ga^{3+}$, $In^{3+}$, $Y^{3+}$, $Sm^{3+}$, $Gd^{3+}$, $Dy^{3+}$, $Ho^{3+}$, $Yb^{3+}$, and $Lu^{3+}$. Due to the macrocyclic effect, the metal complexes are kinetically inert with respect to dissociation, which is important for the development of metallopharmaceuticals.

The utility of these new chelants and their metal chelates depends on the choice of chelating arms and metal ion. For example, if the substituent groups on the four nitrogen-atoms are all phosphonomethyl ($CH_2PO_3H_2$) or a combination of carboxymethyl and phosphonomethyl groups, the radiolanthanide chelates can be used as therapeutic radiopharmaceuticals for bone-pain palliation or for the treatment of bone metastases. If the N-substituent groups are all carboxymethyl groups, the corresponding lanthanide (particularly gadolinium) complexes can be used as MRI contrast agents. If the N-substituent groups are alkyl groups, the macrocyclic chelants can form six-coordinate complexes with $Cu^{2+}$, $Ga^{3+}$, $In^{3+}$ with four N-donors in the equatorial positions and the two heteroatoms, such as phosphinate-oxygens, at the remaining two apical sites. Both the substituents on heteroatoms and the carboxylic acid functionalities can be used for attachment of biomolecules such as proteins, peptides, peptidomimetics, carbohydrates, fatty acids, and polynucleotides. These macrocyclic chelants can also be functionalized at the carbon atoms of the macrocyclic backbone.

The utility of these molecules also includes (1) use as chelants for the treatment of heavy metal intoxication, (2) use as chelants to form radioactive metal chelates which can be used as the radiation source (when given the appropriate radioisotopes) in a controlled-release vehicle or device, and (3) use as therapeutic agents themselves for the treatment of metabolic bone diseases such as osteoporosis, if substituent groups on the four nitrogen-atoms are all phosphonomethyl ($CH_2PO_3H_2$) or a combination of carboxymethyl and phosphonomethyl groups. The $^{32/33}$P-labeled chelants are also useful as therapeutic radiopharmaceuticals for bone cancer since polyphosphonates have high binding affinity towards the bone.

DETAILED DESCRIPTION OF THE INVENTION

The present invention provides macrocyclic chelants that can rapidly form highly stable metal chelates, which are useful as diagnostic or therapeutic metalloradiopharmaceuticals, or magnetic resonance imaging contrast agents. The macrocyclic chelants can also serve as bifunctional chelators (BFC's) for attaching metal ions to bio-directing groups including proteins, peptides, peptidomimetics, and non-peptides that bind in vivo to a receptor or enzyme that is expressed or up-regulated at a site or in a disease state. The target specific metallopharmaceuticals of the present invention are useful in the diagnosis of disease by magnetic resonance imaging or scintigraphy or in the treatment of disease by systemic radiotherapy.

[1] One embodiment of the present invention is a compound of formulae (I) or (II):

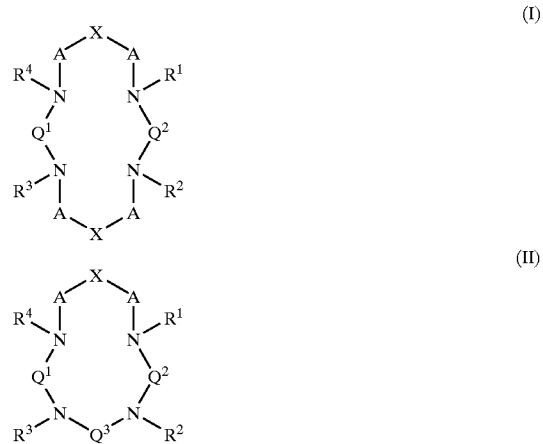

and pharmaceutically acceptable salts therefore wherein:

$R^1$, $R^2$, $R^3$ and $R^4$ are independently selected at each occurrence from the group: $C_1$–$C_{10}$ alkyl substituted with 0–5 $R^5$, $C_2$–$C_{10}$ alkenyl substituted with 0–5 $R^5$, and aryl substituted with 0–5 $R^5$;

$R^5$ is independently elected at each occurrence from the group: H, $C(=O)OR^{18}$, $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is selected from the group: $BR^6R^7$, $C(=O)$, $SiR^6R^7$, $GeR^6R^7$, $SnR^6R^7$, $NR^8$, $PR^9$, $P(=O)R^9$, $P(=S)R^9$, $AsR^9$ and $As(=O)R^9$;

A is selected from the group: $CH_2$, $NR^{10}$ and O;

$Q^1$, $Q^2$, and $Q^3$ are independently $-(CR^{11}R^{12})_n-$, wherein: n is 2–5;

$R^6$ and $R^7$ are independently selected from the group: $C_1-C_{10}$ alkyl substituted with 0–5 $R^{13}$, $C_2-C_{10}$ alkenyl substituted with 0–5 $R^{13}$ and aryl substituted with 0–5 $R^{13}$;

or alternatively, $R^6$ and $R^7$ may be taken together to form a transannular bridge, said bridge selected from the group: $C_{3-C10}$ alkyl substituted with 0–5 $R^{13}$ and ortho-aryl substituted with 0–3 $R^{13}$;

$R^8$ is selected from the group: $OR^{14}$, $C(=O)R^{14}$, $S(=O)_2R^{14}$ and $P(=O)(OR^{14})$;

$R^9$ is selected from the group: $OR^{14}$, $NR^{15}R^{16}$ and $CH_2NR^{15}R^{16}$;

$R^{10}$, $R^{11}$ and $R^{12}$ are independently selected from the group: H, $C_1-C_{10}$ alkyl substituted with 0–5 $R^{17}$, $C_2-C_{10}$ alkenyl substituted with 0–5 $R^{17}$ and aryl substituted with 0–3 $R^{17}$;

$R^{13}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SR^{18}$, $SOR^{18}$, $SO_2R^{18}$, $NHC(=O)R^{18}$, $NHC(=O)NHR^{18}$, $CH_2OR^{18}$, $CH_3$ and $NHC(=S)NHR^{18}$;

$R^{14}$, $R^{15}$ and $R^{16}$ are independently selected from the group: hydrogen, $C_1-C_{10}$ alkyl substituted with 0–5 $R^{13}$, $C_2-C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3-C_{10}$ alkyl substituted with 0–5 $R^{13}$ and ortho-aryl substituted with 0–3 $R^{13}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SR^{18}$, $SOR^{18}$, $SO_2R^{18}$, $NHC(=O)R^{18}$, $NHC(=O)NHR^{18}$ and $NHC(=S)NHR^{18}$; and $R^{18}$ is independently selected at each occurrence from the group: H, $C_1-C_6$ alkyl, benzyl and phenyl.

[2] Another embodiment of the present invention is a compound of embodiment [1], wherein:

X is selected from the group: $NR^8$, $PR^9$ and $P(=O)R^9$;

A is $CH_2$;

$R^8$ is selected from: $OR^{14}$, $C(=O)R^{14}$ and $S(=O)_2R^{14}$; and $R^9$ is $CH_2NR^{15}R^{16}$.

[3] Another embodiment of the present invention is a compound of embodiment [2], wherein:

X is $P(=O)OH$;

A is $CH_2$;

$Q^1$, $Q^2$, and $Q^3$ are independently $-(CR^{11}R^{12})_n-$, wherein: n is 2 or 3;

$R^{11}$ and $R^{12}$ are independently selected from the group: H, $C_1-C_5$ alkyl substituted with 0–3 $R^{17}$ and aryl substituted with 0–1 $R^{17}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R^{18}$, $SO_2R^{18}$, $NHC(=O)R^{18}$, $NHC(=O)NHR^{18}$ and $NHC(=S)NHR^{18}$; and $R^{18}$ is independently selected at each occurrence from the group: H and $C_1-C_3$ alkyl.

[4] Another embodiment of the present invention is a compound of embodiment [3], wherein:

$R^1$, $R^2$, $R^3$ and $R^4$ are independently selected at each occurrence from the group: H, $CH_2COOH$, $CH_2PO_3H_2$ and $CH_2$—heterocycle substituted with 0–3 $R^{13}$; and $R^{13}$ is independently selected at each occurrence from the group: H, OH, $NH_2$, COOH, $PO_3H_2$, $CH_2OH$, $CH_3$ and $SO_3H$.

[5] Other embodiments of the present invention are the compounds of embodiment [4] that are selected from the group:

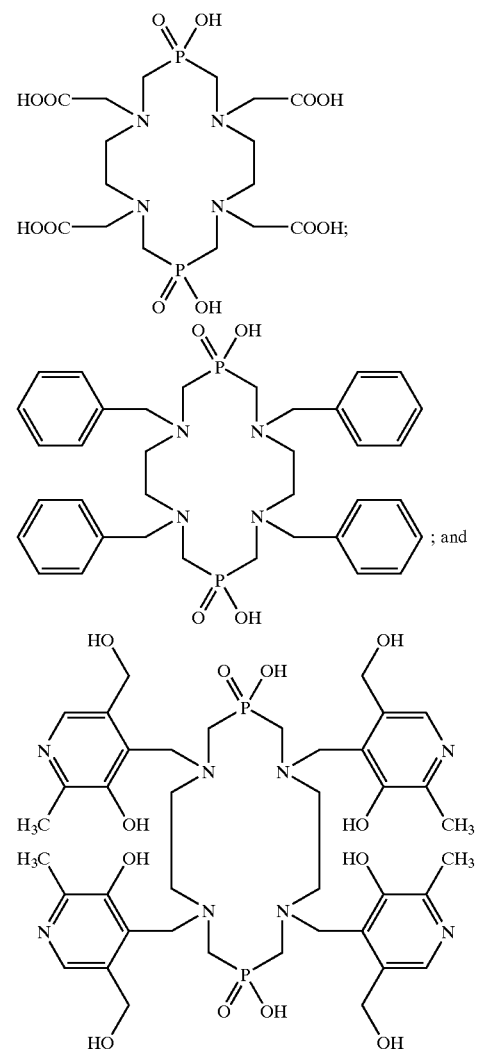

[6] Another embodiment of the present invention is a radiopharmaceutical of formulae (III) or (IV):

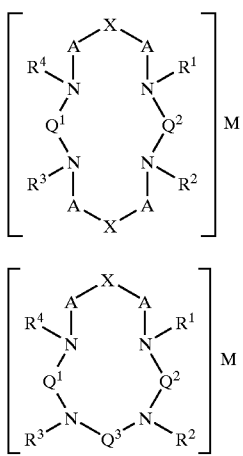

and pharmacuetically acceptable salts therefore, wherein:

M is selected from the group: $^{64}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$, and $^{188}Re$;

$R^1$, $R^2$, $R^3$ and $R^4$ are independently selected at each occurrence from the group: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently selected at each occurrence from the group: H, $C(=O)OR^{18}$, $C(=O)OR^{23}$, $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is selected at from the group: $BR^6R^7$, $C(=O)$, $SiR^6R^7$, $GeR^6R^7$, $SnR^6R^7$, $NR^8$, $PR^9$, $P(=O)R^9$, $P(=S)R^9$, $AsR^9$ and $As(=O)R^9$;

A is selected from the group: $CH_2$, $NR^{10}$ and O; $Q^1$, $Q^2$, and $Q^3$ are independently $—(CR^{11}R^{12})_n—$, wherein: n is 2–5;

$R^6$ and $R^7$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or alternatively, $R^6$ and $R^7$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^8$ is selected from the group: $OR^{23}$, $OR^{14}$, $C(=O)R^{14}$, $S(=O)_2R^{14}$ and $P(=O)(OR^{14})$;

$R^9$ is selected from the group: $OR^{14}$, $NR^{15}R^{16}$ and $CH_2NR^{15}R^{16}$;

$R^{10}$, $R^{11}$ and $R^{12}$ are independently selected from the group: H, $C_1$–$C_{10}$ alkyl substituted with 0–5 $R^{17}$, $C_2$–$C_{10}$ alkenyl substituted with 0–5 $R^{17}$ and aryl substituted with 0–3 $R^{17}$;

$R^{13}$ is independently selected at each occurrence from the group: H, OH, $OR^{23}$, $NHR^{18}$, $C(=O)R^{18}$, $OC(=O)R^{18}$, $OC(=O)OR^{18}$, $OC(=O)OR^{23}$, $C(=O)OR^{18}$, $C(=O)OR^{23}$, $C(=O)NR_2^{18}$, $PO_3R_2^{18}$, $PO_3R^{18}R^{23}$, $SR^{18}$, $SR^{23}$, $SOR^{18}$, $SO_2R^{18}$, $SOR^{23}$, $SO_2R^{23}$, $NHC(=O)R^{18}$, $NHC(=O)NHR^{18}$, $CH_2OR^{18}$, $CH_2OR^{23}$, $CH_3$ and $NHC(=S)NHR^{18}$; or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$, $R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SR^{18}$, $SOR^{18}$, $SO_2R^{18}$, $NHC(=O)R^{18}$, $NHC(=O)NHR^{18}$ and $NHC(=S)NHR^{18}$;

$R^{18}$ is independently selected at each occurrence from the group: H, $C_1$–$C_6$ alkyl, benzyl, and phenyl; and $R^{23}$ is a bond to the metal M.

[7] Another embodiment of the present invention is a radiopharmaceutical of embodiment [6], wherein:

X is selected from the group: $NR^8$, $PR^9$ and $P(=O)R^9$;

A is $CH_2$;

$R^8$ is selected from the group: $OR^{23}$, $OR^{14}$, $C(=O)_2R^{14}$ and $S(=O)_2R^{14}$; and $R^9$ is $CH_2NR^{15}R^{16}$.

[8] Another embodiment of the present invention is a radiopharmaceutical of embodiment [7], wherein:

X is $P(=O)OH$;

A is $CH_2$;

$Q^1$, $Q^2$, and $Q^3$ are independently $—(CR^{11}R^{12})_n—$, wherein: n is 2 or 3;

$R^{11}$ and $R^{12}$ are independently selected from the group: H, $C_1$–$C_5$ alkyl substituted with 0–3 $R^{17}$ and aryl substituted with 0–1 $R^{17}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SO_2R_{18}$, $NHC(=O)R^{18}$, $NHC(=O)NHR^{18}$ and $NHC(=S)NHR^{18}$; and $R^{18}$ is independently selected at each occurrence from the group: H and $C_1$–$C_3$ alkyl.

[9] Another embodiment of the present invention is a radiopharmaceutical of embodiment [8], wherein:

$R^1$, $R^2$, $R^3$ and $R^4$ are independently selected at each occurrence from the group: H, $CH_2COOH$, $CH_2PO_3H_2$ and $CH_2$—heterocycle substituted with 0–3 $R^{13}$; and $R^{13}$ is independently selected at each occurrence from the group: H, OH, $NH_2$, COOH, $PO_3H_2$, $CH_2OH$, $CH_3$ and $SO_3H$.

[9a] Another embodiment of the present invention is a radiopharmaceutical of embodiment [8], wherein: $R^{13}$ is independently selected at each occurrence from the group: $OR^{23}$, $OC(=O)OR^{23}$, $C(=O)OR^{23}$, $PO_3R^{18}R^{23}$, $SR^{23}$, $SOR^{23}$, $SO_2R^{23}$, $CH_2OR^{23}$,

[10] Another embodiment of the present invention is a radiopharmaceutical of the formula:

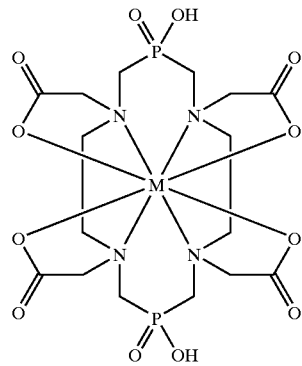

wherein:

M is selected from the group: $^{111}$In, $^{90}$Y and $^{177}$Lu.

[11] Another embodiment of the present invention is a radiopharmaceutical of the formula:

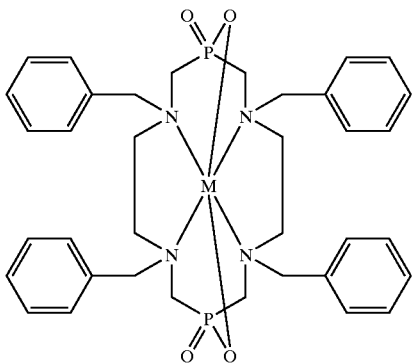

wherein:

M is selected from the group: $^{64}$Cu, $^{67}$Cu, $^{67}$Ga, $^{68}$Ga, $^{99m}$Tc, $^{111}$In, $^{90}$Y, $^{149}$Pr, $^{153}$Sm, $^{159}$Gd, $^{166}$Ho, $^{169}$Yb, $^{177}$Lu, $^{186}$Re, and $^{188}$Re.

[12] Another embodiment of the present invention is a radiopharmaceutical of the formula:

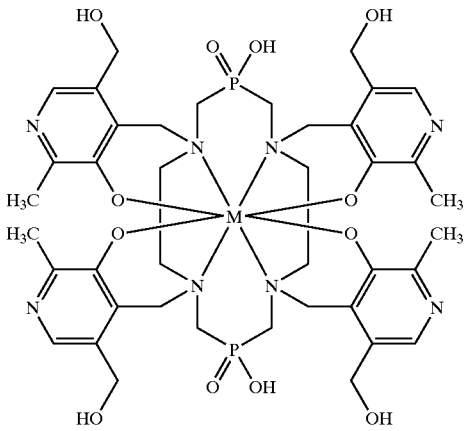

wherein:

M is selected from the group 64Cu, $^{67}$Cu, 67Ga, 68Ga, $^{99m}$Tc, $^{111}$In, $^{90}$Y, $^{149}$Pr, $^{153}$Sm, $^{159}$Gd, $^{166}$Ho, $^{169}$Yb, $^{177}$Lu, $^{186}$Re, and $^{188}$Re.

[13] Another embodiment of the present invention is an MRI contrast agent of formulae (V) or (VI):

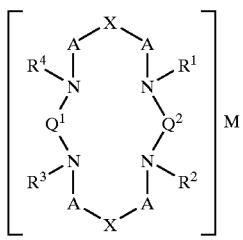

(V)

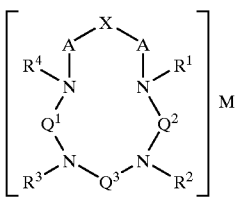

(VI)

and pharmaceutically acceptable salts thereof, wherein:

M is a paramagnetic metal ion of atomic number selected from the group: 21–29, 42–44 and 58–70;

$R^1$, $R^2$, $R^3$ and $R^4$ are independently selected at each occurrence from the group: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently elected at each occurrence from the group: H, C(=O)OR$^{18}$, C(=O)OR$^{23}$, $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is selected from the group: BR$^6$R$^7$, C(=O), SiR$^6$R$^7$, GeR$^6$R$^7$, SnR$^6$R$^7$, NR$^8$, PR$^9$, P(=O)R$^9$, P(=S)R$^9$, AsR$^9$ and As(=O)R$^9$;

A is selected from the group: CH$_2$, NR$^{10}$ and O;

$Q^1$, $Q^2$, and $Q^3$ are independently —(CR$^{11}$R$^{12}$)$_n$—, wherein: n is 2–5;

$R^6$ and $R^7$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or alternatively, $R^6$ and $R^7$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^8$ is selected from the group: OR$^{23}$, OR$^{14}$, C(=O)R$^{14}$, S(=O)$_2$R$^{14}$ and P(=O) (OR$^{14}$);

$R^9$ is selected from the group: OR$^{14}$, NR$^{15}$R$^{16}$ and CH$_2$NR$^{15}$R$^{16}$;

$R^{10}$, $R^{11}$ and $R^{12}$ are independently selected from the group: H, $C_1$–$C_{10}$ alkyl substituted with 0–5 $R^{13}$, $C_2$–$C_{10}$ alkenyl substituted with 0–5 $R^{17}$ and aryl substituted with 0–3 $R^{17}$;

$R^{13}$ is independently selected at each occurrence from the group: H, OH, NHR$^{18}$, C(=O)R$^{18}$, OC(=O)R$^{18}$, OC(=O)OR$^{18}$, C(=O)OR$^{18}$, C(=O)NR$_2^{18}$, PO$_3$R$_2^{18}$, SR$^{18}$, SOR$^{18}$, SO$_2$R$^{18}$, NHC(=O)R$^{18}$, NHC(=O)NHR$^{18}$, CH$_2$OR$^{18}$, CH$_3$ and NHC(=S)NHR$^{18}$;

$R^{14}$, $R^{15}$ and $R^{16}$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, NHR$^{18}$, C(=O)R$^{18}$, OC(=O)R$^{18}$, OC(=O)OR$^{18}$, C(=O)OR$^{18}$, C(=O)NR$_2^{18}$, PO$_3$R$_2^{18}$, SR$^{18}$, SOR$^{18}$, SO$_2$R$^{18}$, NHC(=O)R$^{18}$, NHC(=O)NHR$^{18}$ and NHC(=S)NHR$^{18}$; and $R^{18}$ is independently selected at each occurrence from the group: H, $C_1$–$C_6$ alkyl, benzyl and phenyl; and $R^{23}$ is a bond to the metal M.

[13a] Another embodiment of the present invention is an MRI contrast agent of formulae (V) or (VI):

wherein $R^{13}$ is independently selected at each occurrence from the group: H, OH, $OR^{23}$, $NHR^{18}$, $C(=O)R^{18}$, $OC(=O)R^{18}$, $OC(=O)OR^{18}$, $OC(=O)OR^{23}$, $C(=O)OR^{18}$, $C(=O)OR^{23}$, $C(=O)NR_2^{18}$, $PO_3R_2^{18}$, $PO_3R^{18}R^{23}$, $SR^{18}$, $SR^{23}$, $SOR^{18}$, $SO_2R^{18}$, $SOR^{23}$, $SO_2R^{23}$, $NHC(=O)R^{18}$, $NHC(=O)NHR^{18}$, $CH_2OR^{18}$, $CH_2OR^{23}$, $CH_3$ and $NHC(=S)NHR^{18}$;

[14] Another embodiment of the present invention is an MRI contrast agent of embodiment [13], wherein:

X is selected from the group: $NR^8$, $PR^9$ and $P(=O)R^9$;

A is $CH_2$;

$R^8$ is selected from the group: $OR^{23}$, $OR^{14}$, $C(=O)R^{14}$ and $S(=O)_2R^{14}$; and $R^9$ is $CH_2NR^{15}R^{16}$.

[15] Another embodiment of the present invention is an MRI contrast agent of embodiment [14], wherein:

X is $P(=O)OH$;

A is $CH_2$;

$Q^1$, $Q^2$, and $Q^3$ are independently $-(CR^{11}R^{12})_n-$, wherein: n is 2 or 3;

$R^{11}$ and $R^{12}$ are independently selected from the group: H, $C_1-C_5$ alkyl substituted with 0–3 $R^{17}$ and aryl substituted with 0–1 $R^{17}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SO_2R^{18}$, $NHC(=O)R^{18}$, $NHC(=O)NHR^{18}$ and $NHC(=S)NHR^{18}$; and $R^{18}$ is independently selected at each occurrence from the group: H and $C_1-C_3$ alkyl.

[16] Another embodiment of the present invention is an MRI contrast agent of embodiment [15], wherein:

$R^1$, $R^2$, $R^3$ and $R^4$ are independently selected at each occurrence from the group: H, $CH_2COOH$, $CH_2PO_3H_2$ and $CH_2$—heterocycle substituted with 0–3 $R^{13}$; and $R^{13}$ is independently selected at each occurrence from the group: H, OH, $NH_2$, COOH, $PO_3H_2$, $CH_2OH$, $CH_3$ and $SO_3H$.

[16] Another embodiment of the present invention is an MRI contrast agent of embodiment [15], wherein: $R^{13}$ is independently selected at each occurrence from the group: $OR^{23}$, $OC(=O)OR^{23}$, $C(=O)OR^{23}$, $PO_3R^{18}R^{23}$, $SR^{23}$, $SOR^{23}$, $SO_2R^{23}$ and $CH_2OR^{23}$.

[17] Another embodiment of the present invention is an MRI contrast agent of the formula:

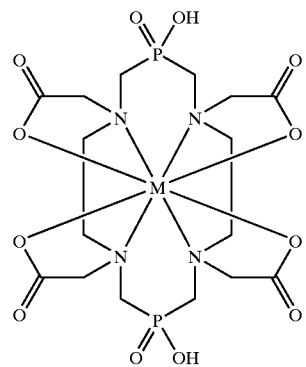

wherein:
M is a paramagnetic metal ion of atomic number selected from the group: 21–29, 42–44 and 58–70.

[18] Another embodiment of the present invention is an MRI contrast agent of the formula:

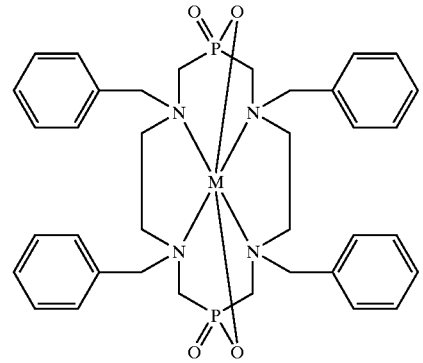

wherein:
M is a paramagnetic metal ion of atomic number selected from the group: 21–29, 42–44 and 58–70.

[19] Another embodiment of the present invention is an MRI contrast agent of the formula:

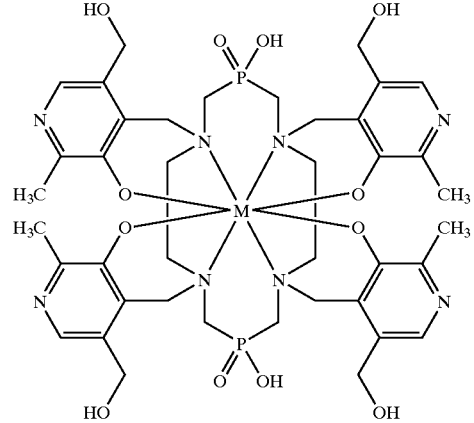

wherein:
M is a paramagnetic metal ion of atomic number selected from the group: 21–29, 42–44 and 58–70.

[20] Another embodiment of the present invention is a conjugate of the formula:

$C_h-L_n-W$, and pharmaceutically acceptable salts thereof, wherein:
$C_h$ is a chelator of formula (VII) or (VIII):

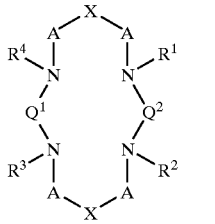

(VII)

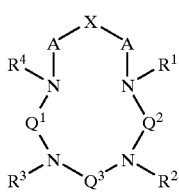

(VIII)

wherein:
$R^1$, $R^2$, $R^3$ and $R^4$ are independently selected at each occurrence from the group: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently elected at each occurrence from the group: H, C(=O)OR$^{18}$. $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is selected from the group: BR$^6$R$^7$, C(=O), SiR$^6$R$^7$, GeR$^6$R$^7$, SnR$^6$R$^7$, NR$^8$, PR$^9$, P(=O)R$^9$, P(=S)R$^9$, AsR$^9$ and As(=O)R$^9$;

A is selected from the group: CH$_2$, NR$^{10}$ and O;
$Q^1$, $Q^2$, and $Q^3$ are independently —(CR$^{11}$R$^{12}$)$_n$—, wherein: n is 2–5;

$R^6$ and $R^7$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or alternatively, $R^6$ and $R^7$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^8$ is selected from the group: OR$^{14}$, C(=O)R$^{14}$, S(=O)$_2$R$^{14}$ and P(=O)(OR$^{14}$);

$R^9$ is selected from the group: OR$^{14}$, NR$^{15}$R$^{16}$ and CH$_2$NR$^{15}$R$^{16}$;

$R^{10}$, $R^{11}$ and $R^{12}$ are independently selected from the group: H, $C_1$–$C_{10}$ alkyl substituted with 0–5 $R^{17}$, $C_2$–$C_{10}$ alkenyl substituted with 0–5 $R^{17}$ and aryl substituted with 0–3 $R^{17}$;

$R^{13}$ is independently selected at each occurrence from the group: H, OH, NHR$^{18}$, C(=O)R$^{18}$, OC(=O)R$^{18}$, OC(=O)OR$^{18}$, C(=O)OR$^{18}$, C(=O)NR$_2^{18}$, PO$_3$R$_2^{18}$, SR$^{18}$, SOR$^{18}$, SO$_2$R$^{18}$, NHC(=O)R$^{18}$, NHC(=O)NHR$^{18}$, CH$_2$OR$^{18}$, CH$_3$, NHC(=S)NHR$^{18}$ and a bond to $L_n$;

$R^{14}$, $R^{15}$ and $R^{16}$ are independently selected from the group: hydrogen, $c_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, NHR$^{18}$, C(=O)R$^{18}$, OC(=O)R$^{18}$, OC(=O)OR$^{18}$, C(=O)OR$^{18}$, C(=O)NR$_2^{18}$, PO$_2$R$^{18}$, SR$^{18}$, SOR$^{18}$, SO$_2$R$^{18}$, NHC(=O)R$^{18}$, NHC(=O)NHR$^{18}$, NHC(=S)NHR$^{18}$ and a bond to $L_n$;

$R^{18}$ is independently selected at each occurrence from the group: H, $C_1$–$C_6$ alkyl, benzyl, phenyl and a bond to $L_n$;

$L_n$ is a linking group of formula:

$$L^1-[Y^1(CR^{19}R^{20})_f(Z^1)_{f'}Y^2]_{f''}-L^2,$$

wherein:
$L^1$ is —[(CH$_2$)$_g$Z$^1$]$_{g'}$—(CR$^{19}$R$^{20}$)$_{g''}$—;
$L^2$ is —(CR$^{19}$R$^{20}$)$_{g''}$—[Z$^1$(CH$_2$)$_g$]$_{g'}$—;
g is independently 0–10;
g' is independently 0–1;
g'' is independently 0–10;
f is independently 0–10;
f' is independently 0–10;
f'' is independently 0–1;

$Y^1$ and $Y^2$, at each occurrence, are independently selected from the group: a bond, O, NR$^{20}$, C=O, C(=O)O, OC(=O)O, C(=O)NH—, C=NR$^{20}$, S, SO, SO$_2$, NHC(=O), (NH)$_2$C(=O) and (NH)$_2$C=S;

$R^{19}$ and $R^{20}$ are independently selected at each occurrence from the group: H, $C_1$–$C_{10}$ alkyl substituted with 0–5 $R^{21}$, and alkaryl wherein the aryl is substituted with 0–5 $R^{21}$;

$R^{21}$ is independently selected at each occurrence from the group: NHR$^{22}$, C(=O)R$^{22}$, OC(=O)R$^{22}$, OC(=O)OR$^{22}$, C(=O)OR$^{22}$, C(=O)NR$_2^{22}$, —CN, SR$^{22}$, SOR$^{22}$, SO$_2$R$^{22}$, NHC(=O)R$^{22}$, NHC(=O)NHR$^{22}$, NHC(=S)NHR$^{22}$ and a bond to W;

$R^{22}$ is independently selected at each occurrence from the group: H, $C_1$–$C_6$ alkyl, benzyl, phenyl and a bond to W; and W is a biologically active molecule selected from the group: IIb/IIIa receptor ligands, fibrin binding peptides, leukocyte binding peptides, chemotactic peptides, somatostatin analogs, selectin binding peptides, vitronectin receptor antagonists and tyrosine kinase inhibitors.

[21] Another embodiment of the present invention is a conjugate of embodiment [20], wherein:

X is selected from the group: NR$^{18}$, PR$^9$ and P(=O)R$^9$;
A is CH$_2$;
$R^8$ is selected from the group: OR$^{23}$, OR$^{14}$, C(=O)R$^{14}$ and S(=O)$_2$R$^{184}$;
$R^9$ is CH$_2$NR$^{15}$R$^{16}$;
g is independently 0–5;
g'' is independently 0–5;
f is independently 0–5;
f' is independently 0–5;
$Y^1$ and $Y^2$, at each occurrence, are independently selected from the group: a bond, O, NR$^{20}$, C=O, C(=O)O, OC(=O)O, C(=O)NH—, SO, SO$_2$, NHC(=O), (NH)$_2$C(=O) and (NH)$_2$C=S; and $R^{21}$ is independently selected at each occurrence from the group: NHR$^{22}$, C(=O)R$^{22}$, OC(=O)R$^{22}$, OC(=O)OR$^{22}$, C(=O)OR$^{22}$, C(=O)NR$_2^{22}$, SO$_2$R$^{22}$, NHC(=O)R$^{22}$, NHC(=O)NHR$^{22}$, NHC(=S)NHR$^{22}$ and a bond to W.

[22] Another embodiment of the present invention is a conjugate of embodiment [21], wherein:

X is P(=O)OH;

A is $CH_2$;

$Q^1$, $Q^2$, and $Q^3$ are independently —$(CR^{11}R^{12})_n$—, wherein: n is 2 or 3;

$R^{11}$ and $R^{12}$ are independently selected from the group: H, $C_1$–$C_5$ alkyl substituted with 0–3 $R^{17}$ and aryl substituted with 0–1 $R^{17}$;

$R^{17}$ is independently selected at each occurrence from the group: H, OH, $NHR^{18}$, C(=O)$R^{18}$, OC(=O)$R^{18}$, OC(=O)O$R^{18}$, C(=O)O$R^{18}$, C(=O)N$R_2^{18}$, $PO_3R_2^{18}$, $SO_2R^{18}$, NHC(=O)$R^{18}$, NHC(=O)NH$R^{18}$ and NHC(=S)NH$R^{18}$; and $R^{18}$ is independently selected at each occurrence from the group: H and $C_1$–$C_3$ alkyl.

[23] Another embodiment of the present invention is a conjugate of embodiment 22, wherein:

$R^1$, $R^2$, $R^3$ and $R^4$ are independently selected at each occurrence from the group: H, $CH_2COOH$, $CH_2PO_3H_2$ and $CH_2$—heterocycle substituted with 0–3 $R^{13}$; and $R^{13}$ is independently selected at each occurrence from the group: H, OH, $NH_2$, COOH, $PO_3H_2$, $CH_2OH$, $CH_3$ and $SO_3H$.

[23a] Another embodiment of the present invention is a conjugate of embodiment 22, wherein:

$R^{13}$ is independently selected at each occurrence from the group: $OR^{23}$, $OC(=O)OR^{23}$, $C(=O)OR^{23}$, $PO_3R^{18}R^{23}$, $SR^{23}$, $SOR^{23}$, $SO_2R^{23}$, and $CH_2OR^{23}$.

[24] Another embodiment of the present invention is a conjugate of embodiment [23], wherein:

$C_h$ is selected from the group:

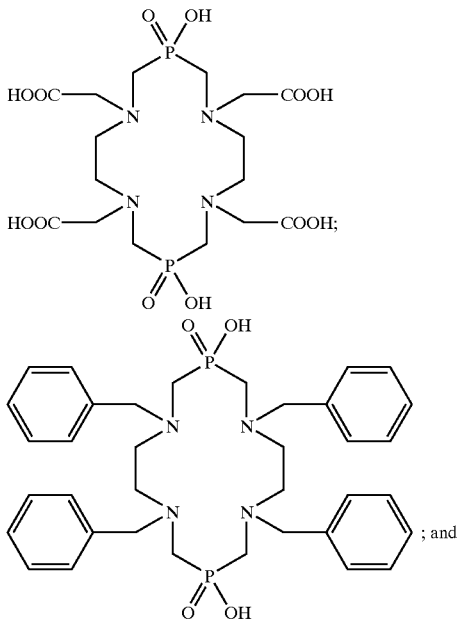

; and

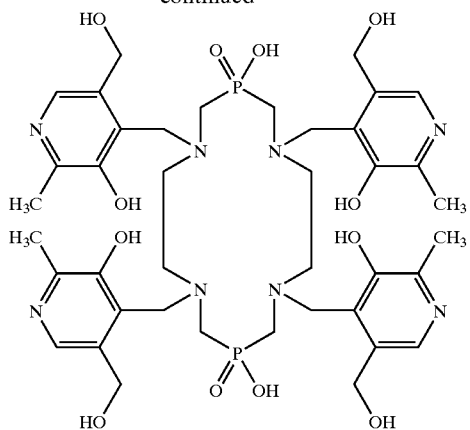

[25] Another embodiment of the present invention is a radiopharmaceutical of the formula:

M—$C_h$—$L_n$—W, and pharmaceutically acceptable salts thereof, wherein:

M is selected from the group: $^{64}Cu$, $^{67}Cu$, $^{67}Ga$, $^{68}Ga$, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$ and $^{188}Re$;

$C_h$ is a chelator of formulae (IX) or (X):

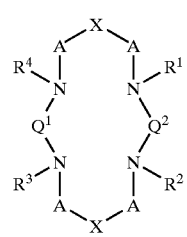
(IX)

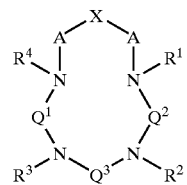
(X)

wherein:

$R^1$, $R^2$, $R^3$ and $R^4$ are independently selected at each occurrence from the group: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently elected at each occurrence from the group: H, C(=O)$OR^{18}$, C(=O)$OR^{23}$, $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is selected from the group: $BR^6R^7$, C(=O), $SiR^6R^7$, $GeR^6R^7$, $SnR^6R^7$, $NR^8$, $PR^9$, P(=O)$R^9$, P(=S)$R^9$, $AsR^9$ and As(=O)$R^9$;

A is selected from the group: $CH_2$, $NR^{10}$ and O;

$Q_1$, $Q^2$, and $Q^3$ are independently —$(CR^{11}R^{12})_n$—, wherein: n is 2–5;

$R^6$ and $R^7$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or alternatively, $R^6$ and $R^7$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^8$ is selected from the group: $OR^{23}$, $OR^{14}$, $C(=O)R^{14}$, $S(=O)_2R^{14}$ and $P(=O)(OR^{14})$;

$R^9$ is selected from the group: $OR^{14}$, $NR^{15}R^{16}$ and $CH_2NR^{15}R^{16}$;

$R^{10}$, $R^{11}$ and $R^{12}$ are independently selected from the group: H, $C_1$–$C_{10}$ alkyl substituted with 0–5 $R^{17}$, $C_2$–$C_{10}$ alkenyl substituted with 0–5 $R^{17}$ and aryl substituted with 0–3 $R^{17}$;

$R^{13}$ is independently selected at each occurrence from the group: H, OH $OR^{23}$, $NHR^{18}$, $C(=O)R^{18}$, $OC(=O)OR^{23}$, $OC(=O)R^{18}$, $C(=O)OR^{23}$, $OC(=O)OR^{18}$, $C(=O)OR^{18}$, $C(=O)NR_2^{18}$, $PO_3R_2^{18}$, $PO_3R^{18}R^{23}$, $SR^{18}$, $SR^{23}$, $SOR^{18}$, $SO_2R^{18}$, $SOR^{23}$, $SO_2R^{23}$, $NHC(=O)R^{18}$, $NHC(=O)NHR^{18}$, $CH_2OR^{18}$, $CH_2OR^{23}$, $CH_3$, $NHC(=S)NHR^{18}$ and a bond to $L_n$;

$R^{14}$, $R^{15}$ and $R^{16}$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SR^{18}$, $SOR^{18}$, $SO_2R^{18}$, $NHC(=O)R^{18}$, $NHC(=O)NHR^{18}$, $NHC(=S)NHR^{18}$ and a bond to $L_n$;

$R^{18}$ is independently selected at each occurrence from the group: H, $C_1$–$C_6$ alkyl, benzyl, phenyl and a bond to $L_n$;

$R^{23}$ is a bond to the metal M;

$L_n$ is a linking group of formula:

$$L^1-[Y^1(CR^{19}R^{20})_f(Z^1)_{f'}Y^2]_{f''}-L^2,$$

wherein:

$L^1$ is $-[(CH_2)_gZ^1]_{g'}-_{(CR}{}^{19}R^{20})_{g''}-$, $L^2$ is $-(CR^{19}R^{20})_{g''}-[Z^1(CH_2)_g]_{g'}-$;

g is independently 0–10;

g' is independently 0–1;

g" is independently 0–10;

f is independently 0–10;

f' is independently 0–10;

f" is independently 0–1;

$Y^1$ and $Y^2$, at each occurrence, are independently selected from the group: a bond, O, $NR^{20}$, $C=O$, $C(=O)O$, $OC(=O)O$, $C(=O)NH$—, $C=NR^{20}$, S, SO, $SO_2$, $NHC(=O)$, $(NH)_2C(=O)$ and $(NH)_2C=S$;

$R^{19}$ and $R^{20}$ are independently selected at each occurrence from the group: H, $C_1$–$C_{10}$ alkyl substituted with 0–5 $R^{21}$ and alkaryl wherein the aryl is substituted with 0–5 $R^{21}$;

$R^{21}$ is independently selected at each occurrence from the group: $NHR^{22}$, $C(=O)R^{22}$, $OC(=O)R^{22}$, $OC(=O)OR^{22}$, $C(=O)OR^{22}$, $C(=O)NR_2^{22}$, -CN, $SR^{22}$, $SOR^{22}$, $SO_2R^{22}$, $NHC(=O)R^{22}$, $NHC(=O)NHR^{22}$, $NHC(=S)NHR^{22}$ and a bond to W;

$R^{22}$ is independently selected at each occurrence from the group: H, $C_1$–$C_6$ alkyl, benzyl, phenyl and a bond to W; and W is a biologically active molecule selected from the group: IIb/IIIa receptor ligands, fibrin binding peptides, leukocyte binding peptides, chemotactic peptides, somatostatin analogs, selectin binding peptides, vitronectin receptor antagonists and tyrosine kinase inhibitors.

[26] Another embodiment of the present invention is a conjugate of embodiment [25], wherein:

X is selected from the group: $NR^8$, $PR^9$ and $P(=O)R^9$;

A is $CH_2$;

$R^8$ is selected from the group: $OR^{23}$, $OR^{14}$, $C(=O)R^{14}$ and $S(=O)_2R^{14}$;

$R^9$ is $CH_2NR^{15}R^{16}$;

g is independently 0–5;

g" is independently 0–5;

f is independently 0–5;

f' is independently 0–5;

$Y^1$ and $Y^2$ at each occurrence, are independently selected from the group: a bond, O, $NR^{20}$, $C=O$, $C(=O)O$, $OC(=O)O$, $C(=O)NH$—, SO, $SO_2$, $NHC(=O)$, $(NH)_2C(=O)$ and $(NH)_2C=S$; and $R^{21}$ is independently selected at each occurrence from the group: $NHR^{22}$, $C(=O)R^{22}$, $OC(=O)R^{22}$, $OC(=O)OR^{22}$, $C(=O)OR^{22}$, $C(=O)NR_2^{22}$, $SO_2R^{22}$, $NHC(=O)R^{22}$, $NHC(=O)NHR^{22}$, $NHC(=S)NHR^{22}$ and a bond to W.

[27] Another embodiment of the present invention is a conjugate of embodiment [26], wherein:

X is $P(=O)OH$;

A is $CH_2$;

$Q^1$, $Q^2$, and $Q^3$ are independently $-(CR^{11}R^{12})_n-$, wherein n is 2 or 3;

$R^{11}$ and $R^{12}$ are independently selected from the group: H, $C_1$–$C_5$ alkyl substituted with 0–3 $R^{17}$ and aryl substituted with 0–1 $R^{17}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SO_2R^{18}$, $NHC(=O)R^{18}$, $NHC(=O)NHR^{18}$ and $NHC(=S)NHR^{18}$; and $R^{18}$ is independently selected at each occurrence from the group: H and $C_1$–$C_3$ alkyl.

[28] Another embodiment of the present invention is a conjugate of embodiment [27], wherein:

$R^1$, $R^2$, $R^3$ and $R^4$ are independently selected at each occurrence from the group: H, $CH_2COOH$, $CH_2PO_3H_2$ and $CH_2$—heterocycle substituted with 0–3 $R^{13}$; and $R^{13}$ is independently selected at each occurrence from the group: H, $OR^{23}$, $OC(O)OR^{23}$, $C(O)OR^{23}$, $PO_3R^{18}R^{23}$, $SR^{23}$, $SOR^{23}$, $SO_2R^{23}$, $CH_2OR^{23}$, OH, $NH_2$, COOH, $PO_3H_2$, $CH_2OH$, CH3 and $SO_3H$.

[29] Another embodiment of the present invention is a conjugate of embodiment [28], wherein:

$C_h$ is selected from the group:

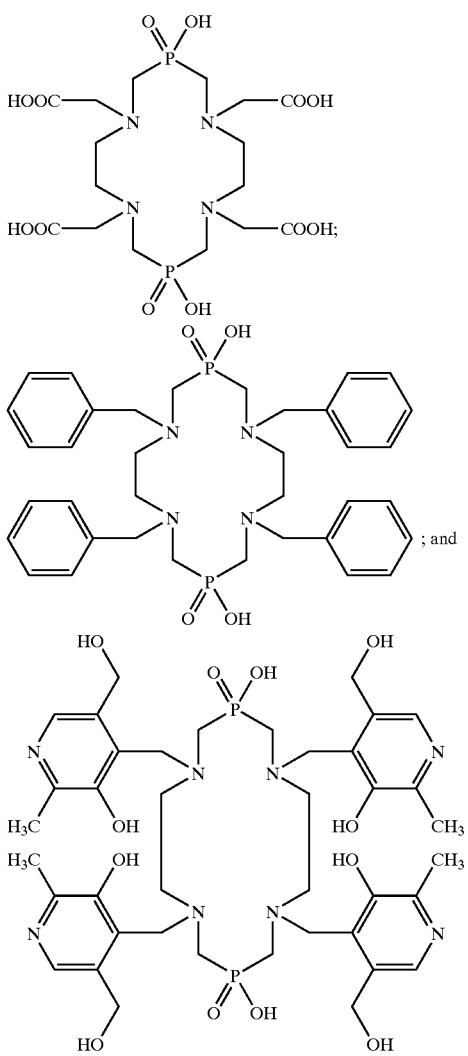
; and

[30] Another embodiment of the present invention is a radiopharmaceutical of the formula:

$$M—C_h—L_n—W,$$

and pharmaceutically acceptable salt thereof, wherein:

M is a paramagnetic metal ion of atomic number selected from the group: 21–29, 42–44 and 58–70;

$C_h$ is a chelator of formulae (XI) or (XII):

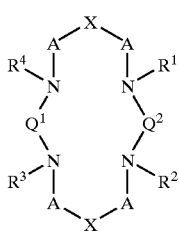
(XI)

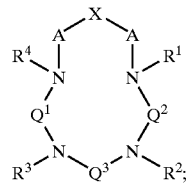
(XII)

wherein:
$R^1$, $R^2$, $R^3$ and $R^4$ are independently selected at each occurrence from the group: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently elected at each occurrence from the group: H, C(=O)OR$^{18}$, C(=O)OR$^{23}$, $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is is selected from the group: BR$^6$R$^7$, C(=O), SiR$^6$R$^7$, GeR$^6$R$^7$, SnR$^6$R$^7$, NR$^8$, PR$^9$, P(=O)R$^9$, P(=S)R$^9$, AsR$^9$ and As(=O)R$^9$;

A is selected from the group: CH$_2$, NR$^{10}$ and O;

$Q^1$, $Q^2$, and $Q^3$ are independently —(CR$^{11}$R$^{12}$)$_n$—, wherein: n is 2–5;

$R^6$ and $R^7$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or alternatively, $R^6$ and $R^7$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^8$ is selected from the group: OR$^{23}$, OR$^{14}$, C(=O)R$^{14}$, S(=O)$_2$R$^{14}$ and P(=O)(OR$^{14}$);

$R^9$ is selected from the group: OR$^{14}$, NR$^{15}$R$^{16}$ and CH$_2$NR$^{15}$R$^{16}$;

$R^{10}$, $R^{11}$ and $R^{12}$ are independently selected from the group: H, $C_1$–$C_{10}$ alkyl substituted with 0–5 $R^{17}$, $C_2$–$C_{10}$ alkenyl substituted with 0–5 $R^{17}$ and aryl substituted with 0–3 $R^{17}$;

$R^{18}$ is independently selected at each occurrence from the group: H, OH, OR$^{23}$, NHR$^{18}$, C(=O)R$^{18}$, OC(O)R$^{18}$, OC(=O)OR$^{18}$, OC(=O)OR$^{23}$, C(=O)OR$^{18}$, C(=O)OR$^{23}$, C(=O)NR$_2^{18}$, PO$_3$R$_2^{18}$, PO$_3$R$^{18}$R$^{23}$, SR$^{18}$, SR$^{23}$, SOR$^{18}$, SO$_2$, SR$^{18}$, SOR$^{23}$, SO$_2$R$^{23}$, NHC(=O)R$^{18}$, NHC(=O)NHR$^{18}$, CH$_2$OR$^{18}$, CH$_2$OR$^{23}$, CH$_3$, NHC(=S)NHR$^{18}$ and a bond to $L_n$;

$R^{14}$, $R^{15}$ and $R^{16}$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{123}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, NHR$^{18}$, C(=O)R$^{18}$, OC(=O) R$^{18}$, OC(=O)OR$^{18}$, C(=O)OR$^{18}$, C(=O)NR$_2^{18}$, PO$_3$R$_2^{18}$, SR$^{18}$, SOR$^{18}$, SO$_2$R$^{18}$, NHC(=O)R$^{18}$, NHC(=O)NHR$^{18}$, NHC(=S)NHR$^{18}$ and a bond to $L_n$;

$R^{18}$ is independently selected at each occurrence from the group: H, $C_1$–$C_6$ alkyl, benzyl, phenyl and a bond to $L_n$;

$R^{23}$ is a bond to the metal M;

$L_n$ is a linking group of formula:

$$L^1-[Y^1(CR^{19}R^{20})_f(Z^1)_{f'}Y^2]_{f''}-L^2,$$

wherein:

$L^1$ is $-[(CH_2)_g Z^1]_{g'}-(CR^{19}R^{20})_{g''}-$;

$L^2$ is $-(CR^{19}R^{20})_{g''}-[Z^1(CH_2)_g]_{g'}-$;

g is independently 0–10;

g' is independently 0–1;

g" is independently 0–10;

f is independently 0–10;

f' is independently 0–10;

f" is independently 0–1;

$Y^1$ and $Y^2$, at each occurrence, are independently selected from the group: a bond, O, $NR^{20}$, C=O, C(=O)O, OC(=O)O, C(=O)NH—, C=$NR^{20}$, S, SO, SO2t NHC(=O), $(NH)_2C(=O)$ and $(NH)_2C=S$;

$R^{19}$ and $R^{20}$ are independently selected at each occurrence from the group: H, $C_1$–$C_{10}$ alkyl substituted with 0–5 $R^{21}$ and alkaryl wherein the aryl is substituted with 0–5 $R^{21}$;

$R^{21}$ is independently selected at each occurrence from the group: $NHR^{22}$, C(=O)$R^{22}$, OC(=O)$R^{22}$, OC(=O)O$R^{22}$, C(=O)O$R^{22}$, C(=O)$NR_2^{22}$, —CN, S$R^{22}$, SO$R^{22}$, $SO_2R^{22}$, NHC(=O)$R^{22}$, NHC(=O)NH$R^{22}$, NHC(=S)NH$R^{22}$ and a bond to W;

$R^{22}$ is independently selected at each occurrence from the group: H, $C_1$–$C_6$ alkyl, benzyl, phenyl and a bond to W; and W is a biologically active molecule selected from the group: IIb/IIIa receptor ligands, fibrin binding peptides, leukocyte binding peptides, chemotactic peptides, somatostatin analogs, selectin binding peptides, vitronectin receptor antagonists and tyrosine kinase inhibitors.

[31] Another embodiment of the present invention is a conjugate of embodiment [30], wherein:

X is selected from the group: $NR^8$, $PR^9$ and P(=O)$R^9$;

A is $CH_2$;

$R^8$ is selected from the group: $OR^{23}$, $OR^{14}$, C(=O)$R^{14}$ and S(=O)$_2R^{14}$;

$R^9$ is $CH_2NR^{15}R^{16}$;

g is independently 0–5;

g" is independently 0–5;

f is independently 0–5;

f' is independently 0–5;

$Y^1$ and $Y^2$, at each occurrence, are independently selected from the group: a bond, O, $NR^{20}$, C=O, C(=O)O, OC(=O)O, C(=O)NH—, SO, $SO_2$, NHC(=O), $(NH)_2C(=O)$ and $(NH)_2C=S$; and $R^{21}$ is independently selected at each occurrence from the group: $NHR^{22}$, C(=O)$R^{22}$, OC(=O)$R^{22}$, OC(=O)O$R^{22}$, C(=O)O$R^{22}$, C(=O)$NR_2^{22}$, $SO^2R^{22}$, NHC(=O)$R^{22}$, NHC(=O)NH$R^{22}$, NHC(=S)NH$R^{22}$ and a bond to W.

[32] Another embodiment of the present invention is a conjugate of embodiment [31], wherein:

X is P(=O)OH;

A is $CH_2$;

$Q^1$, $Q^2$, and $Q^3$ are independently $-(CR^{11}R^{12})_n-$, wherein: n is 2 or 3;

$R^{11}$ and $R^{12}$ are independently chosen from the group: H, $C_1$–$C_5$ alkyl substituted with 0–3 $R^{17}$ and aryl substituted with 0–1 $R^{17}$;

$R^{17}$ is independently selected at each occurrence from the group: H, OH, $NHR^{18}$, C(=O)$R^{18}$, OC(=O)$R^{18}$, OC(=O)O$R^{18}$, C(=O)O$R^{18}$, C(=O)$NR_2^{18}$, $PO_3R_2^{18}$, $SO_2R^{18}$, NHC(=O)$R^{18}$, NHC(=O)NH$R^{18}$ and NHC(=S)NH$R^{18}$; and $R^{18}$ is independently selected at each occurrence from the group: H and $C_1$–$C_3$ alkyl.

[33] Another embodiment of the present invention is a conjugate of embodiment [32], wherein:

$R^1$, $R^2$, and $R^3$ are independently selected at each occurrence from the group: H, $CH_2COOH$, $CH_2PO_3H_2$ and $CH_2$—heterocycle substituted with 0–3 $R^{13}$; and $R^{13}$ is independently selected at each occurrence from the group: H, OH, $NH_2$, COOH, $PO_3H_2$, $CH_2OH$, $CH_3$ and $SO_3H$.

[33a] Another embodiment of the present invention is a conjugate of embodiment [32], wherein:

R13 is independently selected at each occurrence from the group: H, $OR^{23}$, OC(O)O$R^{23}$, C(=O)O$R^{23}$, $PO_3R^{18}R^{23}$, $SR^{23}$, $SOR^{23}$, $SO_3R^{23}$, $CH_2OR^{23}$, OH, $NH_2$, COOH, $PO_3H_2$, $CH_2OH$, CH3 and $SO_3H$.

[34] Another embodiment of the present invention is a conjugate of embodiment [33], wherein:

$C_h$ is selected from the group:

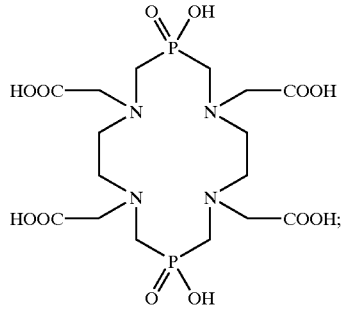

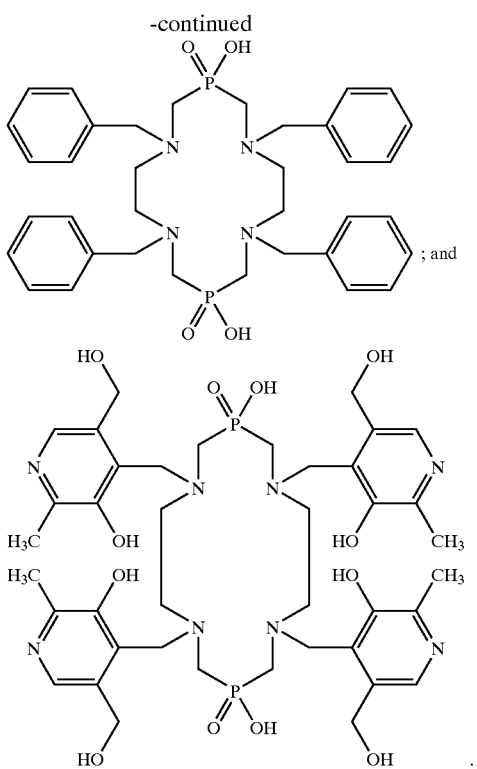

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention.

The term "substituted," as used herein, means that any one or more hydrogens on the designated atom is replaced with a selection from the indicated group, provided that the designated atom's normal valency is not exceeded, and that the substitution results in a stable compound. When a substitent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R^9$) occurs more than one time in any constituent or formula for a compound, its definition at each occurrence is independent of its definition at every other occurrence. Thus, for example, if a group is shown to be substituted with 0-2 $R^9$, then said group may optionally be substituted with up to two $R^9$ groups and $R^9$ at each occurrence is selected independently from the definition of $R^9$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. "Alkenyl" is intended to include hydrocarbon chains of either a straight or branched configuration and one or more unsaturated carbon-carbon bonds which may occur in any stable point along the chain, such as ethenyl and propenyl. "Alkynyl" is intended to include hydrocarbon chains of either a straight or branched configuration and one or more triple carbon-carbon bonds which may occur in any stable point along the chain, such as ethynyl and propynyl.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5- to 7-membered monocyclic or bicyclic or 7- to 10-membered bicyclic heterocyclic ring which is saturated partially unsaturated or unsaturated (aromatic), and which consists of carbon atoms and from 1 to 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heterotams independently selected from the group consisting of NO and S. It is preferred that the total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro [2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2, 3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrrolidinyl, imidazolyl, indolyl, benzimidazolyl, 1H-indazolyl, oxazolidinyl, benzotriazolyl, benzisoxazolyl, oxindolyl, benzoxazolinyl, and isatinoyl. Also included are fused ring and spiro compounds containing, for example, the above heterocycles.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342–429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, norleucine, N-methylaminobutyric acid, naphthylalanine, phenylglycine, β-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "peptide" as used herein means a linear compound that consists of two or more amino acids (as defined herein) that are linked by means of a peptide bond. A "peptide" as used in the presently claimed invention is intended. to refer to a moiety with a molecular weight of less than 10,000 Daltons, preferable less than 5,000 Daltons, and more preferably less than 2,500 Daltons. The term "peptide" also includes compounds containing both peptide and non-peptide components, such as pseudopeptide or peptidomimetic residues or other non-amino acid components. Such a compound containing both peptide and non-peptide components may also be referred to as a "peptide analog".

A "pseudopeptide" or "peptidomimetic" is a compound which mimics the structure of an amino acid residue or a peptide, for example, by using linking groups other than amide linkages between the peptide mimetic and an amino acid residue (pseudopeptide bonds) and/or by using non-amino acid substituents and/or a modified amino acid residue. A "pseudopeptide residue" means that portion of an pseudopeptide or peptidomimetic that is present in a peptide.

The term "peptide bond" means a covalent amide linkage formed by loss of a molecule of water between the carboxyl group of one amino acid and the amino group of a second amino acid.

The term "pseudopeptide bonds" includes peptide bond isosteres which may be used in place of or as substitutes for the normal amide linkage. These substitute or amide "equivalent" linkages are formed from combinations of atoms not normally found in peptides or proteins which mimic the spatial requirements of the amide bond and which should stabilize the molecule to enzymatic degradation.

The term "non-peptide" refers to a compound in comprised of preferably less than three amide bonds in the backbone core compound or preferably less than three amino acids or amino acid mimetics.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

Since prodrugs are known to enhance numerous desirable qualities of pharmaceuticals (e.g., solubility, bioavailability, manufacturing) the compounds of the present invention may be delivered in prodrug form. Thus, the present invention is intended to cover prodrugs of the presently claimed compounds, methods of delivering the same and compositions containing the same. "Prodrugs" are intended to include any covalently bonded carriers which release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate and benzoate derivatives of alcohol and amine functional groups in the compounds of the present invention.

"Stable compound" and "stable structure" are meant to indicate a compound that is sufficiently robust to survive isolation to a useful degree of purity from a reaction mixture, and formulation into an efficacious therapeutic agent.

The coordination sphere of the radionuclide includes all the ligands or groups bound to the radionuclide. For a transition metal radionuclide, M, to be stable it typically has a coordination number (number of donor atoms) comprised of an integer greater than or equal to 4 and less than or equal to 9; that is there are 4 to 9 atoms bound to the metal and it is said to have a complete coordination sphere. The requisite coordination number for a stable radionuclide complex is determined by the identity of the radionuclide, its oxidation state, and the type of donor atoms. If the chelant does not provide all of the atoms necessary to stabilize the metal radionuclide by completing its coordination sphere, the coordination sphere is completed by donor atoms from other ligands, termed ancillary or co-ligands, which can also be either terminal or chelating.

Lyophilization aids useful in the preparation of diagnostic kits useful for the preparation of radiopharmaceuticals include but are not limited to mannitol, lactose, sorbitol, dextran, Ficoll, and polyvinylpyrrolidine (PVP).

Stabilization aids useful in the preparation of radiopharmaceuticals and in diagnostic kits useful for the preparation of said radiopharmaceuticals include but are not limited to ascorbic acid, cysteine, monothioglycerol, sodium bisulfite, sodium metabisulfite, gentisic acid, and inositol.

Solubilization aids useful in the preparation of radiopharmaceuticals and in diagnostic kits useful for the preparation of said radiopharmaceuticals include but are not limited to ethanol, glycerin, polyethylene glycol, propylene glycol, polyoxyethylene sorbitan monooleate, sorbitan monoloeate, polysorbates, poly(oxyethylene)poly(oxypropylene)poly(oxyethylene) block copolymers (Pluronics) and lecithin. Preferred solubilizing aids are polyethylene glycol, and Pluronics.

Bacteriostats useful in the preparation of radiopharmaceuticals and in diagnostic kits useful for the preparation of said radiopharmaceuticals include but are not limited to benzyl alcohol, benzalkonium chloride, chiorbutanol, and methyl, propyl or butyl paraben.

SYNTHESIS OF NEW MACROCYCLES

Macrocyclic Chelants with Phosphinic Acid Bridges

Organophosphinic acids are organic derivatives of phosphinic acid ($H_2PO_2H$) in which one or both of the hydrogen atoms on the phosphorus atoms are replaced by organic groups. In general, the P—C bonds are very stable to hydrolysis, oxidation, and thermal decomposition. It is known that phosphinic acid undergoes Mannich reactions with primary or secondary amines in the presence of excess paraformaldehyde under strong acidic conditions (Maier, L. and Smith, M. J. Phosphorus and Sulfur, 1980, 8, 67–72; Varga, T. R. Synthetic Communication, 1997, 27, 2899–2903). In the present invention, phosphinic acid is reacted with a secondary diamine in the presence of formaldehyde to form a new macrocyclic chelant containing two phosphinic acid bridges. For example, TETA(PO)$_2$ was prepared by the reaction of phosphinic acid with one equivalent of ethylenediamine-N,N'-diacetic acid (EDDA) in the presence of excess paraformaldehyde in 6 N HCl at 105–110° C. (Scheme I). For successful cyclization, high dilution is preferred.

Scheme I.
Mannich Reaction of Phosphinic Acid with Secondary Diamine and Formaldehyde

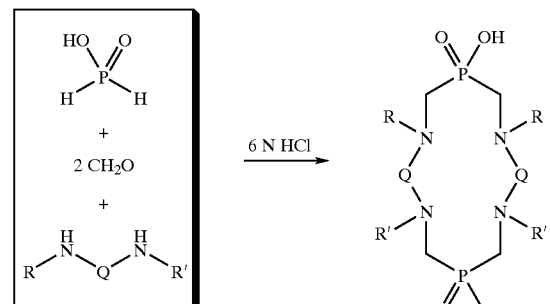

Q = Q¹ and Q²; R and R' = R¹, R², R³, and R⁴

Scheme II.
Mannich Reaction of Bis(hydroxymethyl)phosphine with Secondary Diamine

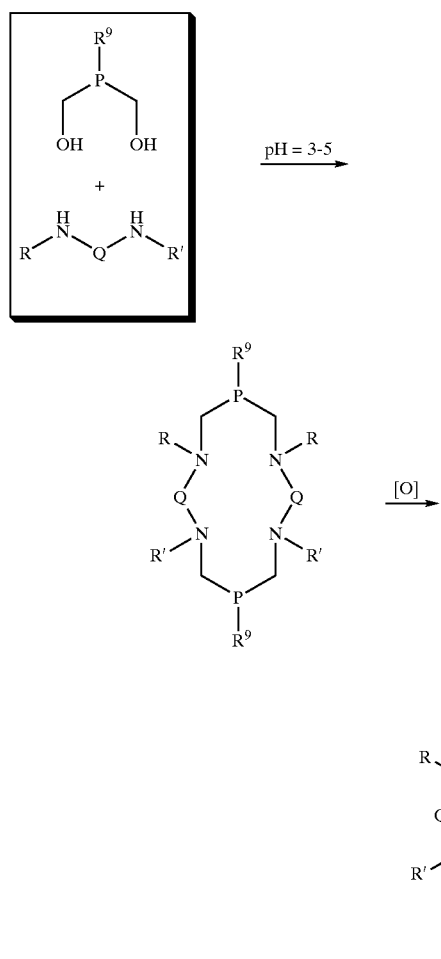

Q = Q¹ and Q²; R and R' = R¹, R², R³, and R⁴.

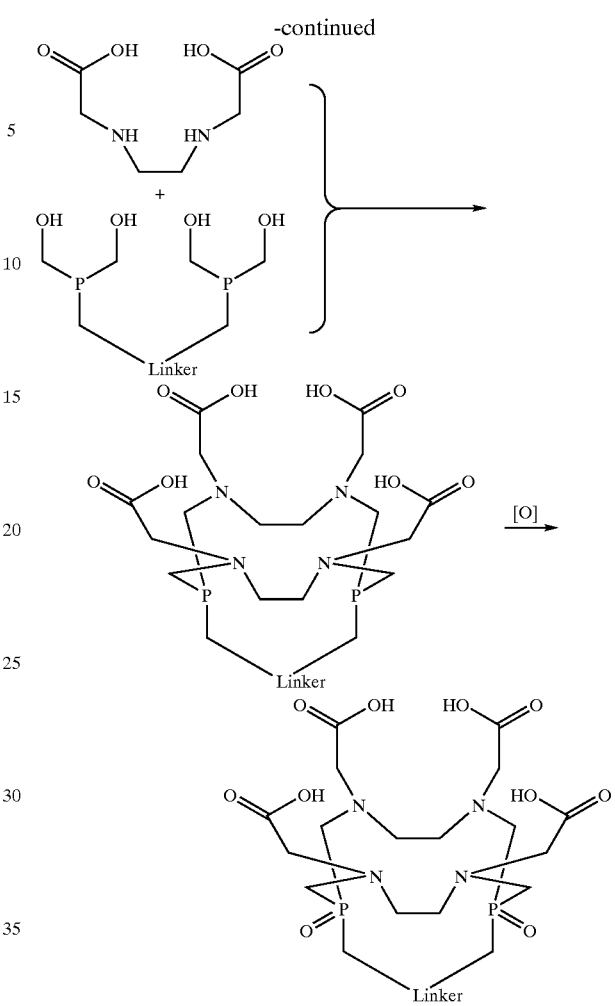

Macrocyclic Chelants Containing Two Phosphine-P or PhosThine-Oxo Bridges

It is known that hydroxymethyl-phosophines undergo the Mannich reactions with primary and secondary amines (Märkl, V. G., et al. Tetrhedron Letters, 1980, 21, 1409–1412). Mannich reactions have been extensively reviewed (Tramotini, M. and Angiolini, L. Tetrahedron, 1990, 1791–1823; Tramotini, M. SYNTHESIS, 1976, 703–775). Recently, the one-step Mannich reactions of hydroxymethylphosphines with a variety of amines, amino acids, and peptides (Katti, K. V. et al, J. Am. Chem. Soc. 1999, 121, 1658–1664) were reported. In the present invention, the Mannich reaction (Scheme II) of bis(hydroxymethyl)phosphine with one equivalent of a secondary diamine at pH 3–5 is used to produce new macrocyclic chelants containing two phosphine-containing bridges. Oxidation of the phosphine(III) atoms of these macrocyclic chelants will result in formation of new macrocyclic chelants containing two phosphine-oxo bridges. Macrocyclic chelants containing two phosphine-oxo bridges connected via a linker (Scheme II) are of particular interest because the linker between the two P atoms can force the tatraaza macrocycle to adopt a preorganized conformation for metal chelation, which will enhance the thermodynamic stability and kinetic inertness of their lanthanide metal complexes. The linker may also have a bifunctional group useful for attachment of biomolecules. Thus, they are useful as BFC's for the radiolabeling of biomolecules such as antibodies, peptides, peptidomimetics, and non-peptide receptor ligands.

Alternatively, these macrocyclic chelants can be prepared from a bicyclic intermediate (Scheme III), derived from the reaction of a diamine with glycoxal derivatives (Argese, M., et al U.S. Pat. No. 5,880,281 (1999)). Condensation of bis(hydroxymethyl)phosphine or bis(hydroxymethyl)arsine with the bicyclic intermediate will result in formation of a tetracyclic compound with the general formula shown in Scheme III. Oxidation and hydrolysis of the tetracyclic intermediate produces the corresponding tetraaza macrocycle, which reacts readily with alkyl halide (particularly alkyl bromide) in the presence of an excess base such as triethylamine to give the alkylated tetraaza macrocycle. The two substituents on the phosphine-oxo bridges may be connected via an alkyl or aryl linker (Scheme II). The linker may contain one or mare bifunctional group useful for attachment of biomolecules.

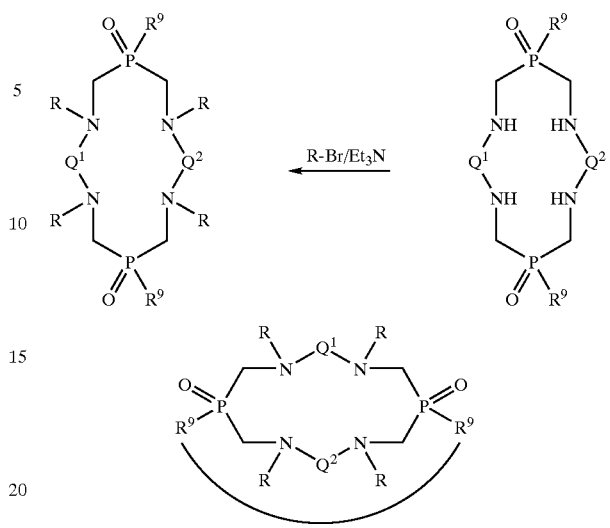

Scheme III.
Alternative Routes for Synthesis of Macrocyclic Chelants with Two Heteroatom-Containing Bridges.

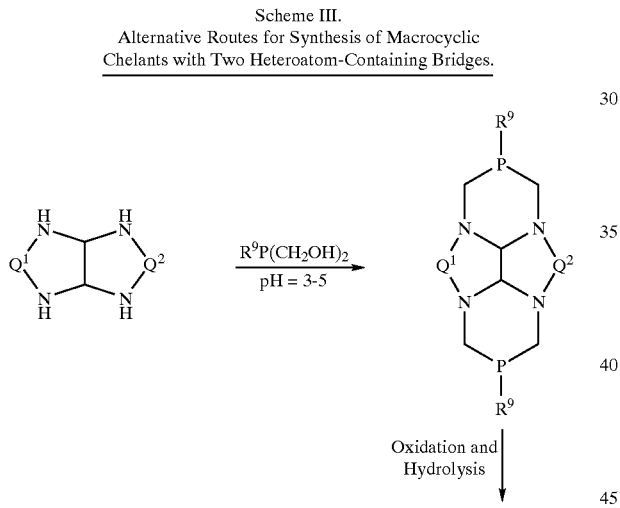

Scheme IV.
Synthesis of Hydroxyamine-Derivatized Macrocycles.

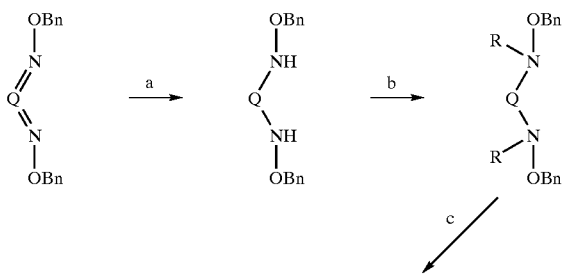

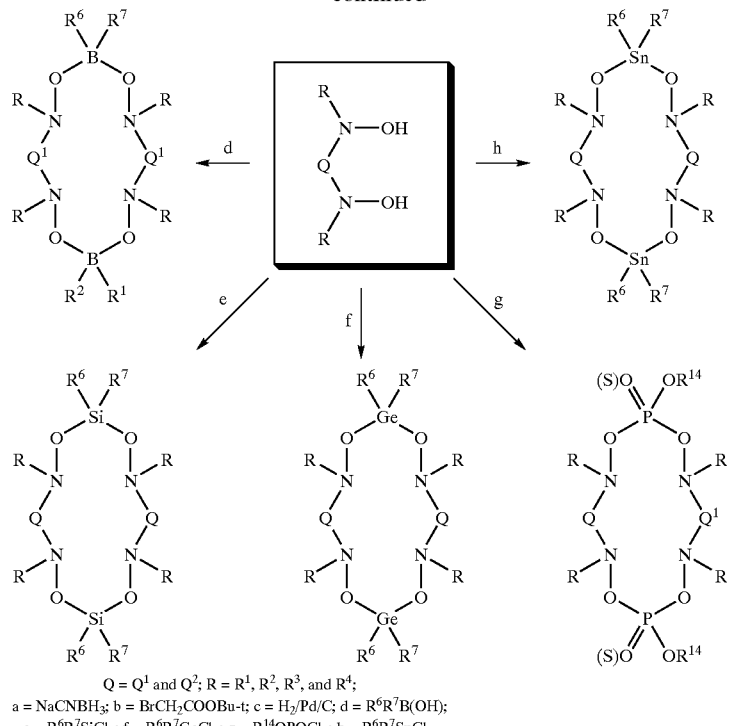

Q = Q¹ and Q²; R = R¹, R², R³, and R⁴;
a = NaCNBH₃; b = BrCH₂COOBu-t; c = H₂/Pd/C; d = R⁶R⁷B(OH);
e = R⁶R⁷SiCl₂; f = R⁶R⁷GeCl₂; g = R¹⁴OPOCl₂; h = R⁶R⁷SnCl₂.

Hydroxyamine-Derivatized Macrocylic Chelants

Macrocyclic chelants containing the hydroxyamine moiety are of interest because the hydroxyamine-O can form stable bonds with various heteroatoms such as B, Si, Ge, Sn, and P. Synthesis of these macrocyclic chelants involves several step reactions (Scheme IV). First, the O-benzyl protected hydroxyamine reacts with a dialdehyde or diketone to form the Schiff base, which can be readily reduced to give an O-benzyl protected bis-hydroxyamine. The bis-hydroxyamine reacts with t-butyl bromoacetate in the presence of a base such as triethylamine to produce the t-butyl ester of ethylenedi(benzyloxyamine)-N,N-diacetic acid. Deprotection of the O-benzyl groups is achieved by catalytic hydrogenation to give ethylenedi(hydroxyamine)-N,N-diacetic acid, which reacts with but not limited to substituted organoborate, organotin dichloride, organogermyl dichloride, thiophosphorodichloride or phosphorodichloride to produce the macrocyclic chelant as its t-butyl ester. Acid hydrolysis of the t-butyl ester produces the macrocyclic chelant in its acid form. The two substituents on the heteroatoms may contain one or more bifunctional groups useful for attachment of biomolecules.

Scheme V.
Synthesis of Hydrazine-Derivatized Macrocycles

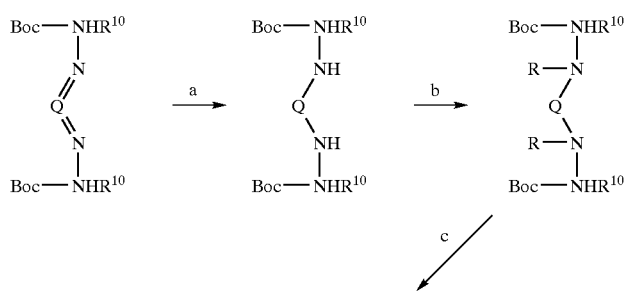

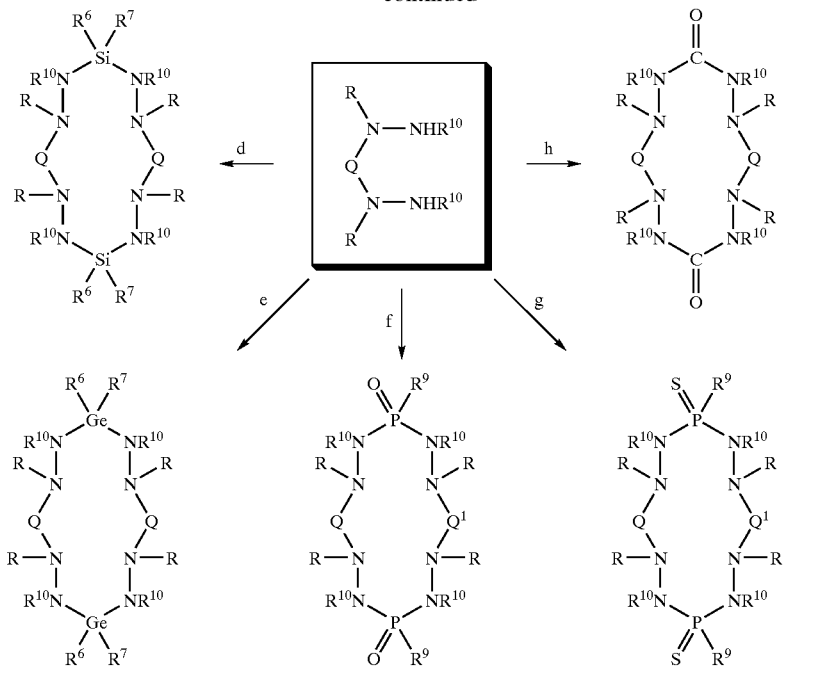

Q = Q$^1$ and Q$^2$; R = R$^1$, R$^2$, R$^3$, and R$^4$; a = NaCNBH$_3$; b = alkylbromide; c = H$^+$; d = R$^6$R$^7$SiCl$_2$; e = R$^6$R$^7$GeCl$_2$; f = R$^9$POCl$_2$; g = R$^9$PSCl$_2$; h = COCl$_2$.

Hydrazine-Derivatized Macrocyles

Synthesis of macrocyclic chelants containing the hydrazine moiety also involves several step reactions (Scheme V). First, the Boc-protected hydrazine reacts with a dialdehyde to form the hydrazone. Reduction of the hydrazone (Wu, P. L. et al, SYNTHESIS, 1995, 435–438; and references therein) to give the Boc-protected bis-hydrazine, which reacts with t-butyl bromoacetate to produce the t-butyl ester of N,N'-diaminoethylenediamine-N',N'-diacetic acid. Deprotection of the Boc group is achieved using either anhydrous TFA (trifluoroacetic acid) or a 50:50 mixture of TFA and dichloromethane to give N,N'-diaminoethylenediamine-N,N'-diacetic acid, which reacts with but not limited to substituted organotin dichloride, organogermyl dichloride, carbonyl dichloride, phosphorodichloride or thiophosphorodichloride to produce the macrocyclic chelant as its t-butyl tetraester. Acid hydrolysis of the tetraester gives the macrocyclic chelant in its acid form. The advantage of the hydrazine-containing bridges is that the substituents (R$^9$ groups) can be used for attachment of biomolecules.

Alternatively, synthesis of macrocyclic chelants containing the hydrazine moieties can be accomplished according to Scheme VI, which involves the formation of a cyclic hydrazone, reduction of the hydrazone double bonds (Wu, P. L. et al, SYNTHSIS, 1995, 435–438; and references therein), followed by the reaction with t-butyl bromoacetate, and the hydrolysis of the t-butyl ester groups. Macrocyclic chelants with the two bridging heteroatoms connected via a linker (R$^5$—R$^5$, R$^5$–R$^6$, R$^6$—R$^6$) are of special interest because the linker can force the tatraaza macrocycle to be highly preorganized for metal chelation. The linker may also contain a bifunctional group useful for attachment of biomolecules.

Scheme VI.
Alternative Route for Synthesis of Hydrazine-Derivatized Macrocycles.

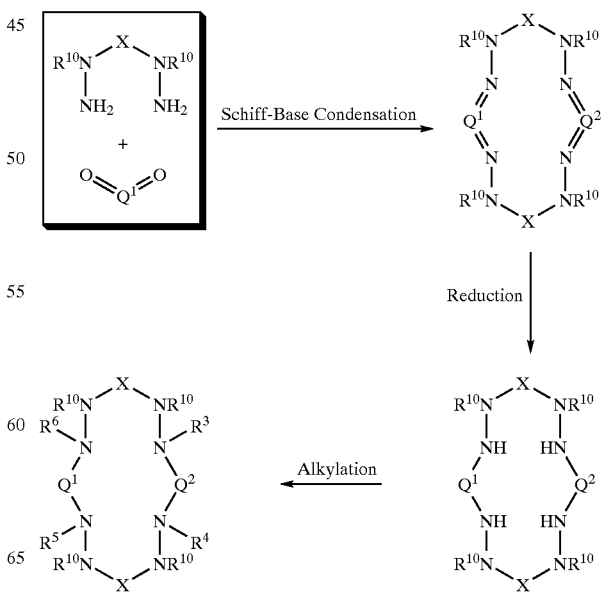

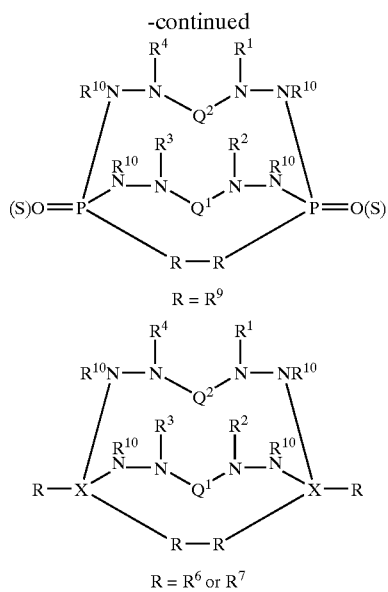

R = R⁹

R = R⁶ or R⁷

Macrocyclic Chelants with One Heteroatom-containing Bridge

The Mannich reaction is the condensation of a compound having active hydrogen atoms (the substrate) with formaldehyde and an amine:

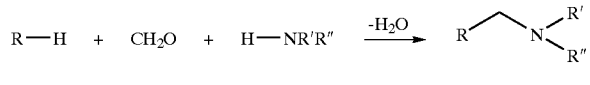

The structures of the products depend on the nature of the substrate as the amine moiety is the same as indicated in Scheme VII. The substrates include but are not limited to phosphinic acid, bis(hydroxymethyl)phosphine, bis-(hydroxymethyl)arsine, amide, sulfonamide, or N-containing heterocycle. Mannich reactions have been extensively reviewed (Tramotini, M. and Angiolini, L. Tetrahedron, 1990, 1791–1823; Tramotini, M. SYNTHESIS, 1976, 703–775).

Scheme VII.
Synthesis of Macrocyclic Chelants
with One Heteroatom-Bridge

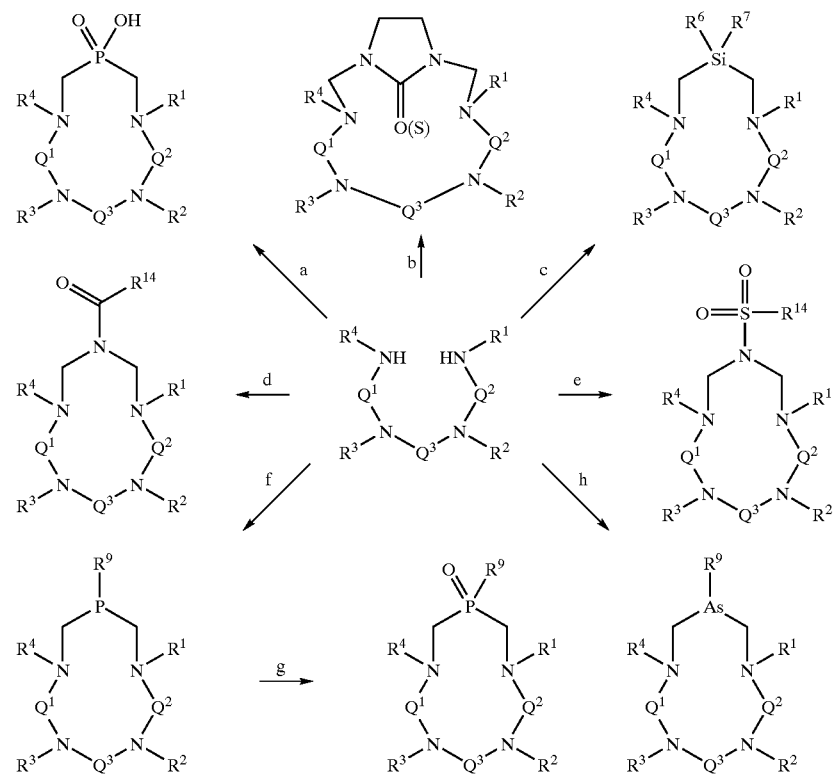

a = $H_2P(O)OH/CH_2O/6N$ HCl; b = $C_3H_2N_2O/CH_2O$;
c = $R^6R^7Si(CH_2Cl)_2$; d = $R^{14}$—$CONH_2/CH_2O$;
e = $R^{14}$—$SO_2NH_2/CH_2O$; f = Bis-hydroxymethylphoshine/pH = 3–5;
g = [O]; h = Bis-hydroxymethylarsine/pH = 3–5.

Scheme VII shows synthesis of some examples for tetraaza macrocyclic chelants with one heteroatom-containing bridge. The key intermediate contains two secondary amine-N atoms. Synthesis of the key intermediate can be achieved according to Scheme VIII. Like other secondary amines, N,N,N,N-substituted tetraamine is expected to undergo Mannich reactions with various substrates (Scheme VIII).

Scheme VIII.
Synthesis of 1,4,7,10-Tetraazadecane-1,4,7,10-tetraacetic acid (or its ester form).

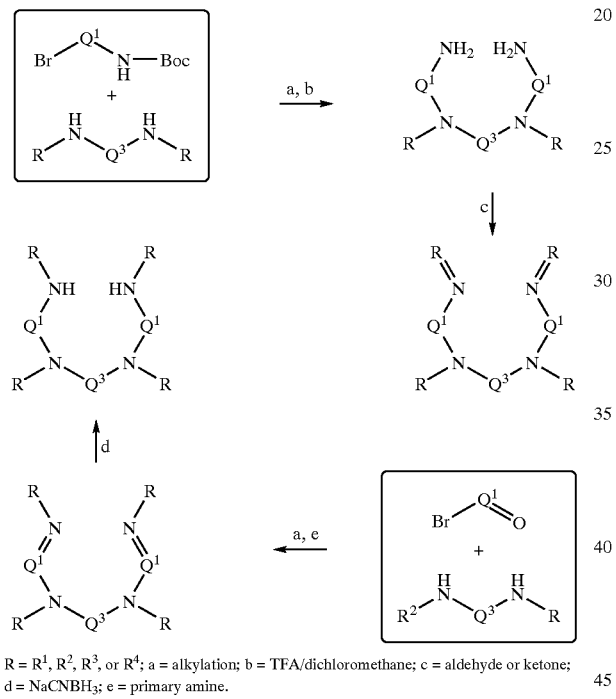

R = $R^1$, $R^2$, $R^3$, or $R^4$; a = alkylation; b = TFA/dichloromethane; c = aldehyde or ketone; d = NaCNBH$_3$; e = primary amine.

Macrocyclic chelants containing a silicon heteroatom can also be synthesized acoording to Scheme IX. First, 1,1'-(1,2-ethanediyl)-bis[4,5-dihydro-1H]-imidazoline, prepared by reacting triethylenetetraamine with dimethyl acetal in DMF (Athey, P. and Kimble, K. L. WO 95/14726). It is reacted with substituted bis(chloromethyl)silane in the presence of potassium carbonate to give the cyclized intermediate, which can be readily hydrolyzed under basic conditions to yield the macrocycle tetraamine. The macrocyclic tetraamine reacts with 4 equivalents of t-butyl acetate in the presence of a base such as triethylamine. Hydrolysis of the t-butyl tetraester produces the macrocyclic chelant in its free acid form. The substituents ($R^5$ and $R^6$ groups) on the silicon heteroatom may contain the functional moieties for attachment of biomolecules. One of the four actetate arms can also be used for attachment of biomolecules. Thus, these macrocyclic chelants are useful as BFC's for the radiolabeling of biomolecules.

Scheme IX.
Synthesis of 1,4,7,10-Tetraaza Macrocyclic Chelants with A Silicone Heteroatom-Bridge.

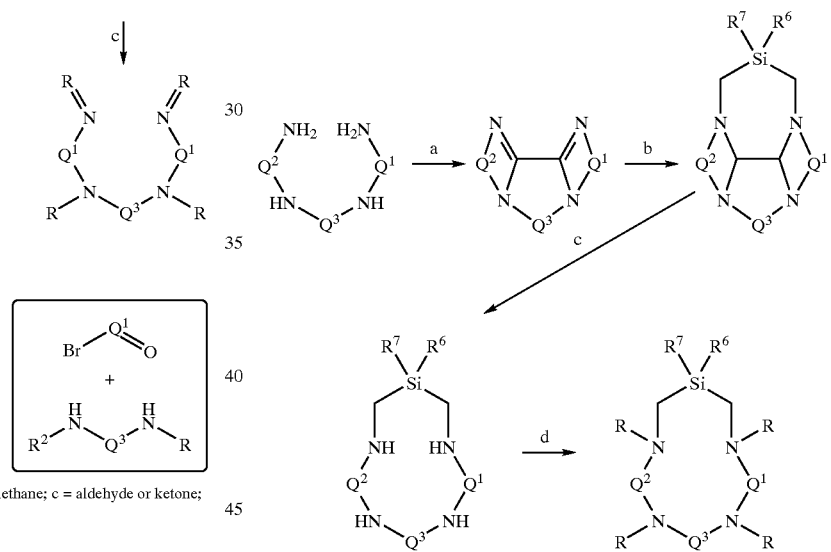

a = dimethylacetal/DMF; b = $R^6R^7Si(CH_2Cl)_2$; c = acid or base hydrolysis; d = alkyl bromide/triethylamine.

Scheme X.
Synthesis of 1,4,7,10-Tetraaza Macrocycles.

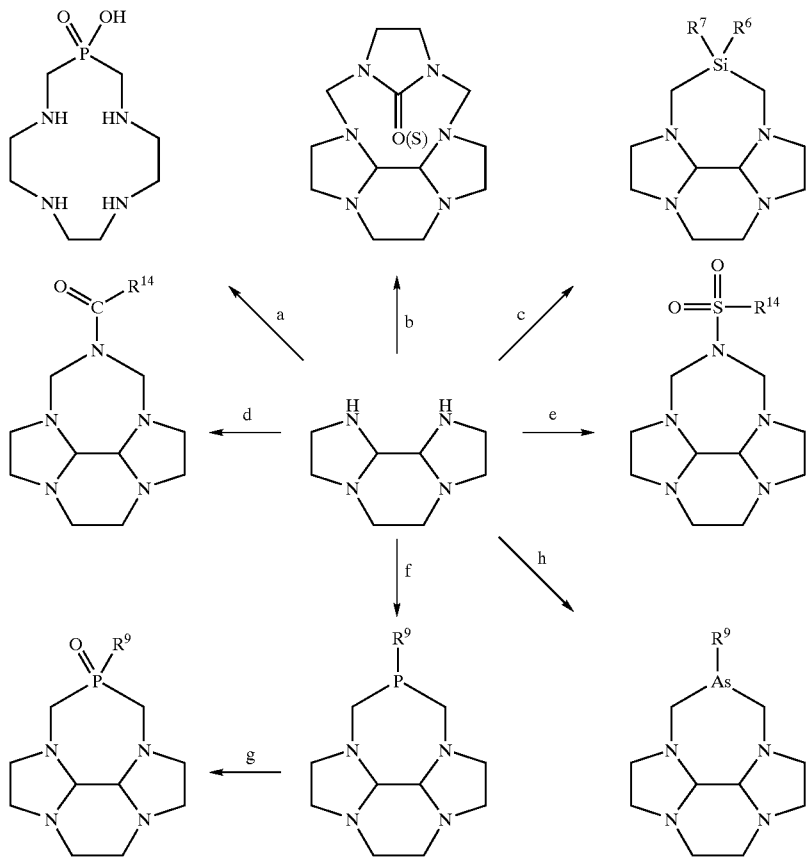

a = H$_2$P(O)OH/CH$_2$O/6N HCl; b = C$_3$H$_2$N$_2$O/CH$_2$O; c = R$^6$R$^7$Si(CH$_2$Cl)$_2$; d = R$^{14}$—CONH$_2$/CH$_2$O;

e = R$^{14}$—SO$_2$NH$_2$/CH$_2$O; f = Bis-hydroxymethylphoshine/pH = 3–5; g = [O]; h = Bis-hydroxymethylarsine/pH = 3–5.

Alternatively, the macrocyclic chelants can be synthesized from a tricyclic intermediate (Schemes X and XI), prepared from the reaction of a tetraamine with glycoxal derivatives (Weisman, G. R., et al. Tetrahedron Lett. 1980, 21, 335–338; Kolinski, R. A., et al. Tetrahedron Lett. 1981, 22, 2217–2220; Argese, M., et al. U.S. Pat. No. 5,880,281 (1999)). Reaction of Mannich substrates, including but not limited to phosphinic acid, bis(hydroxymethyl)-phosphine, bis(hydroxymethyl)arsine, amide, sulfonamide, or N-containing heterocycle, with the tricyclic intermediate results in formation of a variety of tetracyclic compounds. Oxidation and hydrolysis of the tetracyclic compounds produces the corresponding tetraaza macrocycles, which react readily with alkyl halide (particularly alkyl bromide) in the presence of an excess base such as triethylamine to give the alkylated tetraaza macrocycles. The two substituents on the phosphine-oxo bridges may be connected via an alkyl or aryl linker (Scheme II). The linker may contain one or more bifunctional groups useful for attachment of biomolecules.

Scheme XI.
Alternative Route for Synthesis of Macrocyclic Chelants with One Heteroatom-Containing Bridge.

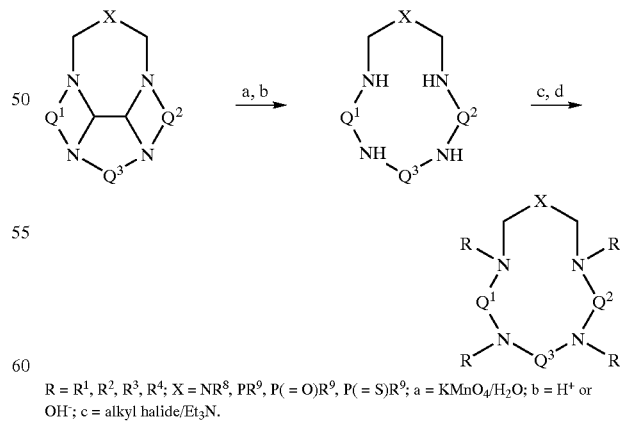

R = R$^1$, R$^2$, R$^3$, R$^4$; X = NR$^8$, PR$^9$, P(=O)R$^9$, P(=S)R$^9$; a = KMnO$_4$/H$_2$O; b = H$^+$ or OH$^-$; c = alkyl halide/Et$_3$N.

Macrocyclic Chelants Containing Hydroxyamine Moiety

Scheme XII shows the synthesis of examples of macrocyclic chelants containing the hydroxyamine moiety. First, the O-benzyl protected hydroxyamine reacts with a dialdehyde to form the corresponding Schiff base. The Schiff-base can be readily reduced to give a O-benzyl protected bis-hydroxyamine, which reacts with t-butyl bromoacetate in the presence of a base such as $Et_3N$ to produce the t-butyl tetraester of 1,10-bis(benzoxy-1,4,7,10-tetraazadecane-1,4,7,10-tetraacetic acid. Deprotection of the O-benzyl group is achieved by catalytic hydrogenation to give 1,10-dihydroxy-1,4,7,10-tetraazadecane-1,4,7,10-tetraacetic acid, which can react with the substituted organoborate, organotin dichloride, organogermyl dichloride, or phosphorodichloride to produce the macrocyclic chelant as its t-butyl ester. Hydrolysis of the t-butyl tetraester produces the macrocyclic chelant in its acid form. The substituents ($R^5$, $R^6$ and $R^8$ groups) on bridging heteroatom may contain the bifunctional groups for attachment of biomolecules. One of the four acetate arms can also be used for attachment of biomolecules. Thus, these macrocyclic chelants are useful as BFC's for the radiolabeling of biomolecules.

Scheme XII.
Synthesis of Hydroxyamine-Derivatized Macrocyclic Chelants.

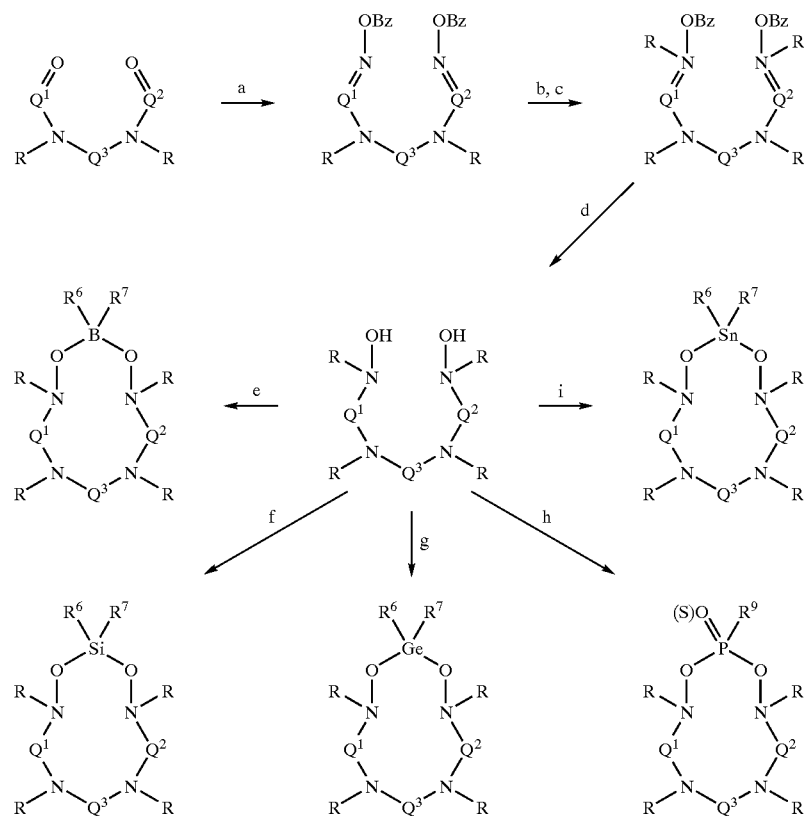

a = Bz—O—$NH_2$; b = $NaCNBH_3$; c = alkylbromide; d = $H_2$/Pd/C; e = $R^6R^7B(OH)$; f = $R^6R^7SiCl_2$; g = $R^6R^7GeCl_2$; h = $R^9PO(S)Cl_2$; i = $R^6R^7SnCl_2$.

Scheme XIII.
Synthesis of Hydrazine-Derivatized Macrocyclic Chelants.

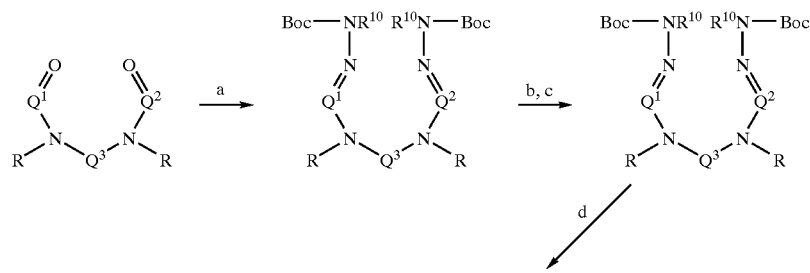

-continued

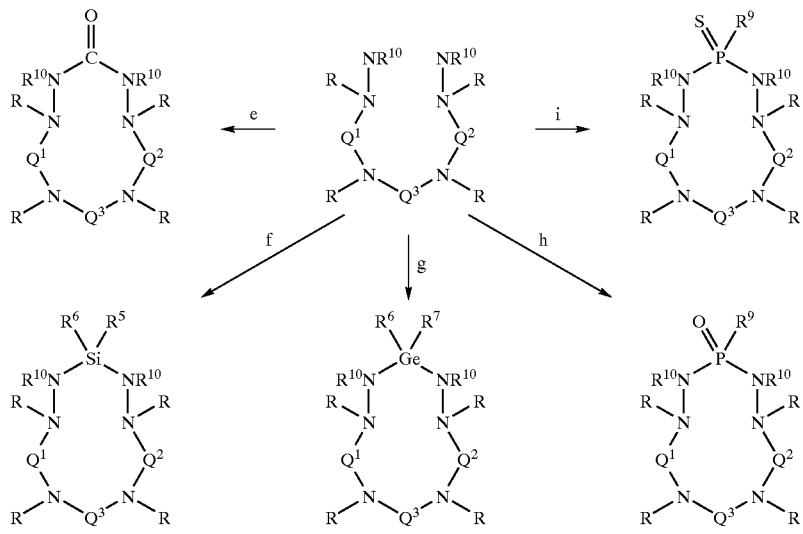

a = BocNH—NH$_2$; b = NaCNBH$_3$; c = alkylbromide; d = H$^+$; e = COCl$_2$;
f = R$^6$R$^7$SiCl$_2$; g = R$^6$R$^7$GeCl$_2$; h = R$^9$POCl$_2$; i = R$^9$PSCl$_2$.

Macrocyclic Chelants Containing Hydrazine Moiety

Scheme XIII shows synthesis of examples of macrocyclic chelants containing hydrazine moieties. First, the Boc-protected hydrazine reacts with a dialdehyde to form the corresponding hydrazone. Reduction of hydrazone (Singh et al, Inorg. Chem. 1994, 33, 736–741; Singh et al, Nuci. Med. Biol. 1995, 22, 849–857) gives the Boc-protected bis-hydrazine, which reacts with ethyl bromoacetate in the presence of a base such as Et $_3$N to produce the tetraethyl ester of 1,10-bis(Boc-amino)-1,4,7,10-tetraazadecane-1,4,7,10-tetraacetic acid. Deprotection of the Boc group is achieved using a mixture of TFA and dichloromethane to give the tetraethyl ester of 1,10-diamino-1,4,7,10-tetraazadecane-1,4,7,10-tetraacetic acid, which can react with a substituted carbonyldichloride, organotin dichloride, organogermyl dichloride, phosphorodichloride or phosphorodichloride to produce the macrocyclic chelant as its tetraethyl ester. Hydrolysis of the tetraester produces the macrocyclic chelant in its acid form. The substituents (R$^5$, R$^6$ and R$^8$ groups) on bridging heteroatom may contain the bifunctional groups for attachment of biomolecules. One of the four actetate arms can also be used for attachment of biomolecules. Thus, these macrocyclic chelants are useful as BFC's for the radiolabeling of biomolecules.

Scheme XIV.
An Alternative Route for Synthesis of
Hydrazine-Derivatized Macrocyclic Chelants.

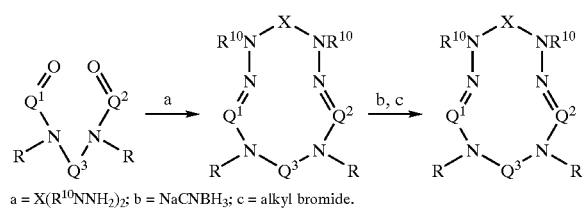

a = X(R$^{10}$NNH$_2$)$_2$; b = NaCNBH$_3$; c = alkyl bromide.

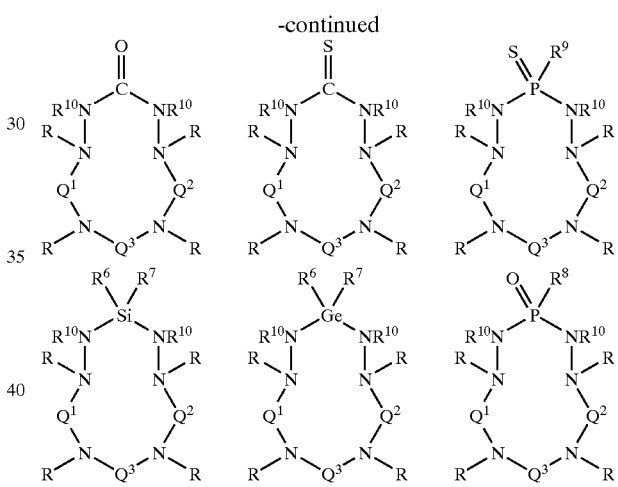

Alternatively, synthesis of macrocyclic chelants containing hydrazine moiety can also be accomplished according to Scheme XIV, which involves the formation of a cyclic hydrazone, followed by the reduction of hydrazone (Singh et al, Inorg. Chem. 1994, 33, 736–741; Singh et al, Nucl. Med. Biol. 1995, 22, 849–857), reaction with alkyl halide, particularly bromide, in the presence of a base and hydrolysis of the t-butyl ester groups.

The bio-targeted pharmaceuticals of the present invention have the formulae, $(W)_{d'}$—$L_n$—$(C_h$—$X)$, and $(W)_{d'}$—$L_n$—$(C_h$—$X^1)_{d'}$, wherein W represents a peptide, polypeptide, peptidomimetic, or non-peptide that binds to a receptor or enzyme expressed or up-regulated in angiogenic tumor vasculature, d is 1–10, $L_n$ represents an optional linking group, $C_h$ represents a novel metal chelator of the present invention, d' is 1–100, X represents a radioisotope, and $X^1$ represents paramagnetic metal ion.

The pharmaceuticals of the present invention can be synthesized by several approaches. One approach involves the synthesis of the targeting peptide, polypeptide, peptidomimetic or non-peptide moiety, W, and direct attachment of one or more moieties, W, to one or more metal chelators, $C_h$. Another approach involves the attachment of one or more moieties, W, to the linking group, $L_n$, which is then attached to one or more metal chelators, $C_h$. Another approach, useful in the synthesis of pharmaceuticals wherein d is 1, involves the synthesis of the moiety, W—$L_n$, together, by incorporating group bearing $L_n$ into the synthesis of the peptide, polypeptide, peptidomimetic, or non-peptide. The resulting moiety, W—$L_n$, is then attached to one or more metal chelators, $C_h$. Another approach involves the synthesis of a peptide, polypeptide, peptidomimetic, or non-peptide, W, bearing a fragment of the linking group, $L_n$, one or more of which are then attached to the remainder of the linking group and then to one or more metal chelators, $C_h$.

The peptides, polypeptides, peptidomimetics and non-peptides, W, optionally bearing a linking group, $L_n$, or a fragment of the linking group, can be synthesized using standard synthetic methods known to those skilled in the art. Preferred methods include but are not limited to those methods described below.

Generally, peptides, polypeptides, and peptidomimetics are elongated by deprotecting the alpha-amine of the C-terminal residue and coupling the next suitably protected amino acid through a peptide linkage using the methods described. This deprotection and coupling procedure is repeated until the desired sequence is obtained. This coupling can be performed with the constituent amino acids in a stepwise fashion, or condensation of fragments (two to several amino acids), or combination of both processes, or by solid phase peptide synthesis according to the method originally described by Merrifield, J. Am. Chem. Soc., 85, 2149–2154 (1963), the disclosure of which is hereby incorporated by reference.

The peptides, polypeptides and peptidomimetics may also be synthesized using automated synthesizing equipment. In addition to the foregoing, procedures for peptide, polypeptide and peptidomimetic synthesis are described in Stewart and Young, "Solid Phase Peptide Synthesis", 2nd ed, Pierce Chemical Co., Rockford, Ill. (1984); Gross, Meienhofer, Udenfriend, Eds., "The Peptides: Analysis, Synthesis, Biology, Vol. 1, 2, 3, 5, and 9, Academic Press, New York, (1980–1987); Bodanszky, "Peptide Chemistry: A Practical Textbook", Springer-Verlag, New York (1988); and Bodanszky et al. "The Practice of Peptide Synthesis" Springer-Verlag, New York (1984), the disclosures of which are hereby incorporated by reference.

The coupling between two amino acid derivatives, an amino acid and a peptide, polypeptide or peptidomimetic, two peptide, polypeptide or peptidomimetic fragments, or the cyclization of a peptide, polypeptide or peptidomimetic can be carried out using standard coupling procedures such as the azide method, mixed carbonic acid anhydride (isobutyl chloroformate) method, carbodiimide (dicyclohexylcarbodiimide, diisopropylcarbodiimide, or water-soluble carbodiimides) method, active ester (p-nitrophenyl ester, N-hydroxysuccinic imido ester) method, Woodward reagent K method, carbonyldiimidazole method, phosphorus reagents such as BOP-Cl, or oxidation-reduction method. Some of these methods (especially the carbodiimide) can be enhanced by the addition of 1-hydroxybenzotriazole. These coupling reactions may be performed in either solution (liquid phase) or solid phase.

The functional groups of the constituent amino acids or amino acid mimetics must be protected during the coupling reactions to avoid undesired bonds being formed. The protecting groups that can be used are listed in Greene, "Protective Groups in Organic Synthesis" John Wiley & Sons, New York (1981) and "The Peptides: Analysis, Synthesis, Biology, Vol. 3, Academic Press, New York (1981), the disclosure of which is hereby incorporated by reference.

The alpha-carboxyl group of the C-terminal residue is usually protected by an ester that can be cleaved to give the carboxylic acid. These protecting groups include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters. In the solid phase case, the C-terminal amino acid is attached to an insoluble carrier (usually polystyrene). These insoluble carriers contain a group which will react with the carboxyl group to form a bond which is stable to the elongation conditions but readily cleaved later. Examples of which are: oxime resin (DeGrado and Kaiser (1980) J. Org. Chem. 45, 1295–1300) chloro or bromomethyl resin, hydroxymethyl resin, and aminomethyl resin. Many of these resins are commercially available with the desired C-terminal amino acid already incorporated.

The alpha-amino group of each amino acid must be protected. Any protecting group known in the art can be used. Examples of these are: 1) acyl types such as formyl, trifluoroacetyl, phthalyl, and p-toluenesulfonyl; 2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); 3) aliphatic carbamate types such as tert-butyloxycarbonyl (Boc), ethoxycarbonyl, diisopropylmethoxycarbonyl, and allyloxycarbonyl; 4) cyclic alkyl carbamate types such as cyclopentyloxycarbonyl and adamantyloxycarbonyl; 5) alkyl types such as triphenylmethyl and benzyl; 6) trialkylsilane such as trimethylsilane; and 7) thiol containing types such as phenylthiocarbonyl and dithiasuccinoyl. The preferred alpha-amino protecting group is either Boc or Fmoc. Many amino acid or amino acid mimetic derivatives suitably protected for peptide synthesis are commercially available.

The alpha-amino protecting group is cleaved prior to the coupling of the next amino acid. When the Boc group is used, the methods of choice are trifluoroacetic acid, neat or in dichloromethane, or HCl in dioxane. The resulting ammonium salt is then neutralized either prior to the coupling or in situ with basic solutions such as aqueous buffers, or tertiary amines in dichloromethane or dimethylformamide. When the Fmoc group is used, the reagents of choice are piperidine or substituted piperidines in dimethylformamide, but any secondary amine or aqueous basic solutions can be used. The deprotection is carried out at a temperature between 0 OC and room temperature.

Any of the amino acids or amino acid mimetics bearing side chain functionalities must be protected during the preparation of the peptide using any of the above-identified groups. Those skilled in the art will appreciate that the selection and use of appropriate protecting groups for these side chain functionalities will depend upon the amino acid or amino acid mimetic and presence of other protecting groups in the peptide, polypeptide or peptidomimetic. The selection of such a protecting group is important in that it must not be removed during the deprotection and coupling of the alpha-amino group.

For example, when Boc is chosen for the alpha-amine protection the following protecting groups are acceptable: p-toluenesulfonyl (tosyl) moieties and nitro for arginine; benzyloxycarbonyl, substituted benzyloxycarbonyls, tosyl or trifluoroacetyl for lysine; benzyl or alkyl esters such as cyclopentyl for glutamic and aspartic acids; benzyl ethers for serine and threonine; benzyl ethers, substituted benzyl ethers or 2-bromobenzyloxycarbonyl for tyrosine; p-methylbenzyl, p-methoxybenzyl, acetamidomethyl, benzyl, or t-butylsulfonyl for cysteine; and the indole of tryptophan can either be left unprotected or protected with a formyl group.

When Fmoc is chosen for the alpha-amine protection usually tert-butyl based protecting groups are acceptable. For instance, Boc can be used for lysine, tert-butyl ether for serine, threonine and tyrosine, and tert-butyl ester for glutamic and aspartic acids.

Once the elongation of the peptide, polypeptide or peptidomimetic, or the elongation and cyclization of a cyclic peptide or peptidomimetic is completed all of the protecting groups are removed. For the liquid phase synthesis the protecting groups are removed in whatever manner as dictated by the choice of protecting groups. These procedures are well known to those skilled in the art.

When a solid phase synthesis is used to synthesize a cyclic peptide or peptidomimetic, the peptide or peptidomimetic should be removed from the resin without simultaneously removing protecting groups from functional groups that might interfere with the cyclization process. Thus, if the peptide or peptidomimetic is to be cyclized in solution, the cleavage conditions need to be chosen such that a free a-carboxylate and a free a-amino group are generated without simultaneously removing other protecting groups. Alternatively, the peptide or peptidomimetic may be removed from the resin by hydrazinolysis, and then coupled by the azide method. Another very convenient method involves the synthesis of peptides or peptidomimetics on an oxime resin, followed by intramolecular nucleophilic displacement from the resin, which generates a cyclic peptide or peptidomimetic (Osapay, Profit, and Taylor (1990) Tetrahedron Letters 43, 6121–6124). When the oxime resin is employed, the Boc protection scheme is generally chosen. Then, the preferred method for removing side chain protecting groups generally involves treatment with anhydrous HF containing additives such as dimethyl sulfide, anisole, thioanisole, or p-cresol at 0° C. The cleavage of the peptide or peptidomimetic can also be accomplished by other acid reagents such as trifluoromethanesulfonic acid/ trifluoroacetic acid mixtures.

Unusual amino acids used in this invention can be synthesized by standard methods familiar to those skilled in the art ("The Peptides: Analysis, Synthesis, Biology, Vol. 5, pp. 342–449, Academic Press, New York (1981)). N-Alkyl amino acids can be prepared using procedures described in previously (Cheung et al., (1977) Can. J. Chem. 55, 906; Freidinger et al., (1982) J. Org. Chem. 48, 77 (1982)), which are incorporated herein by reference.

Additional synthetic procedures that can be used by one of skill in the art to synthesize the peptides, polypeptides and peptidomimetics targeting moieties are described in U.S. Pat. No. 5,879,657, the contents of which are herein incorporated by reference.

The attachment of linking groups, $L_n$, to the peptides, polypeptides, peptidomimetics and non-peptide, W; chelators, $C_h$, to the peptides, polypeptides, peptidomimetics, and non-peptides, W, or to the linking groups, $L_n$; and peptides, polypeptides, peptidomimetics, and non-peptides bearing a fragment of the linking group to the remainder of the linking group, in combination forming the moiety, $(W)_d$—$L_n$, and then to the moiety $C_h$; can all be performed by standard techniques. These include, but are not limited to, amidation, esterification, alkylation, and the formation of ureas or thioureas. Procedures for performing these attachments can be found in Brinkley, M., Bioconjugate Chemistry 1992, 3(1), which is incorporated herein by reference.

The linking group $L_n$ can serve several roles. First it provides a spacing group between the metal chelator, and the one or more of the peptides, polypeptides, peptidomimetics, or non-peptides, W, so as to minimize the possibility that the moieties $C_h$—X, $C_h$—$X^1$, will interfere with the interaction of the recognition sequences of W with the target receptors. The necessity of incorporating a linking group in a reagent is dependent on the identity of W, $C_h$—X, and $C_h$—$X^1$. If $C_h$—X, and $C_h$—$X^1$, cannot be attached to W without substantially diminishing its affinity for the receptors, then a linking group is used. A linking group also provides a means of independently attaching multiple peptides, polypeptides, peptidomimetics, and non-peptides, W, to one group that is attached to $C_h$—X, or $C_h$—$X^1$.

The linking group also provides a means of incorporating a pharmacokinetic modifier into the pharmaceuticals of the present invention. The pharmacokinetic modifier serves to direct the biodistribution of the injected pharmaceutical other than by the interaction of the targeting moieties, W, with the target receptors. A wide variety of functional groups can serve as pharmacokinetic modifiers, including, but not limited to, carbohydrates, polyalkylene glycols, peptides or other polyamino acids, and cyclodextrins. The modifiers can be used to enhance or decrease hydrophilicity and to enhance or decrease the rate of blood clearance. The modifiers can also be used to direct the route of elimination of the pharmaceuticals. Preferred pharmacokinetic modifiers are those that result in moderate to fast blood clearance and enhanced renal excretion.

For the diagnosis of thromboembolic disorders or atherosclerosis, W is selected from the group including the cyclic IIb/IIIa receptor antagonist compounds described in U.S. Pat. No. 5,879,657; the RGD containing peptides described in U.S. Pat. Nos. 4,578,079 and 4,792,525, the published patent applications WO89/05150, WO89/10135, WO91/01331, WO91/15515 and by Ojima et. al., 204th Meeting of the Amer. Chem. Soc., 1992, Abstract 44; the peptides that are fibrinogen receptor antagonists described in European Patent Applications EP410537A1, EP410539A1, EP410541A1, EP422937A1, EP422938A1, EP425212A2 the specific binding peptides and polypeptides described as IIb/IIIa receptor ligands, ligands for the polymerization site of fibrin, laminin derivatives, ligands for fibrinogen, or thrombin ligands in PCT WO 93/23085 (excluding the technetium binding groups); the oligopeptides that correspond to the IIIa protein described in PCT WO90/00178; the hirudin-based peptides described in PCT WO90/03391; the IIb/IIIa receptor ligands described in PCT WO90/15818; the thrombus, platelet binding or atherosclerotic plaque binding peptides described in PCT WO92/13572 (excluding the technetium binding group) or GB226849A1; the fibrin binding peptides described in U.S. Pat. Nos. 4,427,646 and 5,270,030; the hirudin-based peptides described in U.S. Pat. No. 5,279,812; or the fibrin binding proteins described in U.S. Pat. No. 5,217,705; the guanine derivatives that bind to the IIb/IIIa receptor described in U.S. Pat. No. 5,086,069; or the tyrosine derivatives described in European Patent Application 0478328A1, and by Hartman et. al., J. Med. Chem., 1992, 35, 464Q, or oxidized low density lipoproten (LDL).

For the diagnosis of infection, inflammation or transplant rejection, W is selected from the group including the leukocyte binding peptides described in PCT WO93/17719 (excluding the technetium binding group), PCT WO92/ 13572 (excluding the technetium binding group) or U.S. Pat. No. 5,792,444; the chemotactic peptides described in Eur. Pat. Appl. EP398143A1 or A. Fischman et. al., Semin. Nuc. Med., 1994, 24, 154; the leukostimulatory agents described in U.S. Pat. No. 5,277,892; or the LTB4 antagonists described in PCT Patent Application WO98/15295.

For the diagnosis of cancer, W is selected from the group of somatostatin analogs described in UK Application 8927255.3 or PCT WO94/00489, the selectin binding peptides described in PCT WO94/05269, the biological-function domains described in PCT WO93/12819, Platelet Factor 4 or the growth factors (PDGF, VEGF, EGF, FGF, TNF MCSF or the interleukins Il1-8).

W may also be a compound that binds a receptor that is expressed or upregulated in angiogenic tumor vasculature. For targeting the VEGF receptors, Flk-1/KDR, Flt-1, and neuropilin-1, the targeting moieties are comprised of peptides, polypeptides or peptidomimetics that bind with high affinity to the receptors. For example, peptides comprised of a 23 amino acid portion of the C-terminal domain of VEGF have been synthesized which competitively inhibit binding of VEGF to VEGFR (Soker, et. al., J. Biol. Chem., 1997, 272, 31582–8). Linear peptides of 11 to 23 amino acid residues that bind to the basic FGF receptor (bFGFR) are described by Cosic et. al., Mol. and Cell. Biochem., 1994, 130, 1–9. A preferred linear peptide antagonist of the bFGFR is the 16 amino acid peptide, Met-Trp-Tyr-Arg-Pro-Asp-Leu-Asp-Glu-Arg-Lys-Gln-Gln-Lys-Arg-Glu (SEQ ID NO:1). Gho et. al. (Cancer Research, 1997, 57, 3733–40) describe the identification of small peptides that bind with high affinity to the angiogenin receptor on the surface of endothelial cells. A preferred peptide is Ala-Gln-Leu-Ala-Gly-Glu-Cys-Arg-Glu-Asn-Val-Cys-Met-Gly-Ile-Glu-Gly-Arg (SEQ ID NO:2), in which the two Cys residues form an intramolecular disulfide bond. Yayon et. al. (Proc. Natl. Acad. Sci, USA, 1993, 90, 10643–7) describe other linear peptide antagonists of FGFR, identified from a random phage-displayed peptide library. Two linear octapeptides, Ala-Pro-Ser-Gly-His-Tyr-Lys-Gly (SEQ ID NO:3) and Lys-Arg-Thr-Gly-Gln-Tyr-Lys-Leu (SEQ ID NO:4) are preferred for inhibiting binding of bFGF to it receptor.

Targeting moieties for integrins expressed in tumor vasculature include peptides, polypeptides and peptidomimetics that bind to avB3, avB5, a5B1, a4B1, a1B1, and a2B2. Pierschbacher and Rouslahti (J. Biol. Chem., 1987, 262, 17294–8) describe peptides that bind selectively to a5B1 and avB3. U.S. Pat. No. 5,536,814 describes peptides that bind with high affinity to the integrin a5B1. Burgess and Lim (J. Med. Chem., 1996, 39, 4520–6) disclose the synthesis of three peptides that bind with high affinity to avB3: cyclo [Arg-Gly-Asp-Arg-Gly-Asp] (SEQ ID NO:5), cyclo[Arg-Gly-Asp-Arg-Gly-D-Asp] (SEQ ID NO:6) and the linear peptide Arg-Gly-Asp-Arg-Gly-Asp (SEQ ID NO:7). U.S. Pat. Nos. 5,770,565 and 5,766,591 disclose peptides that bind with high affinity to avB3. U.S. Pat. Nos. 5,767,071 and 5,780,426, disclose cyclic peptides that have an exocyclic Arg amino acid that have high affinity for avB3. Srivatsa et. al., (Cardiovascular Res., 1997, 36, 408–28) describe the cyclic peptide antagonist for avB3, cyclo[Ala-Arg-Gly-Asp-Mamb] (SEQ ID NO:8). Tran et. al., (Bioorg. Med. Chem. Lett., 1997, 7, 997–1002) disclose the cyclic peptide cyclo [Arg-Gly-Asp-Val-Gly-Ser-BTD-Ser-Gly-Val-Ala] (SEQ ID NO:9) that binds with high affinity to avB3. Arap et. al. (Science, 1998, 279, 377–80) describe cyclic peptides that bind to avB3 and avB5, Cys-Asp-Cys-Arg-Gly-Asp-Cys-Phe-Cys (SEQ ID NO:10), and cyclo[Cys-Asn-Gly-Asp-Cys] (SEQ ID NO:11). Corbett et. al. (Biorg. Med. Chem. Lett., 1997, 7, 1371–6) describe a series of avB3 selective peptidomimetics. And Haubner et. al., (Angew. Chem. Int. Ed. Engl., 1997, 36, 1374–89) disclose peptides and peptidomimetic avB3 antagonists obtained from peptide libraries.

Alternative targeting moieties for tumor vasculature include compounds that interact with receptor tyrosine kinases. Receptor tyrosine kinases (TKs) are membrane proteins, which play a key role in the transduction of mitogenic signals across the cell to the nucleus (Rewcastle, G. W. et al., J. Med. Chem. 1995, 38, 3482–3487; Thompson, A. M. et al, J. Med. Chem. 1997, 40, 3915–3925). Of the many TKs that have been identified and characterized, those of the epidermal growth factor receptor (EGFR) family are particularly important, and have been implicated in a variety of ectopic cell proliferative processes. The over-expression of human EGF receptor is greatly amplified in several human tumors (Fry, D. W., Exp. Opin. Invest. Drugs 1994, 3, 577–595; Jardines, L. et al., Pathobiology 1993, 61, 268–282), accompanied by an overphosphorylation of their protein targets. This increased phosphorylation of substrate tyrosine residues by oncogenic TK proteins is an essential step in the neoplastic transformation. Consequently, there has been great interest in developing inhibitors of TKs (TKIs) as anticancer drugs (Burke, T. R. Jr., Drugs Future 1992 17, 119–131; Chang, C. J. and Geahlen, R., J. Nat. Prod. 1992, 55, 1529–1560). The over-expression of EGF receptors in tumor cells also provides the foundation for the development of diagnostic and therapeutic radiopharmaceuticals by attaching a chelator and a radionuclide onto the TK receptor ligand (tyrosine kinase inhibitor).

W may also represent proteins, antibodies, antibody fragments, peptides, polypeptides, or peptidomimetics that bind to receptors or binding sites on other tissues, organs, enzymes or fluids. Examples include the β-amyloid proteins that have been demonstrated to accumulate in patients with Alzheimer's disease, atrial naturetic factor derived peptides that bind to myocardial and renal receptors, antimyosin antibodies that bind to areas of infarcted tissues, or nitroimidazole derivatives that localize in hypoxic areas in vivo.

EXAMPLES

N,N-Dibenzylethylenediamine, ethylenediamine-N,N'-diacetic acid, paraformaldehyde, phosphinic acid, and pyridoxal hydrochloride were purchased from Aldrich. N,N'-bis (pyridoxyl)ethylenediamine was prepared by reduction of N,N'-bis(pyridoxylidene)ethylenediamine with potassium borohydride according to the literature(*Inorg. Chem.* 1994, 23, 1188–1192).

Instruments. $^1$H NMR spectra were recorded on a 270 MHz Bruker spectrometer. The $^1$H NMR data were reported as δ (ppm) relative to TMS. Electrospray MS analyses were performed using a VG Quattro mass spectrometer. LC—MS spectra were collected using a HP1100 LC/MSD system with API-electrospray interface. The high-performance liquid HPLC methods used a Hewlett Packard Model 1090 instrument with radiometric detector using a sodium iodide probe.

Example I

Synthesis of TETA(PO)₂

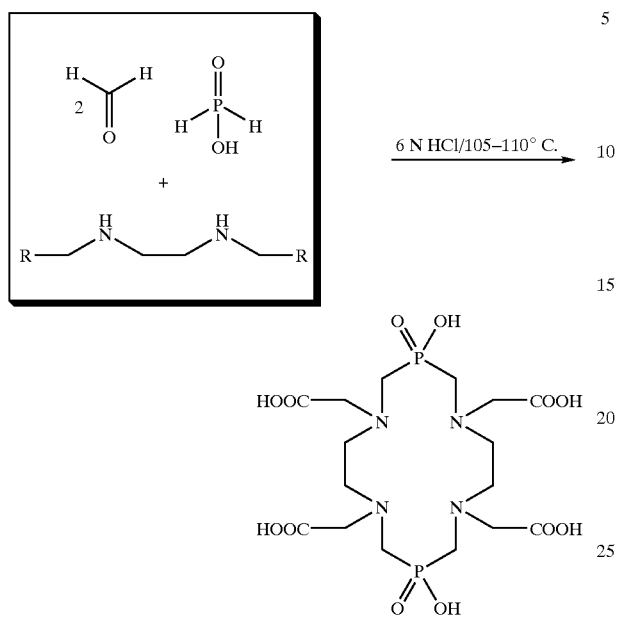

Ethylenediamine-N,N'-diacetic acid (3.4 g, 19.3 mmol) was suspended 6 N HCl (50 mL), and the resulting mixture was heated to 105–110° C. under vigorous stirring. Paraformaldehyde (2.8 g, 93 mmol) was then added to give a clear solution. Phosphinic acid (2 mL of 50% aqueous solution, 19.3 mmol) was added in four equal portions over 15–20 min. The reaction mixture was heated to reflux for 3–4 hours, during which time a white precipitate formed. The reaction mixture was allowed to cool at room temperature. The white solid was separated by filtration, washed with 6 N HCl (5 mL), and acetone (5 mL), and dried under vacuum overnight. The yield was 0.43 g. $^1$H NMR (in D$_2$O+KOD, chemical shift δ in ppm relative to TMS): 3.53 (s, 8H, NCH$_2$COOH); 3.44 (s, 8H, NCH$_2$CH$_2$N); 3.27 (d, 8H, NCH$_2$P, $J_{H-P}$=12.9 Hz). $^{31}$p NMR (chemical shift δ in ppm relative to phosphoric acid): 24.8 ppm. Electrospray MS: m/z=531.3 for [M–H]$^{-1}$ (M=C$_{16}$H$_{30}$N$_4$O$_{12}$P$_2$), 265.1 for [M–2H]$^{-2}$, 132.0 for [M–4H]$^{-4}$.

Example II

Synthesis of TETB(PO)₂

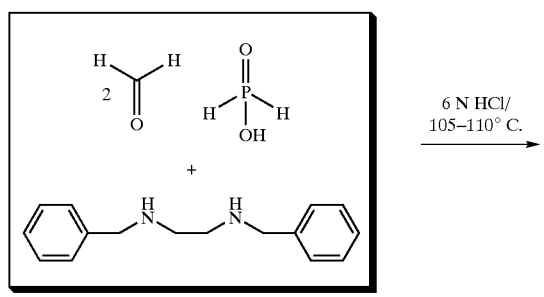

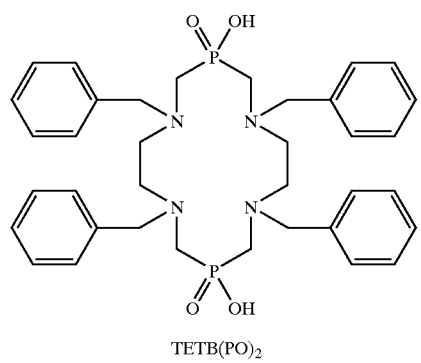

TETB(PO)₂

N,N-Dibenzylethylenediamine (4.86 g, 19.3 mmol) was slowly added to a 6 N HCl solution (50 mL) to give a white slurry. The resulting mixture was heated to 105–110° C. under vigorous stirring. Paraformaldehyde (2.8 g, 93 mmol) was then added to give a clear solution. Phosphinic acid (2 mL of 50% aqueous solution, 19.3 mmol) was added in four equal portions over 15–20 min. The reaction mixture was heated to reflux for another 60 min, and was allowed to cool at room temperature, and was then filtered. The filtrate was evaporated to give a white solid, which was then recrystallized from acetone/methanol. The white solid was dried under vaccum overnight to give 4.5 g of the product (70% based on N,N-dibenzylethylenediamine). Electrospray LC/MS (negative mode): m/z=659.2 for [M–1]$^-$ (C$_{36}$H$_{45}$N$_4$O$_4$P$_2$) and 329.2 for [M–2]$^{2-}$. $^1$H NMR (in D$_2$O, chemical shift δ in ppm): 3.36 (d, 8H, PCH$_2$), 3.70 (s, 8H, CH$_2$CH$_2$), 4.40 (s, 8H, PhCH$_2$), and 7.00–7.38 (m, 20H, C$_6$H$_5$).

Example III

Synthesis of TETPD(PO)₂

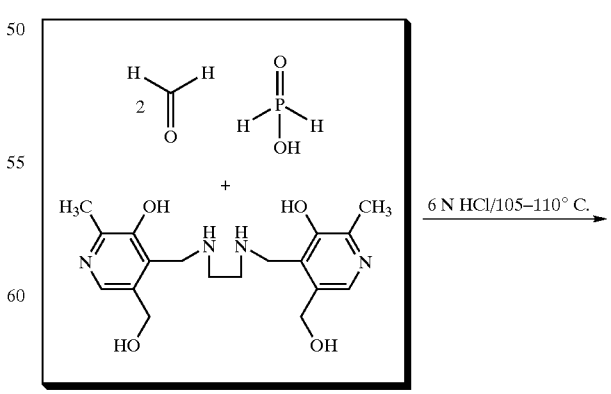

TETPD(PO)₂

N,N'-Bis(pyridoxyl)ethylene-diamine (3.65 g, 10 mmol) was added to a 6 N HCl solution (50 mL), and the resulting mixture was heated to 105–110° C. under vigorous stirring. Paraformaldehyde (2.8 g, 93 mmol) was then added to give a clear solution. Phosphinic acid (2 mL of 50% aqueous solution, 19.3 mmol) was added in four equal portions over 15–20 min. The reaction mixture was heated to reflux for another 2 h. The resulting solution was concentrated to give a gummy residue, which was redissolved in 30 –40 mL of hot methanol. The solution was then slowly added to 150 mL of acetone to give a white solid. The white solid was recrystallized from acetone/methanol. The product was dried under vaccum overnight. The yield was ~4.2 g (~79%). Electrospray LC/MS (negative mode): m/z=903.1 for [M−1]⁻($C_{40}H_{57}N_8O_{12}P_2$), and 451.3 for [M−2]²⁻. ¹H NMR (in $D_2O$, chemical shift δ in ppm): 2.45 (s, 12H, $CH_3$), 2.96 (d, 8H, $PCH_2$), 3.30 (s, 8H, $CH_2CH_2$), 4.30 (s, 8H, Py—$CH_2$), and 7.80 (2, 4H, Py).

Example IV

Synthesis of [GdTETA(PO)₂]

To a mixture of TETA(PO)₂ (53 mg, 0.1 mmole) and gadolinium nitrate pentahydrate (43 mg, 0.1 mmole) in methanol (5 mL) and water (1 mL) was added 1 N sodium hydroxide dropwise until the pH was adjusted to ~7.0. The resulting solution was heated to reflux for 10–15 min, and was then allowed to stand room temperature to evaporate solvents slowly while a white solid was formed. The solid was collected, washed with a small amount of methanol and acetone, and then dried under vacuum overnight. The yield was 45 mg. Electrospray MS (negative mode): m/z=708.1 for [M+Na−H]⁻, 686.1 for [M−1]⁻($C_{16}H_{26}N_4O_{12}P_2Gd$), and 342.5 for [M−H]⁻².

Example V

Synthesis of [LuTETA(PO)₂]

0.1 mmole) and lutetium chloride hexaahydrate (40 mg, 0.1 mmole) in methanol (5 mL) and water (1 mL) was added 1 N sodium hydroxide dropwise until the pH was adjusted to ~7.0. The resulting solution was heated to reflux for 10–15 min, and was then allowed to stand room temperature to give a white solid. The solid was collected, washed with methanol (5 mL) and acetone (3 mL), and then dried under vacuum overnight. The yield was 40 mg. ¹H NMR (in $D_2O$, chemical shift δ in ppm relative to TMS): 2.80 (bs, 8H, $NCH_2COO$); 3.1 (bs, 8H, $NCH_2CH_2N$); 8 (bs, 8H, $NCH_2P$). ³¹P NMR (chemical shift δ in ppm relative to phosphoric acid): 34.9 ppm. Electrospray MS (negative mode): m/z= 747.1 for [M+2Na−2H]⁻, 725.1 for [M+Na−H]⁻, 703.1 for [M]⁻($C_{16}H_{26}N_4O_{12}P_2Lu$) 351.2 for [M−H]⁻², and 132.0 for [M−3H]⁻⁴.

Example VI

Synthesis of [Cu₂TETPD(PO)₂]

To a solution of TETPD(PO)₂ (500 mg, 0.5 mmole) in methanol (50 mL) was added copper(II) chloride trihydrate (400 mg, 0.1 mmole) to give a dark green solution with some precipitate. Upon addition of water (8–10 mL), the resulting solution was filtered. The filtrate was allowed to stand room temperature to evaporate solvents slowly while a dark green solid was formed. The solid was collected, washed with acetone, and then dried under vacuum overnight. The yield was 185 mg. Electrospray MS (positive mode): m/z=1027.1 for [M+1]⁺($C_{40}H_{54}N_8O_{12}P_2Cu_2$), 514.0 for [M+2H]²⁺ and 258.6 for [M−2H]⁺⁴.

Example VII

Synthesis of ¹¹¹In Complex of TETA(PO)₂

To a lead shielded vial (300 pL HPLC autosampler vial) was added 10 μL of ¹¹¹InCl₃ solution (50 mCi/mL in 0.05 N HCl), followed by 100 μL of TETA(PO)₂ solution (10 mg/mL in 0.5 M ammonium acetate buffer, pH=6.95), and 50 μL of 0.5 M ammonium acetate buffer (pH=6.95). The total volume was ~160 μL and the pH of the reaction mixture was ~6.5. The mixture was heated at 80° C. for 30 min, and then was analyzed by ITLC. The radiolabeling yield was 98.2%.

Example VIII

Synthesis of ¹⁷⁷Lu Complex of TETA(PO)₂

To a lead shielded vial (300 μL HPLC autosampler vial) was added 10 μL of ¹⁷⁷LuCl₃ solution (100 mCi/mL in 0.05 N HCl), followed by 100 μL of TETA(PO)₂ solution (10 mg/mL in 0.5 M ammonium acetate buffer, pH =6.95), and 100 μL of 0.5 M ammonium acetate buffer (pH 6.95). The total volume was 210 μL and the pH of the reaction mixture was 6.5. The mixture was heated at 80° C. for 30 min, and then was analyzed by ITLC. The radiolabeling yield was 97.0%.

Example IX

Synthesis of ⁹⁰Y Complex of TETA(PO)₂

To a lead shielded vial (300 μL HPLC autosampler vial) was added 10 μL of ⁹⁰YCl₃ solution (100 mCi/mL in 0.05 N HCl), followed by 100 μL of TETA(PO)₂ solution (10 mg/mL in 0.5 M ammonium acetate buffer, pH=6.95), and 100 μL of 0.5 M ammonium acetate buffer (pH=6.95). The total volume was 210 μL and the pH of the reaction mixture was ~6.5. The mixture was heated at 100° C. for 10 min, and then was analyzed by ITLC. The radiolabeling yield was >95.0%.

Utility

The diagnostic radiopharmaceuticals are administered by intravenous injection, usually in saline solution, at a dose of 1 to 100 mCi per 70 kg body weight, or preferably at a dose of 5 to 50 mCi. Imaging is performed using known procedures.

The therapeutic radiopharmaceuticals are administered by intravenous injection, usually in saline solution, at a dose of 0.1 to 100 mCi per 70 kg body weight, or preferably at a dose of 0.5 to 5 mCi per 70 kg body weight.

The magnetic resonance imaging contrast agents of the present invention may be used in a similar manner as other MRI agents as described in U.S. Patent 5,155,215; U.S. Pat. No. 5,087,440; Margerstadt et al., Magn. Reson. Med., 1986, 3, 808; Runge et al., Radiology, 1988, 166, 835; and Bousquet et al., Radiology, 1988, 166, 693. Generally, sterile aqueous solutions of the contrast agents are administered to a patient intravenously in dosages ranging from 0.01 to 1.0 mmoles per kg body weight.

Target specific metallopharmaceuticals of the present invention can be evaluated in the following representative in vitro and in vivo models.

LTB4 Human Neutrophil (PMN) Binding Assay

Heparinized blood was placed on a ficol gradient followed by its sedimentation with dextran. This resulted in preparations containing >95% neutrophils (PMN). The PMN solution was adjusted to achieve a concentration of $8 \times 10^6$ PMN/ml. In this assay the test agent will actively compete with 3[H] LTB4 for the PMN LTB4 receptor. Very briefly, the assay was performed as follows; [3H]LTB4 (1 nM) and test agent were placed into a 96 well microplate with filters (0.65 $\mu$m pore size). PMN solution ($8 \times 10^6$/ml) was added and the microplate incubated for 10 min at 4° C. The microplate was then placed on Millipore filtration system; the wells washed with cold saline (3×) and dried. The filters were removed from the microplate; placed into scintillation fluid and the concentration of [3H]LTB4 determined.

Guinea Pig Focal Infection Model

The function of the model is to rapidly assess an agent's ability to detect inflammation/infection as well as determine the biodistribution. Very briefly, the procedure was as follows: A #10 trochar needle was used to introduce a piece of umbilical tape immersed in a 6% sodium caseinate solution into the right flank and placed on the left side of the peritoneal cavity of anesthetized guinea pigs. The placement of the immersed string served as the focal site for white blood cell recruitment over the next eighteen hours. Eighteen hours later the guinea pigs were anesthetized and the test agent administered via the lateral saphenous vein. At the appropriate time postinjection, the animals were euthanized and the focal uptake determined. Throughout the course of the study blood was withdrawn via cardiac puncture. Uptake and target/background ratios were determined via well counting.

Rabbit Focal Infection Model

The function of the model is to rapidly assess an agent's ability to detect inflammation/infection via scintigraphy as well as determine the biodistribution. The protocol takes place over 2 days and is comprised of induction of an infection, imaging, followed by a biodistribution. Very briefly, the procedure was as follows: On day 1, $2 \times 10^9$ colonies of E.coli was administered intramuscularly in the thigh to anesthetized rabbits. The infection was permitted to fulminate for 24 hrs prior to the intravenous administration of the test agent. Prior to the administration of the test agent, the animal was anesthetized, intubated and monitored to assess arterial pressure and heart rate and hematology. Anterior 5 min serial images images were performed over a 4 hr period. At the end of the protocol the animal was euthanized with a pentobarbital overdose and the uptake of the test agent in various organs assessed via well counting.

Canine Deep Vein Thrombosis Model

This model incorporates the triad of events (hypercoagulatible state, period of stasis, low shear environment) essential for the formation of a venous fibrin-rich actively growing thrombus. The procedure was as follows: Adult mongrel dogs of either sex (9–13 kg) were anesthetized with pentobarbital sodium (35 mg/kg,i.v.) and ventilated with room air via an endotracheal tube (12 strokes/min, 25 ml/kg). For arterial pressure determination, the right femoral artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. The right femoral vein was cannulated (PE-240) for drug administration. A 5 cm segment of both jugular veins was isolated, freed from fascia and circumscribed with silk suture. A microthermister probe was placed on the vessel which serves as an indirect measure of venous flow. A balloon embolectomy catheter was utilized to induce the 15 min period of stasis during which time a hypercoagulatible state was then induced using 5 U thrombin (American Diagnosticia, Greenwich Conn.) administered into the occluded segment. Fifteen minutes later, flow was reestablished by deflating the balloon. The radiopharmaceutical was infused during the first 5 minutes of reflow and the rate of incorporation monitored using gamma scintigraphy.

Arteriovenous Shunt Model

Adult mongrel dogs of either sex (9–13 kg) were anesthetized with pentobarbital sodium (35 mg/kg,i.v.) and ventilated with room air via an endotracheal tube (12 strokes/min,25 ml/kg). For arterial pressure determination, the left carotid artery was cannulated with a saline-filled polyethylene catheter (PE-240) and connected to a Statham pressure transducer (P23ID; Oxnard, Calif.). Mean arterial blood pressure was determined via damping the pulsatile pressure signal. Heart rate was monitored using a cardiotachometer (Biotach, Grass Quincy, Mass.) triggered from a lead II electrocardiogram generated by limb leads. A jugular vein was cannulated (PE-240) for drug administration. The both femoral arteries and femoral veins were cannulated with silicon treated (Sigmacote, Sigma Chemical Co. St Louis, Mo.), saline filled polyethylene tubing (PE-200) and connected with a 5 cm section of silicon treated tubing (PE-240) to form an extracorporeal arterio-venous shunts (A-V). Shunt patency was monitored using a doppler flow system (model VF-1, Crystal Biotech Inc, Hopkinton, Mass.) and flow probe (2–2.3 mm, Titronics Med. Inst., Iowa City, Iowa) placed proximal to the locus of the shunt. All parameters were monitored continuously on a polygraph recorder (model 7D Grass) at a paper speed of 10 mm/min or 25 mm/sec.

On completion of a 15 minute post surgical stabilization period, an occlusive thrombus was formed by the introduction of a thrombogenic surface (4–0 braided silk thread, 5 cm in length, Ethicon Inc., Somerville, N.J.) into the shunt one shunt with the other serving as a control. Two consecutive 1 hour shunt periods were employed with the test agent administered as an infusion over 5 minutes beginning 5 minutes before insertion of the thrombogenic surface. At the end of each 1 hour shunt period, the silk was carefully removed and weighed and the percent incorporation determined via well counting. Thrombus weight was calculated by subtracting the weight of the silk prior to placement from the total weight of the silk on removal from the shunt.

Arterial blood was withdrawn prior to the first shunt and every 30 minutes thereafter for determination of blood clearance, whole blood collagen-induced platelet aggregation, thrombin-induced platelet degranulation (platelet ATP release), prothrombin time and platelet count. Template bleeding time was also performed at 30 minute intervals.

Immobilized Human Placental $a_vb3$ Receptor Assay

The assay conditions were developed and validated using [I-125]vitronectin. Assay validation included Scatchard format analysis (n=3) where receptor number (Bmax) and Kd (affinity) were determined. Assay format is such that compounds are preliminarily screened at 10 and 100 nM final concentrations prior to IC50 determination. Three standards (vitronectin, anti-$a_vb_3$ antibody, LM609, and anti-$a_vb_5$, P1F6) and five reference peptides have been evaluated for IC50 determination. Briefly, the method involves immobilizing previously isolated receptors in 96 well plates and incubating overnight. The receptors were isolated from normal, fresh, non-infectious (HIV, hepatitis B and C, syphilis, and HTLV free) human placenta. The tissue was lysed and tissue debris removed via centrifugation. The lysate was filtered. The receptors were isolated by affinity chromatography using the immobilized $a_vb_3$ antibody. The plates are then washed 3× with wash buffer. Blocking buffer is added and plates incubated for 120 minutes at room temperature. During this time, compounds to be tested and [I-125]vitronectin are premixed in a reservoir plate. Blocking buffer is removed and compound mixture pipetted. Competition is carried out for 60 minutes at room temperature. Unbound material is then removed and wells are separated and counted via gamma scintillation.

Other Receptor Binding Assays

Whole cell assays for the determination of the binding affinity of pharmaceuticals of the present invention for the VEGF receptors, Flk-1/KDR and Flt-1, are described in Ortega, et. al., Amer. J. Pathol., 1997, 151, 1215–1224, and Dougher, et. al., Growth Factors, 1997, 14, 257–268. An in vitro assay for determining the affinity of pharmaceuticals of the present invention for the bFGF receptor is described in Yayon, et. al., Proc. Natl. Acad. Sci USA, 1993, 90, 10643–10647. Gho et. al., Cancer Research, 1997, 57, 3733–40, describe assays for angiogenin receptor binding peptides. Senger, et. al., Proc. Natl. Acad. Sci USA, 1997, 94, 13612–13617 describe assays for antagonists of the integrins a1B1 and a2B1. U.S. Patent No. 5,536,814 describes assays for compounds that bind to the integrin a5B1.

Oncomouse® Imaging

The study involves the use of the c-Neu Oncomouse® and FVB mice simultaneously as controls. The mice are anesthetized with sodium pentobarbital and injected with approximately 0.5 mCi of radiopharmaceutical. Prior to injection, the tumor locations on each Oncomouse® are recorded and tumor size measured using calipers. The animals are positioned on the camera head so as to image the anterior or posterior of the animals. Five minute dynamic images are acquired serially over 2 hours using a 256×256 matrix and a zoom of 2×. Upon completion of the study, the images are evaluated by circumscribing the tumor as the target region of interest (ROI) and a background site in the neck area below the carotid salivary glands.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the rate of growth of the tumors in control mice versus those in the mice administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

Rabbit Matrigel Model

This model was adapted from a matrigel model intended for the study of angiogenesis in mice. Matrigel (Becton & Dickinson, USA) is a basement membrane rich in laminin, collagen IV, entactin, HSPG and other growth factors. When combined with growth factors such as bFGF [500 ng/ml] or VEGF [2 μg/ml] and injected subcutaneously into the mid-abdominal region of the mice, it solidifies into a gel and stimulates angiogenesis at the site of injection within 4–8 days. In the rabbit model, New Zealand White rabbits (2.5–3.0 kg) are injected with 2.0 ml of matrigel, plus11 μg bFGF and 4 μg VEGF. The radiopharmaceutical is then injected 7 days later and the images obtained.

This model can also be used to assess the effectiveness of the radiopharmaceuticals of the present invention comprised of a beta, alpha or Auger electron emitting isotope. The radiopharmaceuticals are administered in appropriate amounts and the uptake at the angiogenic sites can be quantified either non-invasively by imaging for those isotopes with a coincident imageable gamma emission, or by excision of the angiogenic sites and counting the amount of radioactivity present by standard techniques. The therapeutic effect of the radiopharmaceuticals can be assessed by monitoring the rate of growth of the angiogenic sites in control rabbits versus those in the rabbits administered the radiopharmaceuticals of the present invention.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the angiogenic sites. The effectiveness of the contrast agents can be readily seen by comparison to the images obtain from animals that are not administered a contrast agent.

Canine Spontaneous Tumor Model

Adult dogs with spontaneous mammary tumors were sedated with xylazine (20 mg/kg)/atropine (1 ml/kg). Upon sedation the animals were intubated using ketamine (5 mg/kg)/diazepam (0.25 mg/kg) for full anethesia. Chemical restraint was continued with ketamine (3 mg/kg)/xylazine (6 mg/kg) titrating as necessary. If required the animals were ventilated with room air via an endotrachael tube (12 strokes/min, 25 ml/kg) during the study. Peripheral veins were catheterized using 20G I.V. catheters, one to serve as an infusion port for compound while the other for exfusion of blood samples. Heart rate and EKG were monitored using a cardiotachometer (Biotech, Grass Quincy, Mass.) triggered from a lead II electrocardiogram generated by limb leads. Blood samples are generally taken at 10 minutes (control), end of infusion, (1 minute), 15 min, 30 min, 60 min, 90 min, and 120 min for whole blood cell number and counting. Radiopharmaceutical dose was 300 µCi/kg administered as an i.v. bolus with saline flush. Parameters were monitored continuously on a polygraph recorder (Model 7E Grass) at a paper speed of 10 mm/min or 10 mm/sec.

Imaging of the laterals were for 2 hours with a 256×256 matrix, no zoom, 5 minute dynamic images. A known source is placed in the image field (20–90 µCi) to evaluate region of interest (ROI) uptake. Images were also acquired 24 hours post injection to determine retention of the compound in the tumor. The uptake is determined by taking the fraction of the total counts in an inscribed area for ROI/source and multiplying the known µCi. The result is µCi for the ROI.

This model can also be used to assess the effectiveness of the radiopharmaceuticals of the present invention comprised of a beta, alpha or Auger electron emitting isotope. The radiopharmaceuticals are administered in appropriate amounts and the uptake in the tumors can be quantified either non-invasively by imaging for those isotopes with a coincident imageable gamma emission, or by excision of the tumors and counting the amount of radioactivity present by standard techniques. The therapeutic effect of the radiopharmaceuticals can be assessed by monitoring the size of the tumors over time.

This model can also be used to assess the compounds of the present invention comprised of paramagnetic metals as MRI contrast agents. After administration of the appropriate amount of the paramagnetic compounds, the whole animal can be placed in a commercially available magnetic resonance imager to image the tumors. The effectiveness of the contrast agents can be readily seen by comparison to the images obtain from animals that are not administered a contrast agent.

Obviously, numerous modifications and variations of the present invention are possible in light of the above teachings. It is therefore to be understood that within the scope of the appended claims, the invention may be practiced otherwise that as specifically described herein.

What is claimed is:

1. A compound of formula (I):

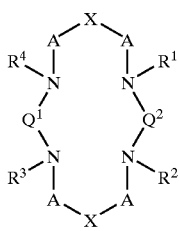

(I)

and pharmnaceutically acceptable salts thereof wherein:
$R^1$, $R^2$, $R^3$ and $R^4$ are independently selected at each occurrence from the group: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently elected at each occurrence from the group: H, C(=O)OR$^{18}$, $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is P(=O)R$^9$;

A is $CH_2$;

$Q^1$, $Q^2$, and $Q^3$ are independently —(CR$^{11}$R$^{12}$)$_n$—, wherein: n is 2–5;

$R^9$ is selected from the group: OR$^{14}$, NR$^{15}$R$^{16}$ and $CH_2$NR$^{15}$R$^{16}$;

$R^{11}$ and $R^{12}$ are independently selected from the group: H, $C_1$–$C_{10}$ alkyl substituted with 0–5 $R^{17}$, $C_2$–$C_{10}$ alkenyl substituted with 0–5 $R^{17}$ and aryl substituted with 0–3 $R^{17}$;

$R^{13}$ is independently selected at each occurrence from the group: H, OH, NHR$^{18}$, C(=O)R$^{18}$, OC(=O)R$^{18}$, OC(=O)OR$^{18}$, C(=O)OR$^{18}$, C(=O)NR$_2^{18}$, PO$_3$R$_2^{18}$, SR$^{18}$, SOR$^{18}$, SO$_2$R$^{18}$, NHC(=O)R$^{18}$, NHC(=O)NHR$^{18}$, $CH_2$OR$^{18}$, $CH_3$ and NHC(=S)NHR$^{18}$;

$R^{14}$, $R^{15}$ and $R^{16}$ are independently selected from the group: hydrogen, $C_1$–$C_{10}$ alkyl substituted with 0–5

$R^{13}$, $C_2$–$C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SR^{18}$, $SOR^{18}$, $SO_2R^{18}$, $NHC(=O)R^{18}$, $NHC(=O)NHR^{18}$ and $NHC(=S)NHR^{18}$; and $R^{18}$ is independently selected at each occurrence from the group: H, $C_1$–$C_6$ alkyl, benzyl and phenyl.

2. A compound of claim 1, wherein:

$R^9$ is $CH_2NR_{15}R^{16}$.

3. A compound of claim 2, wherein:

X is $P(=O)OH$;

$Q^1$, $Q^2$, and $Q^3$ are independently —$(CR^{11}R^{12})_n$—, wherein: n is 2 or 3;

$R^{11}$ and $R^{12}$ are independently selected from the group: H, $C_1$–$C_5$ alkyl substituted with 0–3 $R^{17}$ and aryl substituted with 0–1 $R^{17}$;

$R^{17}$ is independently selected at each occurrence from the group: H, OH, $NHR^{18}$, $C(=O)R^{18}$, $OC(=O)R^{18}$; $OC(=O)OR^{18}$, $C(=O)OR^{18}$, $C(=O)NR_2^{18}$, $PO_3R_2^{18}$, $SO_2R^{18}$, $NHC(=O)R^{18}$, $NHC(=O)NHR^{18}$ and $NHC(=S)NHR^{18}$; and $R^{18}$ is independently selected at each occurrence from the group: H and $C_1$–$C_3$ alkyl.

4. A compound of claim 3, wherein:

$R^1$, $R^2$, $R^3$ and $R^4$ are independently selected at each occurrence from the group: H, $CH_2COOH$, $CH_2PO_3H_2$ and $CH_2$—heterocycle substituted with 0–3 $R^{13}$; and $R^{13}$ is independently selected at each occurrence from the group: H, OH, $NH_2$, COOH, $PO_3H_2$, $CH_2OH$, $CH_3$ and $SO_3H$.

5. The compounds of claim 4 that are selected from the group:

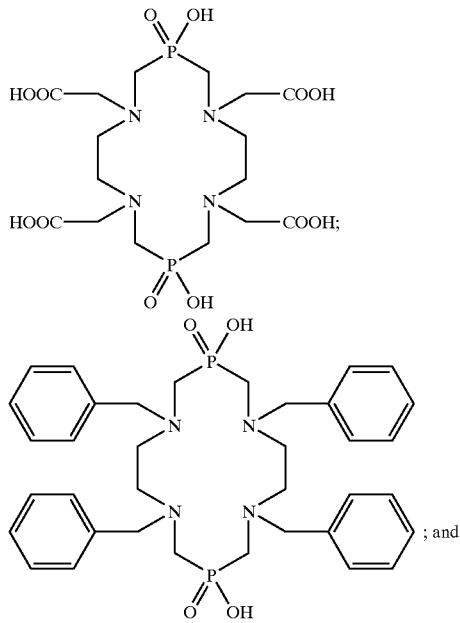

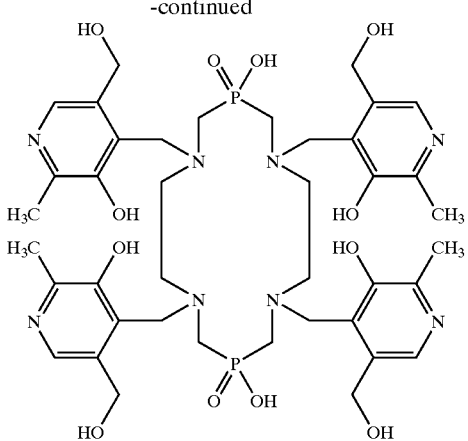

6. A radiopharmaceutical of formula (III):

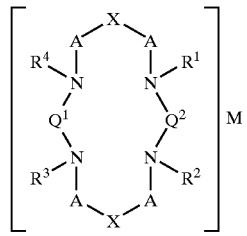

(III)

and pharmaceutically acceptable salts thereof, wherein:

M is selected from the group: $^{64}Cu$, $^{67}Cu$, $^{67}Ga$, 68Ga, $^{99m}Tc$, $^{111}In$, $^{90}Y$, $^{149}Pr$, $^{153}Sm$, $^{159}Gd$, $^{166}Ho$, $^{169}Yb$, $^{177}Lu$, $^{186}Re$ and $^{188}Re$;

$R^1$, $R^2$, $R^3$ and $R^4$ are independently selected at each occurrence from: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently elected at each occurrence from: H, $C(=O)OR^{18}$, $C(=O)OR^{23}$, $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is $P(=O)R^9$;

A is $CH_2$;

$Q^1$, $Q^2$, and $Q^3$ are independently —$(CR^{11}R^{12})_n$—, wherein: n is 2–5;

$R^9$ is selected from the group: $OR^{14}$, $NR^{15}R^{16}$ and $CH_2NR^{15}R^{16}$;

$R^{11}$ and $R^{12}$ are independently selected from the group: H, $C_1$–$C_{10}$ alkyl substituted with 0–5 $R^{17}$, $C_2$–$C_{10}$ alkenyl substituted with 0–5 $R^{17}$ and aryl substituted with 0–3 $R^{17}$;

$R^{13}$ is independently selected at each occurrence from the group: H, OH, $OR^{23}$, $NHR^{18}$, $C(=O)R^{18}$, $OC(=O)R^{18}$, $OC(=O)OR^{18}$, $OC(=O)OR^{23}$, $C(=O)OR^{18}$, $C(=O)OR^{23}$, $C(=O)NR_2^{18}$, $PO_3R_2^{18}$, $PO_3R^{18}R^{23}$, $SR^{18}$, $SR^{23}$, $SOR^{18}$, $SO_2R^{218}$, $SOR^{23}$, $SO_2R^{23}$, $NHC(=O)R^{18}$, $NHC(=O)NHR^{18}$, $CH_2OR^{18}$, $CH_2OR^{18}$, $CH_3$ and $NHC(=S)NHR^{18}$;

$R^{14}$, $R^{15}$ and $R^{16}$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SR^{18}$, $SOR^{18}$, $SO_2R^{18}$, $NHC(=O)R^{18}$, $NHC(=O)NHR^{18}$ and $NHC(=S)NHR^{18}$;

$R^{18}$ is independently selected at each occurrence from the group: H, $C_1$–$C_6$ alkyl, benzyl and phenyl; and $R^{23}$ is a bond to the metal M.

7. A radiopharmaceutical of claim 6, wherein:

$R^9$ is $CH_2NR^{15}R^{16}$.

8. A radiopharmaceutical of claim 7, wherein:

X is P(=O)OH;

$Q^1$, $Q^2$, and $Q^3$ are independently $—(CR^{11}R^{12})_n—$, wherein: n is 2 or 3;

$R^{11}$ and $R^{12}$ are independently selected from the group: H, $C_1$–$C_5$ alkyl substituted with 0–3 $R^{17}$ and aryl substituted with 0–1 $R^{17}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SO_2R^{18}$, $NHC(=O)R^{18}$, $NHC(=O)NHR^{18}$ and $NHC(=S)NHR^{18}$; and $R^{18}$ is independently selected at each occurrence from the group: H and $C_1$–$C_3$ alkyl.

9. A radiopharmaceutical of claim 8, wherein:

$R^1$, $R^2$, $R^3$ and $R^4$ are independently selected at each occurrence from the group: H, $CH_2COOH$, $CH_2PO_2H_2$ and $CH_2$heterocycle substituted with 0–3 $R^{13}$; and $R^{13}$ is independently selected at each occurrence from the group: H, $OR^{23}$, $OC(=O)OR^{23}$, $C(=O)OR^{23}$, $PO_3R^{18}R^{23}$, $SR^{23}$, $SOR^{23}$, $SO_2R^{23}$, $CH_2OR^{23}$, OH, $NH_2$, COOH, $PO_3H_2$, $CH_2OH$, $CH_3$ and $SO_3H$.

10. A radiopharmaceutical according to claim 6 of formula:

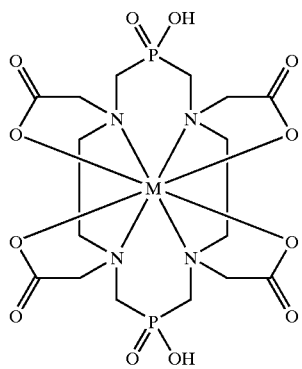

wherein:

M is selected from the group: $^{111}$In, $^{90}$Y and $^{177}$Lu.

11. A radiopharmaceutical according to claim 6 of formula:

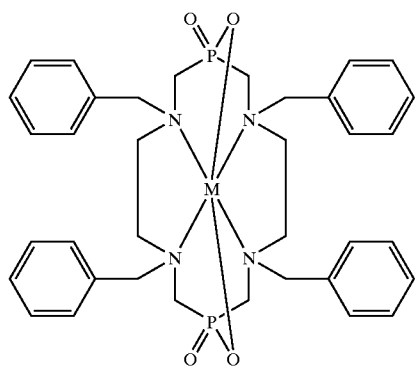

wherein:

M is selected from the group: $^{64}$Cu, $^{67}$Cu, $^{67}$Ga, $^{68}$Ga, $^{99m}$Tc, $^{111}$In, $^{90}$Y, $^{149}$Pr, $^{153}$Sm, $^{159}$Gd, $^{166}$Ho, $^{169}$Yb, 177Lu, $^{186}$Re and $^{188}$Re.

12. A radiopharmaceutical according to claim 6 of formula:

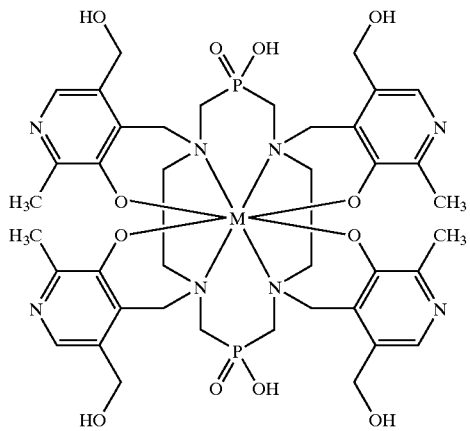

wherein:

M is selected from the group: $^{64}$Cu, $^{67}$Cu, $^{67}$Ga, $^{68}$Ga, $^{99m}$Tc, $^{111}$In, $^{90}$Y, $^{149}$Pr, $^{153}$Sm, $^{159}$Gd, $^{166}$Ho, $^{169}$Yb, $^{177}$Lu, $^{186}$Re and $^{188}$Re.

13. A MRI contrast agent of the formula (V):

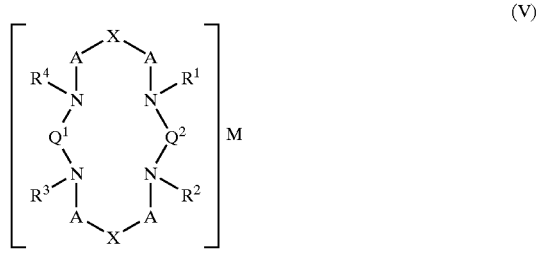

(V)

and pharmaceutically acceptable salts thereof, wherein:

M is a paramagnetic metal ion of atomic number selected from the group: 21–29, 42–44 and 58–70;

$R^1$, $R^2$, $R^3$ and $R^4$ are independently selected at each occurrence from: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently elected at each occurrence from: H, $C(=O)OR^{18}$, $C(=O)OR^{23}$, $C_1$–$C_{10}$ alkyl substituted with 0–5 $R1^3$, $C_2$–$C_{10}$ alkenyl substituted with 0–5 $R^{13}$, aryl substituted with 0–5 $R^{13}$ and heterocycle substituted with 0–5 $R^{13}$;

X is $P(=O)R^9$;

A is $CH_2$;

$Q^1$, $Q^2$, and $Q^3$ are independently —$(CR^{11}R^{12})_n$—, wherein: n is 2–5;

$R^9$ is selected from the group: $OR^{14}$, $NR^{15}R^{16}$ and $CH_2NR^{15}R^{16}$;

$R^{11}$ and $R^{12}$ are independently selected from the group: H, $C_1$–$C_{10}$ alkyl substituted with 0–5 $R^{17}$, $C_2$–$C_{10}$ alkenyl substituted with 0–5 $R^{17}$ and aryl substituted with 0–3 $R^{17}$;

$R^{13}$ is independently selected at each occurrence from the group: H, OH, $OR^{23}$, $NHR^{18}$, $C(=O)R^{18}$, $OC(=O)R^{18}$, $OC(=O)OR^{18}$, $OC(=O)R^{23}$, $C(=O)OR^{18}$, $C(=O)OR^{23}$, $C(=O)NR_2^{18}$, $PO_3R_2^{18}$, $PO_3R^{18}R^{23}$, $SR^{18}$, $SR^{23}$, $SOR^{18}$, $SO_2R^{18}$, $SOR^{23}$, $SO_2R^{23}$, $NHC(=O)R^{18}$, $NHC(=O)NHR^{18}$, $CH_2OR^{18}$, $CH_2OR^{23}$, $CH_3$ and $NHC(=S)NHR^{18}$;

$R^{14}$, $R^{15}$ and $R^{16}$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SR^{18}$, $SOR^{18}$, $SO_2R^{18}$, $NHC(=O)R^{18}$, $NHC(=O)NHR^{18}$ and $NHC(=S)NHR^{18}$;

$R^{18}$ is independently selected at each occurrence from the group: H, $C_1$–$C_6$ alkyl, benzyl and phenyl; and $R^{23}$ is a bond to the metal M.

14. A MRI contrast agent of claim 13, wherein:
$R^9$ is $CH_2NR^{15}R^{16}$.

15. A MRI contrast agent of claim 14, wherein:
X is $P(=O)OH$;

$Q^1$, $Q^2$, and $Q^3$ are independently —$(CR^{11}R^{12})_n$—, wherein: n is 2 or 3;

$R^{11}$ and $R^{12}$ are independently selected from the group: H, $C_1$–$C_5$ alkyl substituted with 0–3 $R^{17}$ and aryl substituted with 0–1 $R^{17}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SO_2R^{18}$, $NHC(=O)R^{18}$, $NHC(=O)NHR^{18}$ and $NHC(=S)NHR^{18}$; and $R^{18}$ is independently selected at each occurrence from the group: H and $C_1$–$C_3$ alkyl.

16. A MRI contrast agent of claim 15, wherein:
$R^1$, $R^2$, $R^3$ and $R^4$ are independently selected at each occurrence from the group: H, $CH_2COOH$, $CH_2PO_3H_2$ and $CH_2$—heterocycle substituted with 0–3 $R^{13}$; and $R^{13}$ is independently selected at each occurrence from the group: H, $OR^{23}$, $OC(=O)OR^{23}$, $C(=O)OR^{23}$, $PO_3R^{18}R^{23}$, $SR^{23}$, $SOR^{23}$, $SO_3R^{23}$, $CH_2OR^{23}$, OH, $NH_2$, COOH, $PO_3H_2$, $CH_2OH$, $CH_3$ and $SO_3H$.

17. A MRI contrast agent according to claim 13 of the formula:

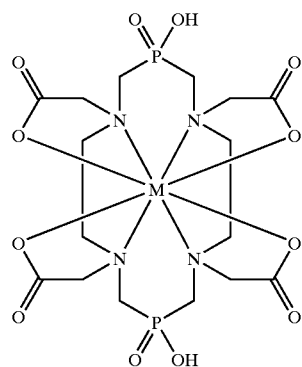

wherein:
M is a paramagnetic metal ion of atomic number selected from the group: 21–29, 42–44 and 58–70.

18. A MRI contrast agent according to claim 13 of the formula:

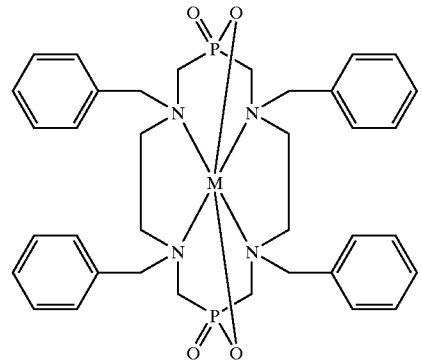

wherein:
M is a paramagnetic metal ion of atomic number selected from the group: 21–29, 42–44 and 58–70.

19. A MRI contrast agent according to claim 13 of the formula:

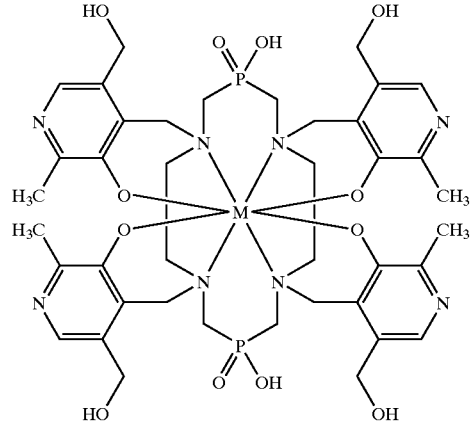

wherein: M is a paramagnetic metal ion of atomic number selected from the group: 21–29, 42–44, or 58–70.

20. A conjugate of the formula:

$C_h$—$L_n$—W, and pharmaceutically acceptable salts thereof, wherein:

$C_h$ is a chelator of formula (VII):

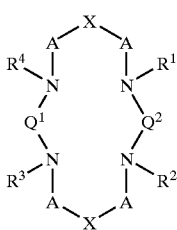

(VII)

wherein:

$R^1$, $R^2$, $R^3$ and $R^4$ are independently selected at each occurrence from the group: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently elected at each occurrence from the group: H, C(=O)OR$^{18}$, $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is P(=O)R$^9$;

A is CH$_2$;

$Q^1$, $Q^2$, and $Q^3$ are independently —(CR$^{11}$R$^{12}$)$_n$—, wherein: n is 2–5;

$R^9$ is selected from the group: OR$^{14}$, NR$^{15}$R$^{16}$ and CH$_2$NR$^{15}$R$^{16}$;

$R^{11}$ and $R^{12}$ are independently selected from the group: H, $C_1$–$C_{10}$ alkyl substituted with 0–5 $R^{17}$, $C_2$–$C_{10}$ alkenyl substituted with 0–5 $R^{17}$ and aryl substituted with 0–3 $R^{17}$;

$R^{13}$ is independently selected at each occurrence from the group: H, OH, NHR$^{18}$, C(=O)R$^{18}$, OC(=O) R$^{18}$, OC(=O)OR$^{18}$, C(=O)OR$^{18}$, C(=O)NR$_2$$^{18}$, PO$_3$R$_2$$^{18}$, SR$^{18}$, SOR$^{18}$, SO$_2$R$^{18}$, NHC(=O)R$^{18}$, NHC(=O)NHR$^{18}$, CH$_2$OR$^{18}$, CH$_3$, NHC(=S) NHR$^{18}$ and a bond to L$_n$;

$R^{14}$, $R^{15}$ and $R^{16}$ are independently selected from the group: hydrogen, $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, NHR$^{18}$, C(=O)R$^{18}$, OC(=O) R$^{18}$, OC(=O)OR$^{18}$, C(=O)OR$^{18}$, C(=O)NR$_2$$^{18}$, PO$_3$R$_2$$^{18}$, SR$^{18}$, SOR$^{18}$, SO$_2$R$^{18}$, NHC(=O)R$^{18}$, NHC(=O)NHR$^{18}$, NHC(=S)NHR$^{18}$ and a bond to L$_n$;

$R^{18}$ is independently selected at each occurrence from the group: H, $C_1$–$C_6$ alkyl, benzyl, phenyl and a bond to L$_n$;

$L_n$ is a linking group of formula:

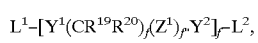

wherein:

$L^1$ is —[(CH$_2$)$_g$Z$^1$]$_g$—(CR$^{19}$R$^{20}$)$_{g''}$—;

$L^2$ is —(CR$^{19}$R$^{20}$)$_{g''}$—[Z$^1$(CH$_2$)$_g$]$_{g'}$—;

g is independently 0–10;

g' is independently 0–1;

g" is independently 0–10;

f is independently 0–10;

f' is independently 0–10;

f" is independently 0–1;

$Y^1$ and $Y^2$, at each occurrence, are independently selected from the group: a bond, O, NR$^{20}$, C=O, C(=O)O, OC(=O)O, C(=O)NH—, C=NR$^{20}$, S, SO, SO$_2$, NHC(=O), (NH)$_2$C(=O) and (NH)$_2$C=S;

$R^{19}$ and $R^{20}$ are independently selected at each occurrence from the group: H, $C_1$–$C_{10}$ alkyl substituted with 0–5 $R^{21}$ and alkaryl wherein the aryl is substituted with 0–5 $R^{21}$;

$R^{21}$ is independently selected at each occurrence from the group: NHR$^{22}$, C(=O)R$^{22}$, OC(=O) R$^{22}$, OC(=O)OR$^{22}$, C(=O)OR$^{22}$, C(=O)NR$_2$$^{22}$, —CN, SR$^{22}$, SOR$^{22}$, SO$_2$R$^{22}$, NHC(=O)R$^{22}$, NHC(=O)NHR$^{22}$, NHC(=S)NHR$^{22}$ and a bond to W;

$R^{22}$ is independently selected at each occurrence from the group: H, $C_1$–$C_6$ alkyl, benzyl, phenyl and a bond to W; and W is a biologically active molecule selected from the group: IIb/IIIa receptor ligands, fibrin binding peptides, leukocyte binding peptides, chemotactic peptides, somatostatin analogs, selectin binding peptides, vitronectin receptor antagonists and tyrosine kinase inhibitors.

21. A conjugate of claim 20, wherein:

$R^9$ is CH$_2$NR$^{15}$R$^{16}$;

g is independently 0–5;

g" is independently 0–5;

f is independently 0–5;

f' is independently 0–5;

$Y^1$ and $Y^2$, at each occurrence, are independently selected from the group: a bond, O, NR$^{20}$, C=O, C(=O)O, OC(=O)O, C(=O)NH—, SO, SO$_2$, NHC(=O), (NH)$_2$C(=O) and (NH)$_2$C=S; and $R^{21}$ is independently selected at each occurrence from the group: NHR$^{22}$, C(=O)R$^{22}$, OC(=O)R$^{22}$, OC(=O) OR$^{22}$, C(=O)OR$^{22}$, C(=O)NR$_2$$^{22}$, SO$_2$R$^{22}$, NHC (=O)R$^{22}$, NHC(=O)NHR$^{22}$, NHC(=S)NHR$^{22}$ and a bond to W.

22. A conjugate of claim 21, wherein:

X is P(=O)OH;

$Q^1$, $Q^2$, and $Q^3$ are independently —(CR$^{11}$R$^{12}$)$_n$—, wherein: n is 2 or 3;

$R^{11}$ and $R^{12}$ are independently selected from the group: H, $C_1$–$C_5$ alkyl substituted with 0–3 $R^{17}$ and aryl substituted with 0–1 $R^{17}$;

$R^{17}$ is independently selected at each occurrence from the group: H, OH, NHR$^{18}$, C(=O)R$^{18}$, OC(=O)R$^{18}$, OC(=O)OR$^{18}$, C(=O)OR$^{18}$, C(=O)NR$_2$$^{18}$, PO$_3$R$_2$$^{18}$, SO$_2$R$^{18}$, NHC(=O)R$^{18}$, NHC(=O)NHR$^{18}$ and NHC (=S)NHR$^{18}$; and $R^{18}$ is independently selected at each occurrence from the group: H and $C_1$–$C_3$ alkyl.

23. A conjugate of claim 22, wherein:

$R^1$, $R^2$, $R^3$ and $R^4$ are independently selected at each occurrence from the group: H, CH$_2$COOH, CH$_2$PO$_3$H$_2$ and CH$_2$—heterocycle substituted with 0–3 $R^{13}$.

24. A conjugate of claim 23, wherein:

$C_h$ is selected from the group:

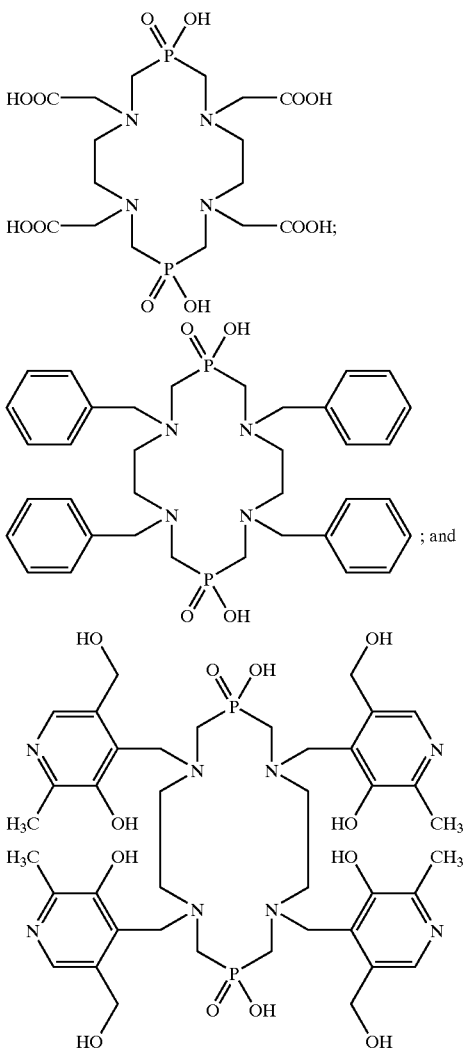
; and

25. A radiopharmaceutical of the formula:

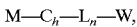

M—$C_h$—$L_n$—W, and pharmaceutically acceptable salts thereof, wherein,
M is selected from the group $^{64}$Cu $^{67}$Cu $^{67}$Ga, $^{68}$Ga, $^{99m}$Tc, $^{111}$In, $^{90}$Y, $^{149}$Pr, $^{153}$Sm, $^{159}$Gd, $^{166}$Ho, $^{169}$Yb, $^{177}$Lu, $^{186}$Re and $^{188}$Re;

$C_h$ is a chelator of formula (IX):

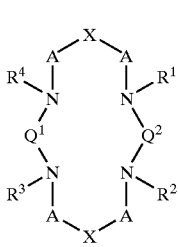

(IX)

wherein:
$R^1$, $R^2$, $R^3$ and $R^4$ are independently selected at each occurrence from the group: $C_1$–$C_{10}$ alkyl substituted with 0–5 $R^5$, $C_2$–$C_{10}$ alkenyl substituted with 0–5 $R^5$ and aryl substituted with 0–5 $R^5$;

$R^5$ is independently elected at each occurrence from the group: H, C(=O)O$R^{18}$, C(=O)O$R^{23}$, $C_1$–$C_{10}$ alkyl substituted with 0–5 $R^{13}$, $C_2$–$C_{10}$ alkenyl substituted with 0–5 $R^{13}$, aryl substituted with 0–5 $R^{13}$ and heterocycle substituted with 0–5 $R^{13}$;

X is P(=O)$R^9$;

A is CH$_2$;

$Q^1$, $Q^2$, and $Q^3$ are independently —(C$R^{11}R^{12}$)$_n$—, wherein: n is 2–5;

$R^9$ is selected from the group: O$R^{14}$, N$R^{15}R^{16}$ and CH$_2$N$R^{15}R^{16}$;

$R^{11}$ and $R^{12}$ are independently selected from the group: H, $C_1$–$C_{10}$ alkyl substituted with 0–5 $R^{17}$, $C_2$–$C_{10}$ alkenyl substituted with 0–5 $R^{17}$ and aryl substituted with 0–3 $R^{17}$;

$R^{13}$ is independently selected at each occurrence from the group: H, OH, O$R^{23}$, NH$R^{18}$, C(=O)$R^{18}$, OC(=O)O$R^{23}$, OC(=O)$R^{18}$, C(=O)O$R^{23}$, OC(=O)O$R^{18}$, C(=O)O$R^{18}$, C(=O)N$R_2^{18}$, PO$_3R_2^{18}$, PO$_3R^{18}R^{23}$, S$R^{18}$, S$R^{23}$, SO$R^{18}$, SO$_2R^{18}$, SO$R^{23}$, SO$_2R^{23}$, NHC(=O)$R^{18}$, NHC(=O)NH$R^{18}$, CH$_2$O$R^{18}$, CH$_2$O$R^{23}$, CH$_3$, NHC(=S)NH$R^{18}$ and a bond to $L_n$;

$R^{14}$, $R^{15}$ and $R^{16}$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, NH$R^{18}$, C(=O)$R^{18}$, OC(=O)$R^{18}$, OC(=O)O$R^{18}$, C(=O)O$R^{18}$, C(=O)N$R_{218}$, PO$_3R_2^{18}$, S$R^{18}$, SO$R^{18}$, SO$_2R^{18}$, NHC(=O)$R^{18}$, NHC(=O)NH$R^{18}$, NHC(=S)NH$R^{18}$ and a bond to $L_n$;

$R^{18}$ is independently selected at each occurrence from the group: H, $C_1$–$C_6$ alkyl, benzyl, phenyl and a bond to $L_n$;

$R^{23}$ is a bond to the metal M;

$L_n$ is a linking group of formula:

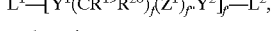

$L^1$—[$Y^1$(C$R^{19}R^{20}$)$_f$($Z^1$)$_{f'}$$Y^2$]$_{f''}$—$L^2$, wherein:
$L^1$ is —[(CH$_2$)$_g Z^1$]$_{g'}$—(C$R^{19}R^{20}$)$_{g''}$—;
$L^2$ is —(C$R^{19}R^{20}$)$_{g''}$—[$Z^1$(CH$_2$)$_g$]$_{g'}$—;
g is independently 0–10;
g' is independently 0–1;
g" is independently 0–10;
f is independently 0–10;
f' is independently 0–10;
f" is independently 0–1;
$Y^1$ and $Y^2$, at each occurrence, are independently selected from the group: a bond, O, N$R^{20}$, C=O, C(=O)O, OC(=O)O, C(=O)NH—, C=N$R^{20}$, S, SO, SO$_2$, NHC(=O), (NH)$_2$C(=O) and (NH)$_2$C=S;
$R^{19}$ and $R^{20}$ are independently selected at each occurrence from the group: H, $C_1$–$C_{10}$ alkyl substituted with 0–5 $R^{21}$ and alkaryl wherein the aryl is substituted with 0–5 $R^{21}$;
$R^{21}$ is independently selected at each occurrence from the group: NH$R^{22}$, C(=O)$R^{22}$, OC(=O)$R^{22}$, OC(=O)O$R^{22}$, C(=O)O$R^{22}$, C(=O)N$R_2^{22}$, —CN, S$R^{22}$, SO$R^{22}$, SO$_2R^{22}$, NHC(=O)$R^{22}$, NHC(=O)NH$R^{22}$, NHC(=S)NH$R^{22}$ and a bond to W;

R$^{22}$ is independently selected at each occurrence from the group: H, C$_1$–C$_6$ alkyl, benzyl, phenyl and a bond to W; and W is a biologically active molecule selected from the group: IIb/IIIa receptor ligands, fibrin binding peptides, leukocyte binding peptides, chemotactic peptides, somatostatin analogs, selectin binding peptides, vitronectin receptor antagonists and tyrosine kinase inhibitors.

26. A radiopharmaceutical of claim 25, wherein:

R$^9$ is CH$_2$NR$^{15}$R$^{16}$;

g is independently 0–5;

g" is independently 0–5;

f is independently 0–5;

f' is independently 0–5;

Y$^1$ and Y$^2$, at each occurrence, are independently selected from the group: a bond, O, NR$^{20}$, C=O, C(=O)O, OC(=O)O, C(=O)NH—, SO, SO$_2$, NHC(=O), (NH)$_2$C(=O) and (NH)$_2$C=S; and R$^{21}$ is independently selected at each occurrence from the group: NHR$^{22}$, C(=O)R$^{22}$, OC(=O)R$^{22}$, OC(=O)OR$^{22}$, C(=O)OR$^{22}$, C(=O)NR$_2$$^{22}$, SO$_2$R$^{22}$, NHC(=O)R$^{22}$, NHC(=O)NHR$^{22}$, NHC(=S)NHR$^{22}$ and a bond to W.

27. A radiopharmaceutical of claim 26, wherein:

X is P(=O)OH;

Q$^1$, Q$^2$, and Q$^3$ are independently —(CR$^{11}$R$^{12}$)$_n$—, wherein: n is 2 or 3;

R$^{11}$ and R$^{12}$ are independently selected from the group: H, C$_1$–C$_5$ alkyl substituted with 0–3 R$^{17}$ and aryl substituted with 0–1 R$^{17}$;

R$^{17}$ is independently selected at each occurrence from the group: H, OH, NHR$^{18}$, C(=O)R$^{18}$, OC(=O)R$^{18}$, OC(=O)OR$^{18}$, C(=O)OR$^{18}$, C(=O)NR$_2$$^{18}$, PO$_3$R$_2$$^{18}$, SO$_2$R$^{18}$, NHC(=O)R$^{18}$, NHC(=O)NHR$^{18}$ and NHC(=S)NHR$^{18}$; and R$^{18}$ is independently selected at each occurrence from the group: H and C$_1$–C$_3$ alkyl.

28. A radiopharmaceutical of claim 27, wherein:

R$^1$, R$^2$, R$^3$ and R$^4$ are independently selected at each occurrence from the group: H, CH$_2$COOH, CH$_2$PO$_3$H$_2$ and CH$_2$—heterocycle substituted with 0–3 R$^{13}$; and R$^{13}$ is independently selected at each occurrence from the group: H, OR$^{23}$, OC(=O)OR$^{23}$, C(=O)OR$^{23}$, PO$_3$R$^{18}$R$^{23}$, SR$^{23}$, SOR$^{23}$, SO$_2$R$^{23}$, CH$_2$OR$^{23}$, OH, NH$_2$, COOH, PO$_3$H$_2$, CH$_2$OH, CH3 and SO$_3$H.

29. A radiopharmaceutical of claim 28, wherein:

C$_h$ is selected from the group:

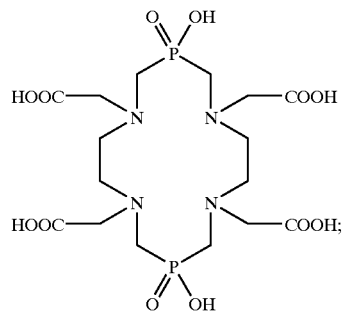

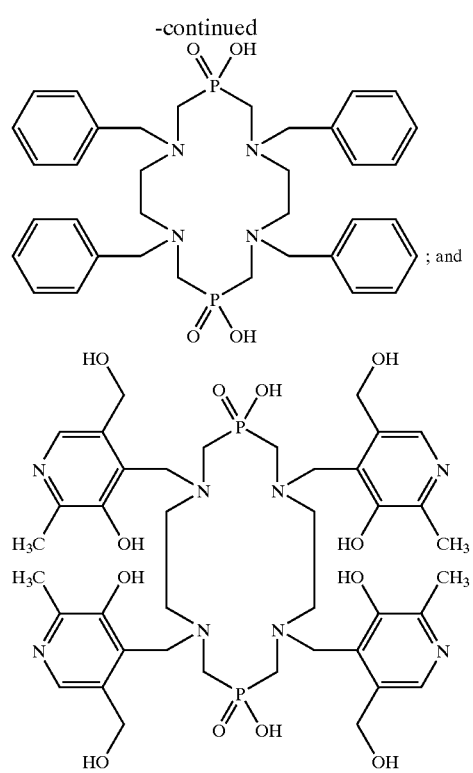

; and

30. A MRI contrast agent of the formula:

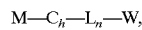

and pharmaceutically acceptable salt thereof, wherein:

M is a paramagnetic metal ion of atomic number selected from the group: 21–29, 42–44 and 58–70;

C$_h$ is a chelator of formula (XI):

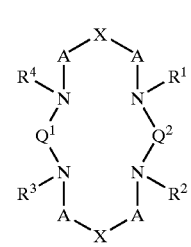

(XI)

wherein:

R$^1$, R$^2$, R$^3$ and R$^4$ are independently selected at each occurrence from the group: C$_1$–C$_{10}$ alkyl substituted with 0–5 R$^5$, C$_2$–C$_{10}$ alkenyl substituted with 0–5 R$^5$ and aryl substituted with 0–5 R$^5$;

R$^5$ is independently elected at each occurrence from the group: H, C(=O)OR$^{18}$, C(=O)OR$^{23}$, C$_1$–C$_{10}$ alkyl substituted with 0–5 R$^{13}$, C$_2$–C$_{10}$ alkenyl substituted with 0–5 R$^{13}$, aryl substituted with 0–5 R$^{13}$ and heterocycle substituted with 0–5 R$^{13}$;

X is P(=O)R$^9$;

A is CH$_2$;

Q$^1$, Q$^2$, and Q$^3$ are independently —(CR$^{11}$R$^{12}$)$_n$—, wherein: n is 2–5;

R$^9$ is selected from the group: OR$^{14}$, NR$^{15}$R$^{16}$ and CH$_2$NR$^{15}$R$^{16}$;

R$^{11}$ and R$^{12}$ are independently selected from the group: H, C$_1$–C$_{10}$ alkyl substituted with 0–5 R$^{17}$, C$_2$–C$_{10}$ alkenyl substituted with 0–5 $R^{17}$ and aryl substituted with 0–3 $R^{17}$;

$R^{13}$ is independently selected at each occurrence from the group: H, OH, $OR^{23}$, $NHR^{18}$, $C(=O)R^{18}$, $OC(=O)R^{18}$, $OC(=O)OR^{18}$, $OC(=O)OR^{23}$, $C(=O)OR^{18}$, $C(=O)OR^{23}$, $C(=O)NR_2^{18}$, $PO_3R_2^{18}$, $PO_3R^{18}R^{23}$, $SR^{18}$, $SR^{23}$, $SO^{18}R$, $SO_2R^{18}$, $SOR^{23}$, $SO_2R^{23}$, $NHC(=O)R^{18}$, $NHC(=O)NHR^{18}$, $CH_2OR^{18}$, $CH_2OR^{23}$, $CH_3$, $NHC(=S)NHR^{18}$ and a bond to $L_n$;

$R^{14}$, $R^{15}$ and $R^{16}$ are independently selected from the group: $C_1$–$C_{10}$ alkyl substituted with 0–5 $R^{13}$, $C_2$–$C_{10}$ alkenyl substituted with 0–5 $R^{13}$ and aryl substituted with 0–5 $R^{13}$;

or, alternatively, two $R^{14}$ or $R^{15}$ and $R^{16}$ may be taken together to form a transannular bridge, said bridge selected from the group: $C_3$–$C_{10}$ alkyl substituted with 0–5 $R^{13}$ and ortho-aryl substituted with 0–3 $R^{13}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SR^{18}$, $SOR^{18}$, $SO_2R^{18}$, $NHC(=O)R^{18}$, $NHC(=O)NHR^{18}$, $NHC(=S)NHR^{18}$ and a bond to $L_n$;

$R^{18}$ is independently selected at each occurrence from the group: H, $C_1$–$C_6$ alkyl, benzyl, phenyl and a bond to $L_n$;

$R^{23}$ is a bond to the metal M;

$L_n$ is a linking group of formula:

$L^1-[Y^1(CR^{19}R^{20})_f(Z^1)_{f'}Y^2]_{f''}-L^2$, wherein:

$L^1$ is $-[(CH_2)_gZ^1]_{g'}-(CR^{19}R^{20})_{g''}-$;
$L^2$ is $-(CR^{19}R^{20})_{g''}-[Z^1(CH_2)_g]_{g'}-$;
g is independently 0–10;
g' is independently 0–1;
g" is independently 0–10;
f is independently 0–10;
f' is independently 0–10;
f" is independently 0–1;

$Y^1$ and $Y^2$, at each occurrence, are independently selected from the group: a bond, O, $NR^{20}$, C=O, C(=O)O, OC(=O)O, C(=O)NH—, C=NR$^{20}$, S, SO, $SO_2$, NHC(=O), $(NH)_2C(=O)$ and $(NH)_2C=S$;

$R_{19}$ and $R^{20}$ are independently selected at each occurrence from: H, $C_1$–$C_{10}$ alkyl substituted with 0–5 $R^{21}$ and alkaryl wherein the aryl is substituted with 0–5 $R^{21}$;

$R^{21}$ independently selected at each occurrence from the group: $NHR^{22}$, $C(=O)R^{22}$ $OC(=O)R$, $OC(=O)OR$, $C(=O)OR$, $C(=O)NR_2^{22}$, —CN, $SR^{22}$, SOR, $SO_2R^{22}$, $NHC(=O)R^{22}$, $NHC(=O)NHR^{22}$, $NHC(=S)NHR^{22}$ and a bond to W; $R^{22}$ is independently selected at each occurrence from the group: H, $C_1$–$C_6$ alkyl, benzyl, !r;80 phenyl and a bond to W; and W is a biologically active molecule selected from the group: IIb/IIIa receptor ligands, fibrin binding peptides, leukocyte binding peptides, chemotactic peptides, somatostatin analogs, selectin binding peptides, vitronectin receptor antagonists and tyrosine kinase inhibitors.

31. A MRI contrast agent of claim 30, wherein:
$R^9$ is $CH_2NR^{15}R^{16}$;
g is independently 0–5;
g" is independently 0–5;
f is independently 0–5;
f' is independently 0–5;

$Y^1$ and $Y^2$, at each occurrence, are independently selected from the group: a bond, O, $NR^{20}$, C=O, C(=O)O, OC(=O)O, C(=O)NH—, SO, $SO_2$, NHC(=O), (NH)$_2$C(=O) and (NH)$_2$C=S; and $R^{21}$ is independently selected at each occurrence from the group selected from the group: $NHR^{22}$, $C(=O)R^{22}$, $OC(=O)R^{22}$, $OC(=O)OR^{22}$, $C(=O)OR^{22}$, $C(=O)NR_2^{22}SO_2R^{22}$, $NHC(=O)R^{22}$, $NHC(=O)NHR^{22}$, $NHC(=S)NHR^{22}$ and a bond to W.

32. A MRI contrast agent of claim 31, wherein:

X is P(=O)OH;

$Q^1$, $Q^2$, and $Q^3$ are independently —$(CR^{11}R^{12})_n$—, wherein n: is 2 or 3;

$R^{11}$ and $R^{12}$ are independently chosen from the group: H, $C_1$–$C_5$ alkyl substituted with 0–3 $R^{17}$ and aryl substituted with 0–1 $R^{17}$;

$R^{17}$ is independently selected at each occurrence from the group: H, OH, $NHR^{18}$, $C(=O)R^{18}$, $OC(=O)R^{18}$, $OC(=O)OR^{18}$, $C(=O)OR^{18}$, $C(=O)NR_2^{18}$, $PO_3R_2^{18}$, $SO_2R^{18}$, $NHC(=O)R^{18}$, $NHC(=O)NHR^{18}$ and $NHC(=S)NHR^{18}$; and $R^{18}$ is independently selected at each occurrence from the group: H and $C_1$–$C_3$ alkyl.

33. A MRI contrast agent of claim 32, wherein:
$R^1$, $R^2$, $R^3$ and $R^4$ are independently selected at each occurrence from the group: H, $CH_2COOH$, $CH_2PO_3H_2$, $CH_2$—heterocycle substituted with 0–3 $R^{13}$; and $R^{13}$ is independently selected at each occurrence from the group: H, $OR^{23}$, $OC(=O)OR^{23}$, $C(=O)OR^{23}$, $PO_3R^{18}R^{23}$, $SR^{23}$, $SOR^{23}$, $SO_2R^{23}$, $CH_2OR^{23}$, OH, $NH_2$, COOH, $PO_3H_2$, $CH_2OH$, CH3 and $SO_3H$.

34. A MRI contrast agent of claim 33, wherein:
$C_h$ is selected from the group:

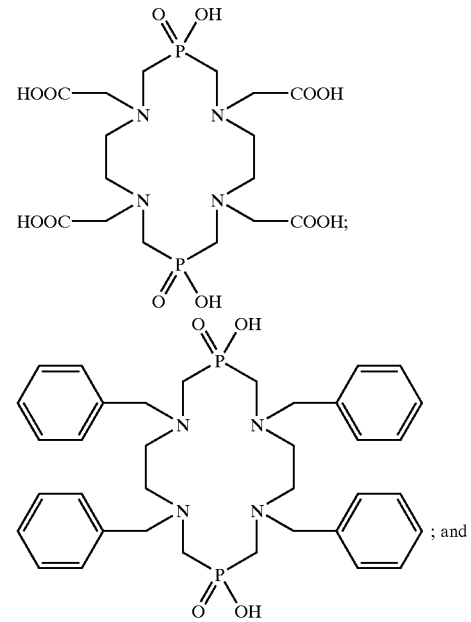

-continued
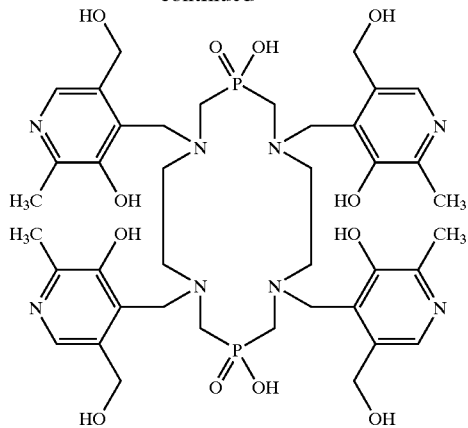
* * * * *

UNITED STATES PATENT AND TRADEMARK OFFICE
CERTIFICATE OF CORRECTION

PATENT NO. : 6,685,914 B1
DATED : February 3, 2004
INVENTOR(S) : Shuang Liu

It is certified that error appears in the above-identified patent and that said Letters Patent is hereby corrected as shown below:

Column 2,
Line 53, please delete "diethylenetriaminepetaacetic" and insert
-- diethylenetriaminepentaacetic -- therefor.

Column 5,
Line 14, please delete "$C_{3-C10}$" and insert -- $C_3$-$C_{10}$ -- therefor.

Column 6,
Line 3, please delete "$PO_3R^{18}$" and insert -- $PO_3R_2^{18}$ -- therefor.

Column 9,
Line 50, please delete "64Cu, $^{67}$Cu, 67Ga, 68Ga," and insert -- $^{64}$Cu, $^{67}$Cu, $^{67}$Ga, $^{68}$Ga, -- therefor.

Column 10,
Line 44, please delete "$R^{13}$" and insert -- $R^{17}$ -- therefor.

Column 13,
Line 60, please delete "$_{C1}$-$C_{10}$" and insert -- $C_1$-$C_{10}$ -- therefor.

Column 14,
Line 4, please delete "$PO_2R^{18}$" and insert -- $PO_3R_2^{18}$ -- therefor.
Line 15, please delete "–$(CR^{19}R^{20})_{g'''}$–$[Z^1(CH_2)_{g''}]_{g'}$–;" and insert -- –$(CR^{19}R^{20})_{g'''}$–$[Z^1(CH_2)_g]_{g'}$–; -- therefor.
Line 49, please delete "$NR^{18}$" and insert -- $NR^8$ -- therefor.
Line 52, please delete "$S(=O)_2R^{184}$" and insert -- $S(=O)_2R^{14}$ -- therefor.

Column 16,
Line 62, please delete "$Q_1$" and insert -- $Q^1$ -- therefor.

Column 17,
Line 3, please delete "$C_3$-$C^{10}$" and insert -- $C_3$-$C_{10}$ -- therefor.
Line 11, please delete "$C_2$-$C^{10}$" and insert -- $C_2$-$C_{10}$ -- therefor.
Line 43, please delete "-$[(CH_2)_gZ^1]_{g'}$-$(_{CR}^{19}R^{20})_{g''}$-," and insert -- -$[(CH_2)_gZ^1]_{g'}$-$(CR^{19}R^{20})_{g''}$-- therefor.

Column 18,
Line 62, please delete "$OC(O)OR^{23}$, $C(O)OR^{23}$," and insert -- $OC(=O)OR^{23}$, $C(=O)OR^{23}$, -- therefor.

UNITED STATES PATENT AND TRADEMARK OFFICE
CERTIFICATE OF CORRECTION

PATENT NO. : 6,685,914 B1
DATED : February 3, 2004
INVENTOR(S) : Shuang Liu

It is certified that error appears in the above-identified patent and that said Letters Patent is hereby corrected as shown below:

Column 20,
Line 21, please delete the second occurrence of "is".
Lines 44-45, please delete "OC(O)$R^{18}$," and insert -- OC(=O)$R^{18}$, -- therefor.
Line 47, please delete "$SO_2$, $SR^{18}$," and insert -- $SO_2R^{18}$, -- therefor.

Column 21,
Line 18, please delete "SO2t" and insert -- $SO_2$, -- therefor.

Column 22,
Line 26, please delete "$R^1$, $R^2$, and $R^3$" and insert -- $R^1$, $R^2$, $R^3$ and $R^4$ -- therefor.
Line 37, please delete "R13" and insert -- $R^{13}$ -- therefor.
Line 38, please delete "OC(O)$OR^{23}$" and insert -- OC(=O)$OR^{23}$ -- therefor.

Column 23,
Line 62, please delete "substitent" and insert -- substituent -- therefor.

Column 24,
Line 11, please delete "O-2" and insert -- 0-2 -- therefor.

Column 28,
Line 40, please delete "chiorbutanol" and insert -- chlorbutanol -- therefor.

Column 30,
Line 42, please delete "PhosThine-Oxo" and insert -- Phosphine-Oxo -- therefor.
Lines 44-45, please delete "(M ärkl, V. G., et al. Tetrhedron Letters" and insert
-- (Märkl, V. G., et al., Tetrahedron Letters, -- therefor.
Line 62, please delete "tatraaza" and insert -- tetraaza -- therefor.

Column 35,
Line 31, please delete "Macrocyles" and insert -- Macrocycles -- therefor.
Line 64, please delete "tatraaza" and insert -- tetraaza -- therefor.

Column 42,
Line 64, please delete "Hydroxvamine" and insert -- Hydroxyamine -- therefor.

Column 48,
Line 47, please delete "0 OC" and insert -- 0° C -- therefor.

Column 50,
Line 59, please delete "464Q," and insert -- 4640, --; and delete "lipoproten" and insert
-- lipoprotein -- therefor.

UNITED STATES PATENT AND TRADEMARK OFFICE
CERTIFICATE OF CORRECTION

PATENT NO.     : 6,685,914 B1                                           Page 3 of 4
DATED          : February 3, 2004
INVENTOR(S)    : Shuang Liu It is certified that error appears in the above-identified patent and that said Letters Patent is hereby corrected as shown below:

Column 55,
Line 60, please delete "hexaahydrate" and insert -- hexahydrate -- therefor.

Column 56,
Line 13, please delete "triahydrate" and insert -- trihydrate -- therefor.
Line 28, please delete "(300 pL HPLC" and insert -- (300 $\mu$L HPLC -- therefor.
Line 47, please delete "6.5." and insert -- ~6.5. -- therefor.

Column 57,
Line 64, please delete the second occurrence of "images".

Column 67,
Line 16, please delete "$CH_2NR_{15}R^{16}$" and insert -- $CH_2NR^{14}R^{15}$ -- therefor.
Line 17, please delete "claim 2," and insert -- claim 1, -- therefor.
Line 35, please delete "$CH_2PO\ H_2$" and insert -- $CH_2PO_3H_2$ -- therefor.

Column 68,
Line 34, please delete "68Ga" and insert -- $^{68}Ga$ -- therefor.
Line 61, please delete "$SO_2R^{218}$," and insert -- $SO_2R^{18}$, -- therefor.
Line 62, please delete "$CH_2OR^{18}$," and insert -- $CH_2OR^{23}$, -- therefor.

Column 69,
Line 16, please delete "$CH_2NR^{15}R^{16}$." and insert -- $CH_2NR^{14}R^{15}$. -- therefor.
Line 17, please delete "claim 7," and insert -- claim 6, -- therefor.
Line 37, please delete "$CH_2PO_2H_2$" and insert -- $CH_2PO_3H_2$ -- therefor.
Line 38, please delete "$CH_2$ heterocycle" and insert -- $CH_2$-heterocycle -- therefor.

Column 71,
Line 1, please delete "$R1^3$," and insert -- $R^{13}$, -- therefor.
Line 42, please delete "$CH_2NR^{15}R^{16}$." and insert -- $CH_2NR^{14}R^{15}$. -- therefor.
Line 43, please delete "claim 14," and insert -- claim 13, -- therefor.
Line 64, please delete "$SO_3R^{23}$," and insert -- $SO_2R^{23}$, -- therefor.

Column 73,
Line 41, please delete "hydrogen".

Column 74,
Line 31, please delete "$CH_2NR^{15}R^{16}$;" and insert -- $CH_2NR^{14}R^{15}$; -- therefor.
Line 47, please delete "claim 21," and insert -- claim 20, -- therefor.

Column 76,
Line 17, please delete "$OC(=O)OR^{23}, OC(=O)OR^{18}, C(=O)OR^{23}$," and insert
-- $OC(=O)R^{18}, OC(=O)OR^{18}, OC(=O)OR^{23}$, -- therefor.

UNITED STATES PATENT AND TRADEMARK OFFICE
CERTIFICATE OF CORRECTION

PATENT NO. : 6,685,914 B1
DATED : February 3, 2004
INVENTOR(S) : Shuang Liu

It is certified that error appears in the above-identified patent and that said Letters Patent is hereby corrected as shown below:

Column 76 (cont'd),
Line 18, please delete "$OC(=O)OR^{18}$, $C(=O)OR^{18}$," and insert -- $C(=O)OR^{18}$, $C(=O)OR^{23}$, -- therefor.
Line 33, please delete "$C(=O)NR_{218}$," and insert -- $C(=O)NR_2^{18}$, -- therefor.

Column 77,
Line 11, please delete "$CH_2NR^{15}R^{16}$;" and insert -- $CH_2NR^{14}R^{15}$; -- therefor.
Line 28, please delete "claim 26," and insert -- claim 25, -- therefor.

Column 79,
Line 7, please delete "$SO^{18}R$," and insert -- $SOR^{18}$, -- therefor.
Line 52, please delete "$C(=O)R^{22}$ $OC(=O)R$," and insert -- $C(=O)R^{22}$, $OC(=O)R^{22}$, -- therefor.
Line 53, please delete "$OC(=O)OR$ , $C(=O)OR$," and insert -- $OC(=O)OR^{22}$, $C(=O)OR^{22}$, -- therefor.
Line 54, please delete "$SOR$," and insert -- $SOR^{22}$, -- therefor.
Line 55, please delete "$R^{22}$ is"
Line 56, please insert -- $R^{22}$ is -- before "independently".
Line 57, please delete "Ir;80".
Line 66, please delete "$CH_2NR^{15}R^{16}$;" and insert -- $CH_2NR^{14}R^{15}$; -- therefor.

Column 80,
Line 13, please delete "$NR_2^{22}SO_2R^{22}$," and insert -- $NR_2^{22}$, $SO_2R^{22}$, -- therefor.
Line 15, please delete "claim 31," and insert -- claim 30, -- therefor.
Line 39, please delete "CH3" and insert -- $CH_3$ -- therefor.

Signed and Sealed this

Fourteenth Day of June, 2005

JON W. DUDAS
*Director of the United States Patent and Trademark Office*

SEQUENCE LISTING

<160> NUMBER OF SEQ ID NOS: 11

<210> SEQ ID NO 1
<211> LENGTH: 16
<212> TYPE: PRT
<213> ORGANISM: Artificial Sequence
<220> FEATURE:
<223> OTHER INFORMATION: Synthetic construct

<400> SEQUENCE: 1

Met Thr Tyr Arg Pro Asp Leu Asp Glu Arg Lys Gln Gln Lys Arg Glu
1               5                   10                  15

<210> SEQ ID NO 2
<211> LENGTH: 18
<212> TYPE: PRT
<213> ORGANISM: Artificial Sequence
<220> FEATURE:
<223> OTHER INFORMATION: Synthetic construct

<400> SEQUENCE: 2

Ala Gln Leu Ala Gly Glu Cys Arg Glu Asn Val Cys Met Gly Ile Glu
1               5                   10                  15

Gly Arg

<210> SEQ ID NO 3
<211> LENGTH: 8
<212> TYPE: PRT
<213> ORGANISM: Artificial Sequence
<220> FEATURE:
<223> OTHER INFORMATION: Synthetic construct

<400> SEQUENCE: 3

Ala Pro Ser Gly His Tyr Lys Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic construct

```
<400> SEQUENCE: 4

Lys Arg Thr Gly Gln Tyr Lys Leu
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: Cyclo

<400> SEQUENCE: 5

Arg Gly Asp Arg Gly Asp
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(6)
<223> OTHER INFORMATION: Cyclo
<220> FEATURE:
<221> NAME/KEY: misc_feature
<222> LOCATION: (6)..(6)
<223> OTHER INFORMATION: D-Asp

<400> SEQUENCE: 6

Arg Gly Asp Arg Gly Xaa
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic construct

<400> SEQUENCE: 7

Arg Gly Asp Arg Gly Asp
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(5)
<223> OTHER INFORMATION: Cyclo
<220> FEATURE:
<221> NAME/KEY: misc_feature
<222> LOCATION: (5)..(5)
<223> OTHER INFORMATION: Mamb

<400> SEQUENCE: 8

Ala Arg Gly Asp Xaa
1               5

<210> SEQ ID NO 9
```

```
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(11)
<223> OTHER INFORMATION: Cyclo
<220> FEATURE:
<221> NAME/KEY: misc_feature
<222> LOCATION: (7)..(7)
<223> OTHER INFORMATION: BTD

<400> SEQUENCE: 9

Arg Gly Asp Val Gly Ser Xaa Ser Gly Val Ala
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(9)
<223> OTHER INFORMATION: Cyclo

<400> SEQUENCE: 10

Cys Asp Cys Arg Gly Asp Cys Phe Cys
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(5)
<223> OTHER INFORMATION: Cyclo

<400> SEQUENCE: 11

Cys Asn Gly Asp Cys
1               5
```